United States Patent
Lo et al.

(10) Patent No.: US 11,926,821 B2
(45) Date of Patent: Mar. 12, 2024

(54) CELL-FREE DNA QUALITY

(71) Applicant: The Chinese University of Hong Kong, New Territories (HK)

(72) Inventors: Yuk-Ming Dennis Lo, Hong Kong SAR (CN); Cheuk Ho Tsang, Hong Kong SAR (CN); Peiyong Jiang, Hong Kong SAR (CN); Si Long Vong, Hong Kong SAR (CN); Rossa Wai Kwun Chiu, Hong Kong SAR (CN)

(73) Assignee: The Chinese University of Hong Kong, New Territories (HK)

( * ) Notice: Subject to any disclaimer, the term of this patent is extended or adjusted under 35 U.S.C. 154(b) by 1177 days.

(21) Appl. No.: 16/658,677

(22) Filed: Oct. 21, 2019

(65) Prior Publication Data
US 2020/0123532 A1 Apr. 23, 2020

Related U.S. Application Data

(60) Provisional application No. 62/748,767, filed on Oct. 22, 2018.

(51) Int. Cl.
| | |
|---|---|
| *C12N 15/10* | (2006.01) |
| *G16B 40/10* | (2019.01) |
| *C40B 40/06* | (2006.01) |
| *G16B 30/10* | (2019.01) |
| *G16B 30/20* | (2019.01) |
| *G16B 20/20* | (2019.01) |
| *C12Q 1/6827* | (2018.01) |
| *C12Q 1/6869* | (2018.01) |
| *G16B 20/00* | (2019.01) |
| *G16B 20/10* | (2019.01) |
| *G16B 40/00* | (2019.01) |

(52) U.S. Cl.
CPC ....... *C12N 15/1065* (2013.01); *C12Q 1/6827* (2013.01); *C12Q 1/6869* (2013.01); *C40B 40/06* (2013.01); *G16B 20/00* (2019.02); *G16B 20/10* (2019.02); *G16B 20/20* (2019.02); *G16B 30/10* (2019.02); *G16B 30/20* (2019.02); *G16B 40/00* (2019.02); *G16B 40/10* (2019.02)

(58) Field of Classification Search
CPC ........ G16B 30/10; G16B 20/20; G16B 40/00; G16B 20/00; G16B 30/20; C12Q 1/6827; C12Q 1/6869
See application file for complete search history.

(56) References Cited

U.S. PATENT DOCUMENTS

| | | | |
|---|---|---|---|
| 2016/0217251 A1* | 7/2016 | Lo | G16B 20/20 |
| 2018/0245072 A1* | 8/2018 | Raymond | C12Q 1/686 |
| 2018/0251848 A1* | 9/2018 | Diehn | C12Q 1/6886 |

FOREIGN PATENT DOCUMENTS

| | | |
|---|---|---|
| CN | 104830986 A | 8/2015 |
| CN | 107794575 A | 3/2018 |
| CN | 108624584 A | 10/2018 |
| WO | 2015057985 A1 | 4/2015 |
| WO | 2016040901 A1 | 3/2016 |
| WO | 2017096322 A1 | 6/2017 |

OTHER PUBLICATIONS

Chandrananda et al., High-resolution characterization of sequence signatures due to non-random cleave of cell-free DNA, 2015, BMC Medical Genomics, 8:29, p. 1-19 (Year: 2015).*
Yin et al., Prior DNA repair improves the read quality in next-generation sequencing of cell-free tumor DNA, Apr. 2018, AACR, Cancer Res, 78(13 Suppl):3647, p. 1-2 (Year: 2018).*
Chen et al., DNA Damage is a major cause of sequencing errors, directly confounding variant identification, 2016, bioRxiv preprint, p. 1-30 (Year: 2016).*
Newman et al., Integrated digital error suppression for improved detection of circulating tumor DNA, 2016, nature biotechnology, p. 547-555 and Online Metohds (Year: 2016).*
European Application No. 19877370.7, Extended European Search Report dated Jun. 27, 2022, 6 pages.
Singapore Application No. 11202102994R, Written Opinion dated Nov. 23, 2022, 8 pages.
Taiwan Application No. 108138130, Office Action dated Jun. 29, 2021, 6 pages.
International Search Report and Written Opinion dated Feb. 6, 2020 in International Patent Application No. PCT/CN2019/112448. 10 pages.
San Pietro, David et al.; "A preliminary assessment of the effect of PreCR™ DNA repair treatment on mixture ratios in two person mixtures"; Science & Justice; 2018; vol. 58, Issue 5; pp. 308-314.

* cited by examiner

*Primary Examiner* — Kaitlyn L Minchella
(74) *Attorney, Agent, or Firm* — Kilpatrick Townsend & Stockton LLP

(57) ABSTRACT

The quality of cell-free DNA for analysis is improved by techniques described herein. Cell-free DNA may include DNA with defects that do not allow for analysis of those DNA with techniques such as sequencing and targeted capture enrichment. These defects may be defects within the strands of the DNA and not present at the ends of the DNA. These intrastrand defects in cell-free DNA can be repaired. The repair of the defects in cell-free DNA may then allow for these repaired cell-free DNA to be analyzed by techniques, including sequencing and targeted capture enrichment.

14 Claims, 39 Drawing Sheets
(24 of 39 Drawing Sheet(s) Filed in Color)

Intact dsDNA

Nicked DNA

Gapped DNA

Abasic DNA

DNA-protein crosslinking

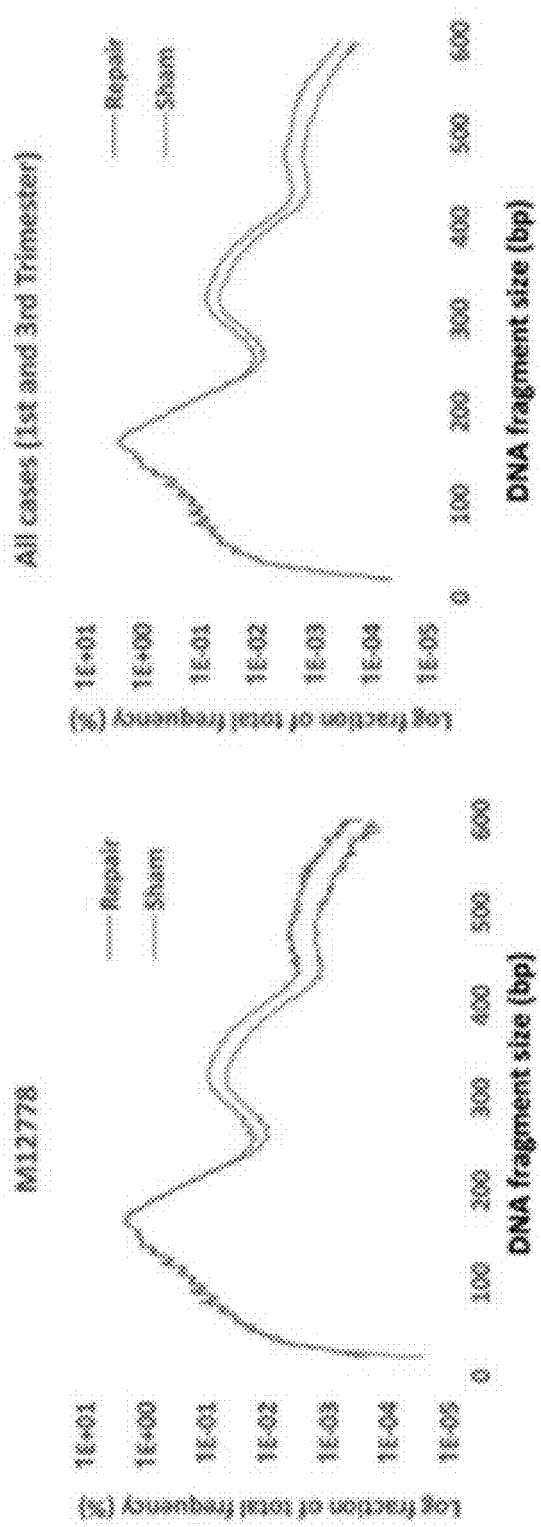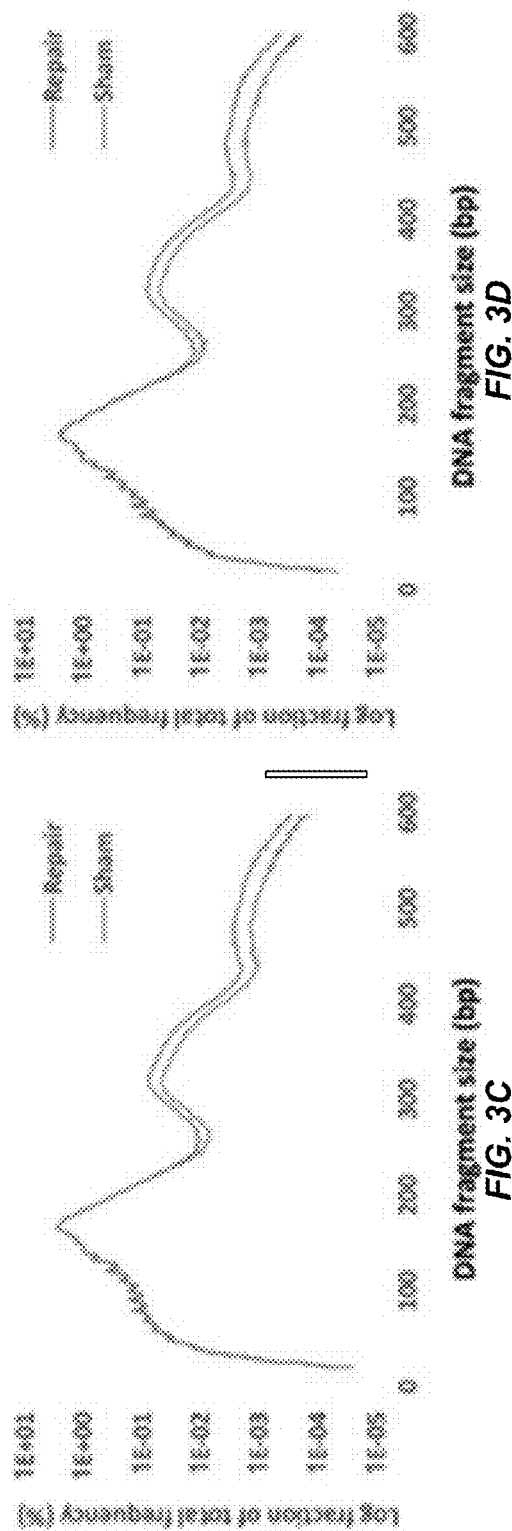
FIG. 3A  FIG. 3B  FIG. 3C  FIG. 3D

| Size range | | M12792 | M12922 | T21 subject M12930 | M12949 | M12952 |
|---|---|---|---|---|---|---|
| Short (0-250 bp) | Sham | 96.6% | 96.3% | 95.6% | 94.6% | 96.6% |
| | Repair | 93.7% | 92.1% | 92.0% | 90.0% | 93.1% |
| | Relative % change | -3.0% | -4.4% | -3.8% | -5.1% | -3.6% |
| | Absolute % change | -2.9% | -4.2% | -3.6% | -4.6% | -3.5% |
| Long (>250 bp) | Sham | 3.4% | 3.7% | 4.4% | 5.4% | 3.4% |
| | Repair | 6.3% | 7.9% | 8.0% | 10.0% | 6.9% |
| | Relative % change | 85.3% | 113.5% | 81.8% | 85.2% | 102.9% |
| | Absolute % change | 2.9% | 4.2% | 3.6% | 4.6% | 3.5% |

FIG. 13

| | Sample no. | SLEDAI | Anti-dsDNA antibody level (IU/mL) | Total DNA amount (ng) from 4 mL plasma |
|---|---|---|---|---|
| Inactive | S113 | 0 | 0 | 9.73 |
| | S117 | 2 | 0 | 16.8 |
| Active | S312 | 8 | >1000 | 2.3 |
| | S494 | 8 | >1000 | 3.1 |

*FIG. 18*

| Size range | Sham to Repair percentage change | | | | Repair | | | |
|---|---|---|---|---|---|---|---|---|
| | Inactive SLE | | Active SLE | | Inactive SLE | | Active SLE | |
| | S113 | S117 | S312 | S494 | S113 | S117 | S312 | S494 |
| Short (0-250 bp) | 96.6% to 94.2% (-2.5%) | 98.2% to 96.1% (-2.1%) | 96.4% to 94.9% (-1.6%) | 98.0% to 96.7% (-1.3%) | 94.2% | 96.1% | 94.9% | 96.7% |
| Long (>250 bp) | 3.4% to 5.8% (70.6%) | 1.8% to 3.9% (116.7%) | 3.6% to 5.1% (41.7%) | 2.0% to 3.3% (65%) | 5.8% | 3.9% | 5.1% | 3.3% |
| 0-115 bp | 3.5% to 3.1% (-11.4%) | 5.1% to 4.2% (-17.6%) | 10.8% to 10.3% (-4.6%) | 12.7% to 12.2% (-3.9%) | 3.1% | 4.2% | 10.3% | 12.2% |
| >200 bp | 7.1% to 9.4% (32.4%) | 3.6% to 5.8% (61.1%) | 9.7% to 11.4% (17.5%) | 5.8% to 7.3% (25.9%) | 9.4% | 5.8% | 11.4% | 7.3% |
| 120-130 bp | 2.1% to 2.1% (0.7%) | 2.8% to 2.7% (-3.8%) | 5.1% to 5.4% (4.5%) | 3.5% to 3.6% (3.4%) | 2.1% | 2.7% | 5.4% | 3.6% |

*FIG. 22*

| Size range | Inactive SLE | Active SLE |
| --- | --- | --- |
| Short (0-250 bp) | 97.4% to 95.2% (-2.3%) | 97.2% to 95.8% (-1.4%) |
| Long (>250 bp) | 2.6% to 4.8% (88.0%) | 2.8% to 4.2% (49.3%) |
| 0-115 bp | 4.3% to 3.7% (-14.5%) | 11.8% to 11.3% (-4.3%) |
| >200 bp | 5.4% to 7.6% (46.8%) | 7.8% to 9.4% (21.7%) |

*FIG. 23*

CELL-FREE DNA QUALITY

CROSS-REFERENCES TO RELATED APPLICATIONS

The present application claims priority to and is a non-provisional of U.S. Provisional Application No. 62/748,767, entitled "IMPROVING CELL-FREE DNA QUALITY," filed on Oct. 22, 2018, the disclosure of which is incorporated by reference in its entirety for all purposes.

BACKGROUND

The detection of circulating cell-free fetal DNA (cfDNA) in maternal plasma has been increasingly adopted in non-invasive prenatal testing (NIPT) since its discovery in 1997.[1] cfDNA molecules of different origins have characteristic size distributions, with the most abundant 166-bp peak for maternal cfDNA molecules and a relatively prominent 143-bp peak for the fetal cfDNA molecules.[2] Size differences between fetal and maternal cfDNA have been used for the development of size-based NIPT.[2-4] Fetal DNA fraction is a major contributor for successful NIPT. Estimation of the fetal DNA fraction has been shown to be achievable, even with shallow sequencing depths.[5] Despite the international adoption of NIPT, a number of issues need further refinements, including false-negative and no-call results.[6] To these ends, a number of approaches have been explored to enrich fetal DNA from maternal plasma.[3,7,8] However, all of these methods have their disadvantages.

DNA damage, for example, single-strand nicks, exists and distributes throughout cfDNA molecules.[9,10] Apoptosis, which is believed to be one of the major mechanisms of cfDNA production, involves DNA fragmentation during karyorrhexis, followed by the formation and production of apoptotic bodies.[11-13] Commonly used sequencing library preparation methods employ the repair of DNA ends only, leading to the loss of damaged cfDNA fragments such as those with single-strand nicks.[10,14,15] Therefore, the detection of these damaged cfDNA molecules by the current paired-end massively parallel sequencing (MPS) platforms is challenging.

Systems and methods described below address DNA damage and other DNA issues. The quality of cell-free DNA for sequencing library preparation and/or other analysis may improve as a result of the systems and methods.

BRIEF SUMMARY

Embodiments of the present invention provide for improving the quality of cell-free DNA for analysis. Cell-free DNA may include DNA with defects that do not allow for analysis of those DNA with techniques such as sequencing and targeted capture enrichment. These defects may be defects within the strands of the DNA and not present at the ends of the DNA. Embodiments of the present invention repair these intrastrand defects in cell-free DNA. The repair of the defects in cell-free DNA may then allow for these repaired cell-free DNA to be analyzed by techniques, including sequencing and targeted capture enrichment.

Repairing cell-free DNA may increase the amount of DNA available for analysis and/or may allow for longer DNA fragments to be analyzed. Because more DNA without defects would be available after repair, analysis of DNA would be possible in some cases where the amount of DNA without defects was not sufficient for analysis or sufficient to allow for a statistically significant conclusion from the analysis. Additionally, longer DNA fragments may be more prone to defects repairable by techniques described herein. Repairing the defects may then allow for more longer DNA fragments to be analyzed. Long DNA fragments allow for analysis of disorders and conditions with sequence patterns are repeated over a minimum number of loci.

The pattern or severity of defects in the cell-free DNA may be an indication of a disorder or a condition. A certain disorder, for example, may have more defects in cell-free DNA than defects in cell-free DNA from a subject without the disorder. The number or pattern of defects can then be used to provide a classification of whether an individual has a disorder.

A better understanding of the nature and advantages of embodiments of the present invention may be gained with reference to the following detailed description and the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-3D show changes in size profile as a result of repair on a logarithmic scale according to embodiments of the present invention.

FIG. 13 shows a table of size distributions of short (0-250 bp) and long (>250 bp) cfDNA fragments from maternal plasma of pregnant women carrying a fetus with trisomy 21 according to embodiments of the present invention.

FIG. 14A is a graph with a log scale, and FIG. 14B is a graph with a linear scale.

FIG. 18 shows a table of the SLE patients from whom cfDNA was extracted according to embodiments of the present invention.

FIG. 21A is a graph with a log scale, and FIG. 21B is a graph with a linear scale.

FIG. 22 shows a table of the percentage changes and percentages in different size ranges of DNA fragments in active and inactive SLE patients after cfDNA repair according to embodiments of the present invention.

FIG. 23 shows a table of changes in different size ranges of DNA fragments in active and inactive SLE patients after cfDNA repair according to embodiments of the present invention.

TERMS

Figure 1A:
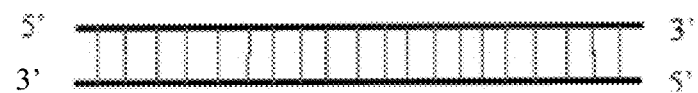
FIGS. 1A, 1B, and 1C show different defect modes affecting DNA according to embodiments of the present invention.
Figure 1A:
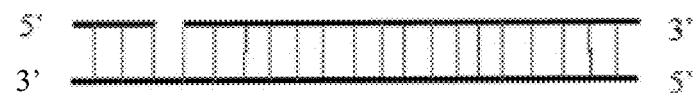
Figure 1A:
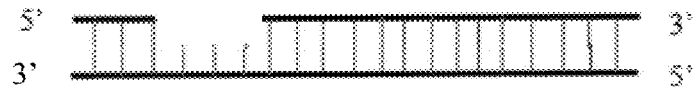
Figure 1A:

As used herein, the term "locus" or its plural form "loci" is a location or address of any length of nucleotides (or base pairs) which has a variation across genomes. A "sequence read" refers to a string of nucleotides sequenced from any part or all of a nucleic acid molecule. For example, a sequence read may be a short string of nucleotides (e.g., 20-150) sequenced from a nucleic acid fragment, a short string of nucleotides at one or both ends of a nucleic acid fragment, or the sequencing of the entire nucleic acid fragment that exists in the biological sample. A sequence read may be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification.

A "tissue" corresponds to a group of cells that group together as a functional unit. More than one type of cells can be found in a single tissue. Different types of tissue may consist of different types of cells (e.g., hepatocytes, alveolar cells or blood cells), but also may correspond to tissue from different organisms (mother vs. fetus) or to healthy cells vs. cells showing a disorder.

A "biological sample" refers to any sample that is taken from a subject (e.g., a human, such as a pregnant woman, a person with a disorder, or a person suspected of having a disorder, an organ transplant recipient or a subject suspected of having a disease process involving an organ (e.g., the heart in myocardial infarction, or the brain in stroke, or the hematopoietic system in anemia) and contains one or more nucleic acid molecule(s) of interest. The biological sample can be a bodily fluid, such as blood, plasma, serum, urine, vaginal fluid, fluid from a hydrocele (e.g. of the testis), vaginal flushing fluids, pleural fluid, ascitic fluid, cerebrospinal fluid, saliva, sweat, tears, sputum, bronchoalveolar lavage fluid, discharge fluid from the nipple, aspiration fluid from different parts of the body (e.g. thyroid, breast), etc. Stool samples can also be used. In various embodiments, the majority of DNA in a biological sample that has been enriched for cell-free DNA (e.g., a plasma sample obtained via a centrifugation protocol) can be cell-free, e.g., greater than 50%, 60%, 70%, 80%, 90%, 95%, or 99% of the DNA can be cell-free. The centrifugation protocol can include, for example, 3,000 g×10 minutes, obtaining the fluid part, and re-centrifuging at for example, 30,000 g for another 10 minutes to remove residual cells. The cell-free DNA in a sample can be derived from cells of various tissues, and thus the sample may include a mixture of cell-free DNA.

"Nucleic acid" may refer to deoxyribonucleotides or ribonucleotides and polymers thereof in either single- or double-stranded form. The term may encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs may include, without limitation, phosphorothioates, phosphoramidites, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The term "nucleotide," in addition to referring to the naturally occurring ribonucleotide or deoxyribonucleotide monomers, may be understood to refer to related structural variants thereof, including derivatives and analogs, that are functionally equivalent with respect to the particular context in which the nucleotide is being used (e.g., hybridization to a complementary base), unless the context clearly indicates otherwise.

A "sequence read" refers to a string of nucleotides sequenced from any part or all of a nucleic acid molecule. For example, a sequence read may be the entire nucleic acid fragment that exists in the biological sample. A sequence read may be obtained from a single-molecule sequencing. "Single-molecule sequencing" refers to sequencing of a single template DNA molecule to obtain a sequence read without the need to interpret base sequence information from clonal copies of a template DNA molecule. The single-molecule sequencing may sequence the entire molecule or only part of the DNA molecule. A majority of the DNA molecule may be sequenced, e.g., greater than 50%, 55%, 60%, 65%, 70%, 75%, 80%, 85%, 90%, 95%, or 99%.

A "classification" refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1). The term "cutoff" and "threshold" refer to a predetermined number used in an operation. For example, a cutoff size can refer to a size above which fragments are excluded. A threshold value may be a value above or below which a particular classification applies. Either of these terms can be used in either of these contexts.

The term "size profile" generally relates to the sizes of DNA fragments in a biological sample. A size profile may be a histogram that provides a distribution of an amount of DNA fragments at a variety of sizes. Various statistical parameters (also referred to as size parameters or just parameter) can be used to distinguish one size profile to another. One parameter is the percentage of DNA fragment of a particular size or range of sizes relative to all DNA fragments or relative to DNA fragments of another size or range.

The term "cutoff value" or amount as used in this disclosure means a numerical value or amount that is used to arbitrate between two or more states of classification for a biological sample—for example, the presence or absence of a genetic sequence that is associated or linked with a particular phenotypic condition or disease, or a susceptibility to a phenotypic condition or disease. For example, if a parameter is greater than the cutoff value, a first classification of the quantitative data is made, or if the parameter is less than the cutoff value, a different classification of the quantitative data is made.

DETAILED DESCRIPTION

Cell-free DNA in maternal plasma and in other biological samples can be used for diagnostic and other purposes. However, cell-free DNA molecules may be damaged within the strands of a double-stranded nucleic acid molecule. The damage may result from causes to the biological sample (e.g., heat, agitation, ultraviolet light) or internal to the biological sample (e.g., errors in replication). Conventional assays, including sequencing and using targeted probes, may be unable to determine reads from these double-stranded nucleic acid molecules with intrastrand defects. As a result, the damaged cell-free DNA may not provide any information that could be used for analysis. Embodiments of the present invention may allow for more information and more accurate information to be produced from cell-free DNA in a biological sample.

FIG. 1A shows intact double-stranded DNA and intrastrand defects. Intact dsDNA shows that there are no defects in the sugar phosphate backbone or in the base pairs. Nicked DNA shows that the backbone between two adjacent nucleotides is missing. Specifically, no phosphodiester bond is present between adjacent nucleotides. Gapped DNA is when one or more nucleotides of a strand are missing. Abasic DNA is when one or more bases are missing, with the backbone unaffected.

Figure 1B:
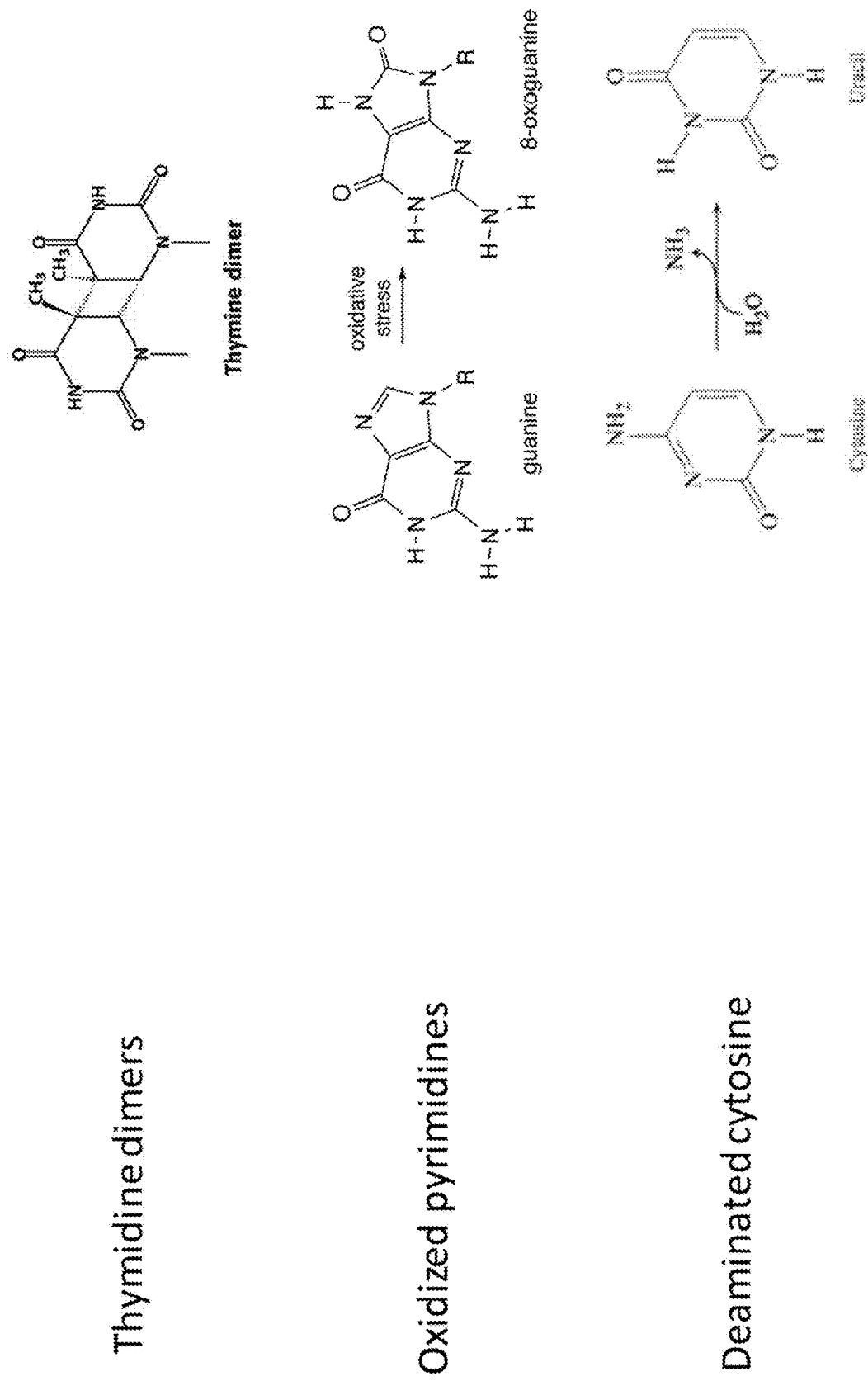

FIG. 1B shows other defects that may affect the bases within the DNA. Thymidine dimers may form when adjacent thymine bases bond to each other through carbon-carbon double bonds, often in the presence of ultraviolet radiation. As a result, the thymine base pair bonding with the adenine is broken. Oxidized pyrimidines include when guanine is oxidized to form 8-oxoguanine. Deaminated cytosine includes when cytosine loses an amine group and forms uracil.

Figure 1C:
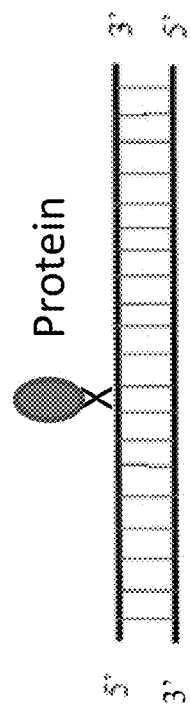

FIG. 1C shows a DNA-protein crosslinking defect. The double-stranded DNA crosslinks with the protein. DNA-protein crosslinking defects may be fixed through reverse crosslinking, which may be achieved by adding high concentrations of sodium chloride.

To salvage the damaged DNA molecules, we hypothesized that a repair mixture using Taq DNA polymerase, Bst DNA polymerase, Taq DNA ligase, endonuclease VIII, endonuclease IV, T4 endonuclease V (PDG), 8-oxoguanine glycosylase (FPG), or uracil-DNA glycosylase (UDG), could be used to repair cfDNA in maternal plasma. An example of a repair mixture is PreCR Repair Mix. Repaired maternal plasma DNA with higher DNA integrity might enhance the success for downstream analysis. Due to the fact that fetal-derived cfDNA molecules are shorter and more fragmented than the maternal ones,[2,16] we proposed that fetal cfDNA molecules possess more DNA damages. By repairing these damaged fetal cfDNA molecules, the fetal DNA fraction may be enriched.

In this study, we applied repair treatment on cfDNA from maternal plasma of first- and third-trimester pregnancies. We studied and compared the size profiles and fetal DNA fractions between repaired cfDNA samples and their sham controls. We would also discuss the potential impact of repair treatment on the performance of NIPT and on the performance of assessing whether an individual has a disorder.

I. DNA Repair Study with Maternal Plasma

DNA fragments from maternal plasma were treated to repair intrastrand defects such as those in FIG. 1A. The repaired DNA fragments were analyzed for their effect on short and long fragments and fetal and maternal DNA.

A. Materials and Methods

1. Subjects, Sample Collection and DNA Extraction

This study was approved by the institutional research ethics committee. Pregnant women with singleton male fetuses were recruited from the Department of Obstetrics and Gynaecology, Prince of Wales Hospital, Hong Kong with informed consent. Plasma was isolated from 20 mL of EDTA-anticoagulated maternal peripheral blood as previously described.[2] For third trimester cases, 1 cm$^3$ of placental tissue was dissected freshly after delivery from a region 2 cm deep and 5 cm away from the umbilical cord insertion. For first trimester cases, chorionic villus samples (CVS) were obtained. Plasma and buffy coat genomic DNA were extracted using the QIAamp DSP DNA Blood Mini Kit (Qiagen) and QIAamp DNA Blood Mini Kit (Qiagen), respectively, and quantified by Qubit 3.0 (Invitrogen). Placental DNA and chorionic villus DNA were extracted using the QIAamp DNA Mini Kit (Qiagen) according to manufacturer's protocols.

2. Plasma cfDNA Repair and Sequencing Library Preparation 10 ng of extracted plasma DNA was subjected for DNA repair, using the PreCR Repair Mix (New England Biolabs). A sham control was done in parallel with the same amount of DNA input. The sham control includes the reaction buffer but without the active enzymes. In this case, the sham control does not include the active enzymes of the PreCR Repair Mix. A sham control is preferred to a normal control (i.e., no reaction buffers) by removing the potential bias caused from the reaction buffers. Briefly, 10 ng extracted DNA is mixed with 1× ThermoPol Buffer, 100 µM dNTPs, 1×NAD$^+$, and H$_2$O in a 49 µl reaction, followed by addition of either 1 µl of H$_2$O (sham) or PreCR Repair Mix (repair). Sham- or repaired-treated plasma DNA were purified by a MinElute Reaction Cleanup Kit (Qiagen) to remove residual enzymes and reagents, followed by paired-end sequencing library preparations. Double-stranded DNA (dsDNA) libraries were generated as previously described.[17] Adaptor-ligation single-stranded DNA (LIG-ssDNA) libraries were generated by the Accel-NGS 1S Plus DNA Library Kit (SWIFT Biosciences). Libraries were quantified by Qubit dsDNA HS Assay kit (Thermo Fisher Scientific) and real-time quantitative PCR (KAPA Library Quantification kit) on a Light-Cycler 96 System (Roche). The size profiles of the sequencing libraries were examined by Agilent 4200 TapeStation System with High Sensitivity D1000 ScreenTape (Agilent) to confirm successful library preparation before sequencing.

3. Targeted Capture Enrichment and Massively Parallel Sequencing

Targeted capture of sequencing libraries was performed as described.[18] The capture probes (Roche Nimblegen) predominantly targeted sequences on Chr6 and ChrY. An average sequencing depth of 152× per base (ranging from 82× to 210×) was obtained. Target capture enrichment efficiency was validated by quantitative real-time PCR. All libraries were sequenced with a paired-end (PE) format of 75 bp×2 on a NextSeq 500 system (Illumina). Adaptor sequences and low quality bases (i.e., quality score<5) were removed and sequencing reads were aligned to the non-repeat-masked human reference genome (hg19) using the Short Oligonucleotide Alignment Program 2 (SOAP2).[19] Up to two nucleotide mismatches, but not indels, were allowed for each member of the pair-end reads.

4. Single Molecule Real-Time (SMRT) Sequencing

The pre-target captured sequencing libraries with Illumina format adapters were pooled and subjected to SMRT sequencing template construction using a SMRTbell Template Prep Kit 1.0-SPv3 (Pacific Biosciences). The post-target captured Illumina sequencing libraries were similarly pooled and further subjected to SMRT sequencing library construction. The amplicon template preparation and sequencing protocol was used, with minor modifications: DNA was purified with 1.8× AMPure PB beads, and library size was estimated using a TapeStation instrument (Agilent). Sequencing primer annealing and polymerase binding conditions were calculated with the SMRT Link v5.1.0 software (Pacific Biosciences). Briefly, sequencing primer v3 was annealed to the sequencing template, then polymerase was bound to templates using a Sequel Binding and Internal Control Kit 2.1 (Pacific Biosciences). Sequencing was performed on a Sequel SMRT Cell 1M v2. Sequencing movies were collected on the Sequel system for 10 hours with a Sequel sequencing kit 2.1 (Pacific Biosciences).

5. Microarray Genotyping and Single Nucleotide Polymorphism (SNP) Identification Fetal and maternal genomic DNA samples were genotyped with the Infinium Omni2.5-8 V1.3 Kit and the iScan system (Illumina). SNPs were called by the Birdseed v2 algorithm.[20] The genotypes of the CVS and placentas were compared with those of the mothers to identify the fetal-specific and maternal specific SNP alleles. A SNP was considered as fetal-specific if it was homozygous in the mother and heterozygous in the fetus, and the reverse for maternal-specific SNPs. The fetal DNA fractions were deduced as described.[2] In the size-fractionated fetal fraction analysis, fetal DNA fragments were divided into 10-bp bins as previously described,[17] with modified size range of analysis. Error rates were deduced by the following equation:

$$Err\ \% = \frac{\#\ \text{non-}iSCAN\ \text{genotype allele}}{\#\ \text{total}\ SNP\ \text{covering allele}}$$

For mouse plasma cfDNA repair, total blood samples from two wildtype (WT) C57BL/6 mice were obtained via cardiac puncture at 10-12 weeks of age. The blood was collected into EDTA-containing collection tubes and plasma was isolated as previously described.[21] 10 ng of cfDNA input was subjected to sham- or repair treatment, before dsDNA sequencing library preparation.

B. Results

Results of repair treatment of cfDNA from maternal plasma show that repair treatment can recover a subset of long (>250 bp) cfDNA molecules of both fetal and maternal origins. The repair treatment gives a small but consistent fetal fraction increase. The results from analyzing repaired DNA show a relative higher enrichment of fetal long cfDNA molecules (>250 bp) after repair when compared to their maternal counterparts. The repair treatment was not found to alter DNA fidelity for downstream assays of molecular diagnostics. Repair of defects of double-stranded DNA was found to be more effective than repair of defects on single-stranded DNA.

1. Size Profile Characteristics of Sham or Repaired cfDNA from First- and Third-Trimester Maternal Plasma Samples We first studied if there was any size profile change of cfDNA in maternal plasma after sham or PreCR DNA repair treatment. Grossly, the size profiles between sham and repair groups did not show major differences within the range of 0-250 bp from sequencing. Both groups have a major peak size at around 166 bp and a series of peaks with 10-bp periodicity from 70-150 bp. However, we observed there was an average of 2.4% decrease (96.64% to 94.33%) of short (0-250 bp) cfDNA fragments and an average of 68.8% increase (3.36% to 5.67%) of long (251-600 bp) cfDNA fragments after repair treatment compared with their sham counterparts. Statistical analyses showed that both changes were significant (both p<0.01; Student's paired t-test). Student's paired t-tests and Wilcoxon Signed rank test were performed using IBM SPSS Statistics (IBM). A p-value of less than 0.05 was considered as statistically significant.

Figure 2A:
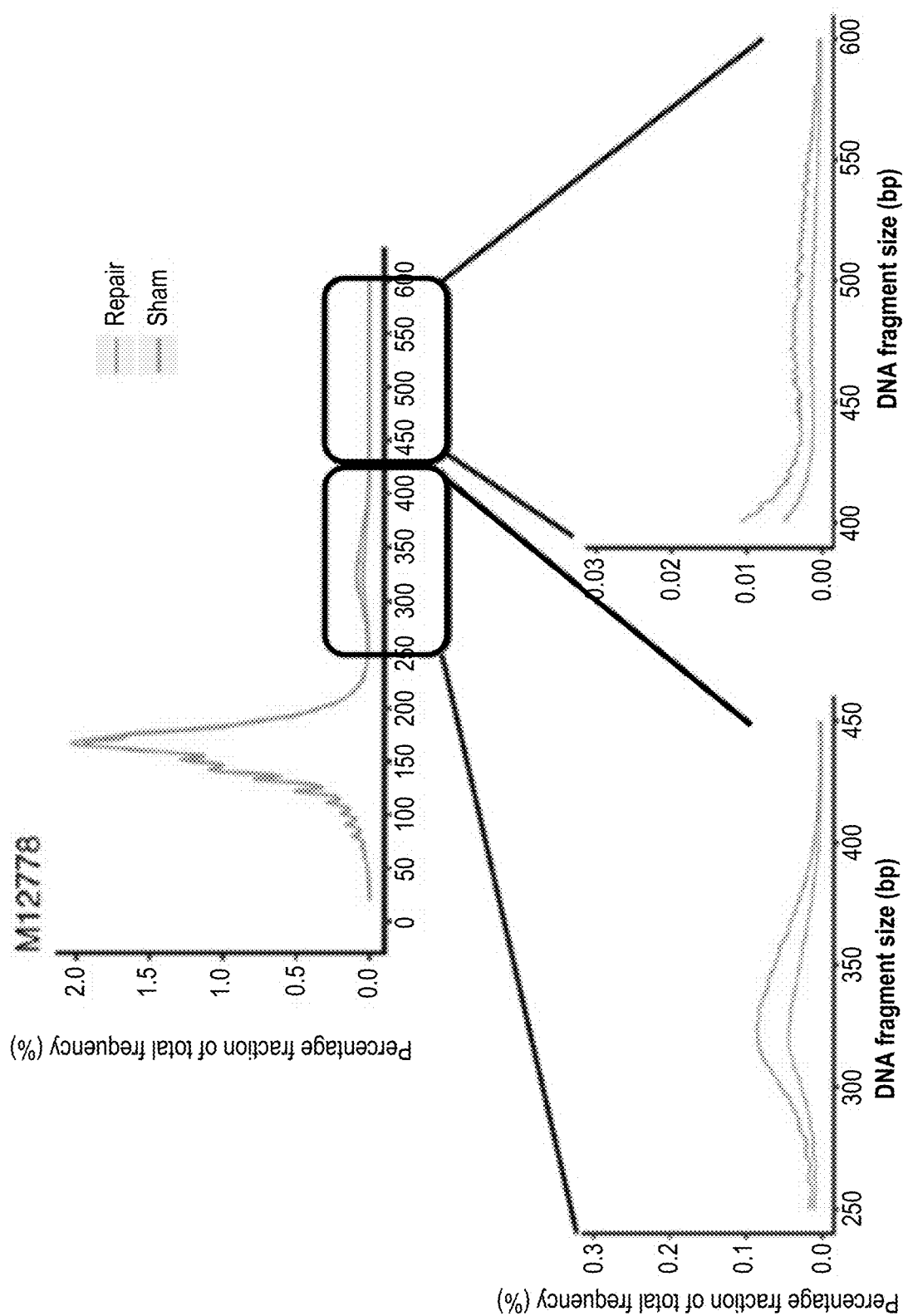
FIGS. 2A and 2B show repair changes in the size profile of cfDNA in maternal plasma according to embodiments of the present invention.

FIG. 2A shows the size profile comparison of sham and repaired cfDNA from a representative third trimester maternal plasma (M12778). Lower panels represent the magnified size profiles of long cfDNA molecules (black boxes). The figure shows an increase in the percentage fraction of fragments from 251-600 bp.

Figure 2B:
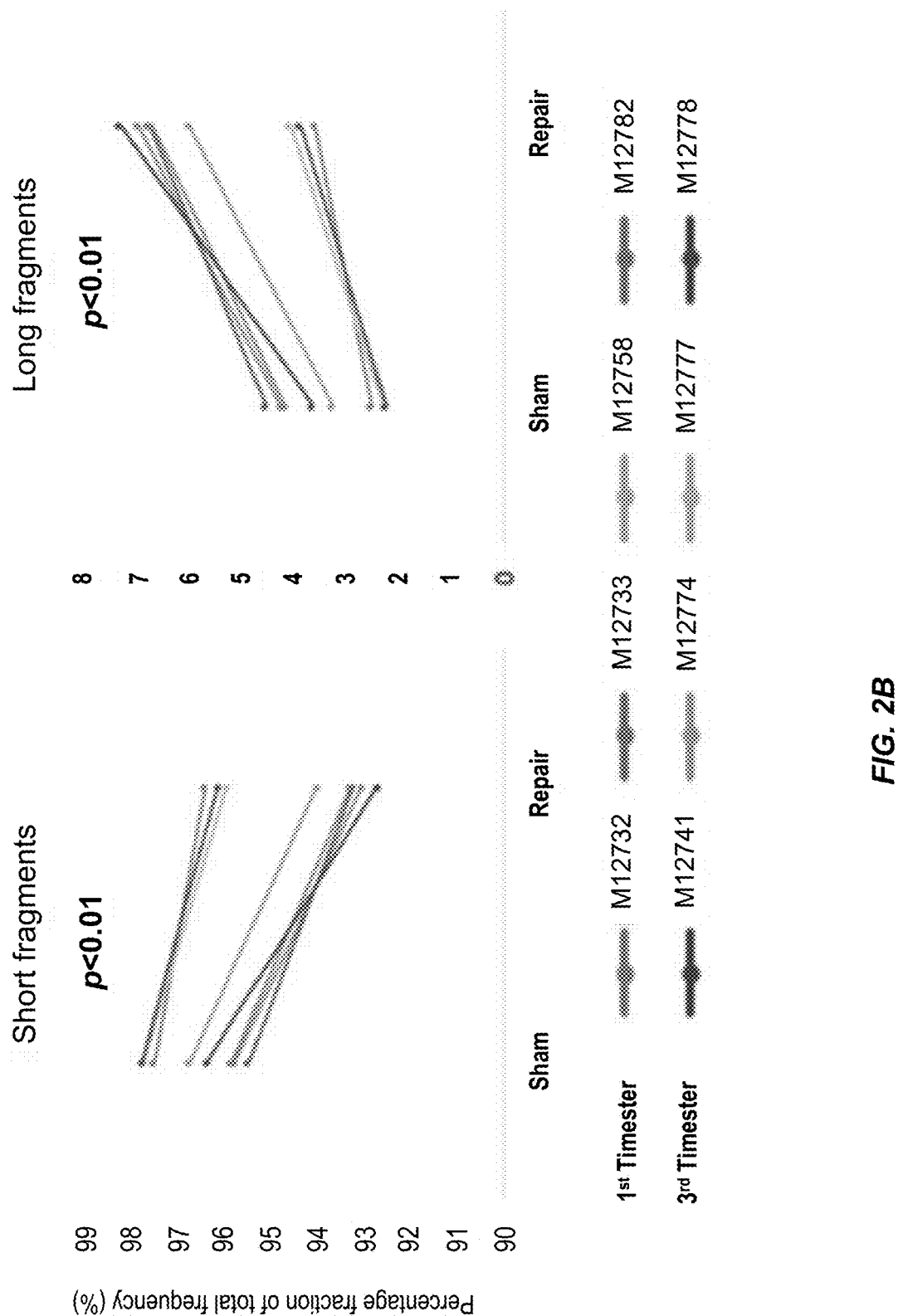

This trend was consistent in all subjects tested, including all maternal plasma samples from first and third trimesters (FIG. 2B). FIG. 2B shows quantification of cfDNA molecules with different sizes in first and third trimester maternal plasma after sham or repair treatment. There is a consistent decrease in the fraction of short (0-250 bp) and increase in the fraction of long (251-600 bp) cfDNA molecules after repair. Student's paired t-tests, p<0.01. The decrease in the percentage fraction of short molecules is observed to be a result of an increase in the number of long molecules after repair.

FIGS. 3A, 3B, 3C, and 3D present data from samples in FIGS. 2A and 2B on a logarithmic scale to better illustrate the increases in frequency of longer fragments. FIG. 3A shows a size profile comparison of sham and repaired cfDNA in log scale representation from a representative third trimester maternal plasma (M12778). FIGS. 3B-3D show averaged size profile comparison of sham and repaired cfDNA. FIG. 3B shows results from all cases. FIG. 3C shows the first trimester only. FIG. 3D shows the third trimester only. Enrichments in long (>250 bp) cfDNA molecules in repaired sequencing library is prominent in these figures.

Figure 4A:
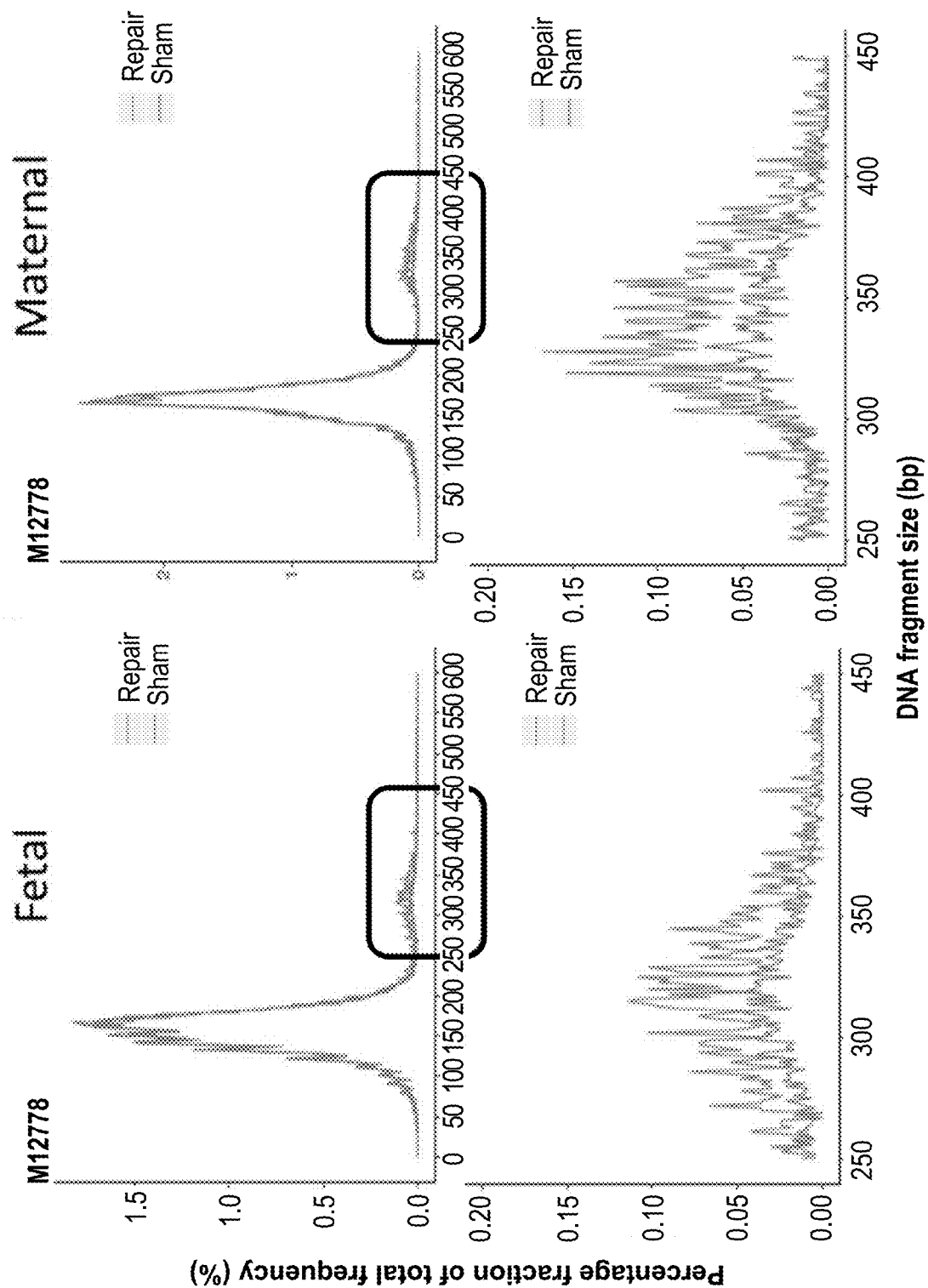
FIGS. 4A and 4B show treatment repairs cfDNA molecules of both fetal and maternal origins according to embodiments of the present invention.

We next asked if these size changes after repair treatment showed any relationship to the fetal or maternal origin of the cfDNA molecule. Using SNP-based genotypes, we separated the cfDNA fragments of all subjects into their respective maternal and fetal origins. cfDNA fragments carrying fetal or maternal-specific SNP alleles were separated and considered as fetal or maternal specific cfDNA molecules, respectively.[17] We observed a similar trend in repaired cfDNA molecules from both fetal and maternal origins (FIG. 4A). FIG. 4A shows the averaged size profile comparison of sham and repaired cfDNA from fetal origin on the left side and from maternal origin on the right side. Lower panels represent the magnified size profiles of long cfDNA molecules (black box).

Figure 4B:
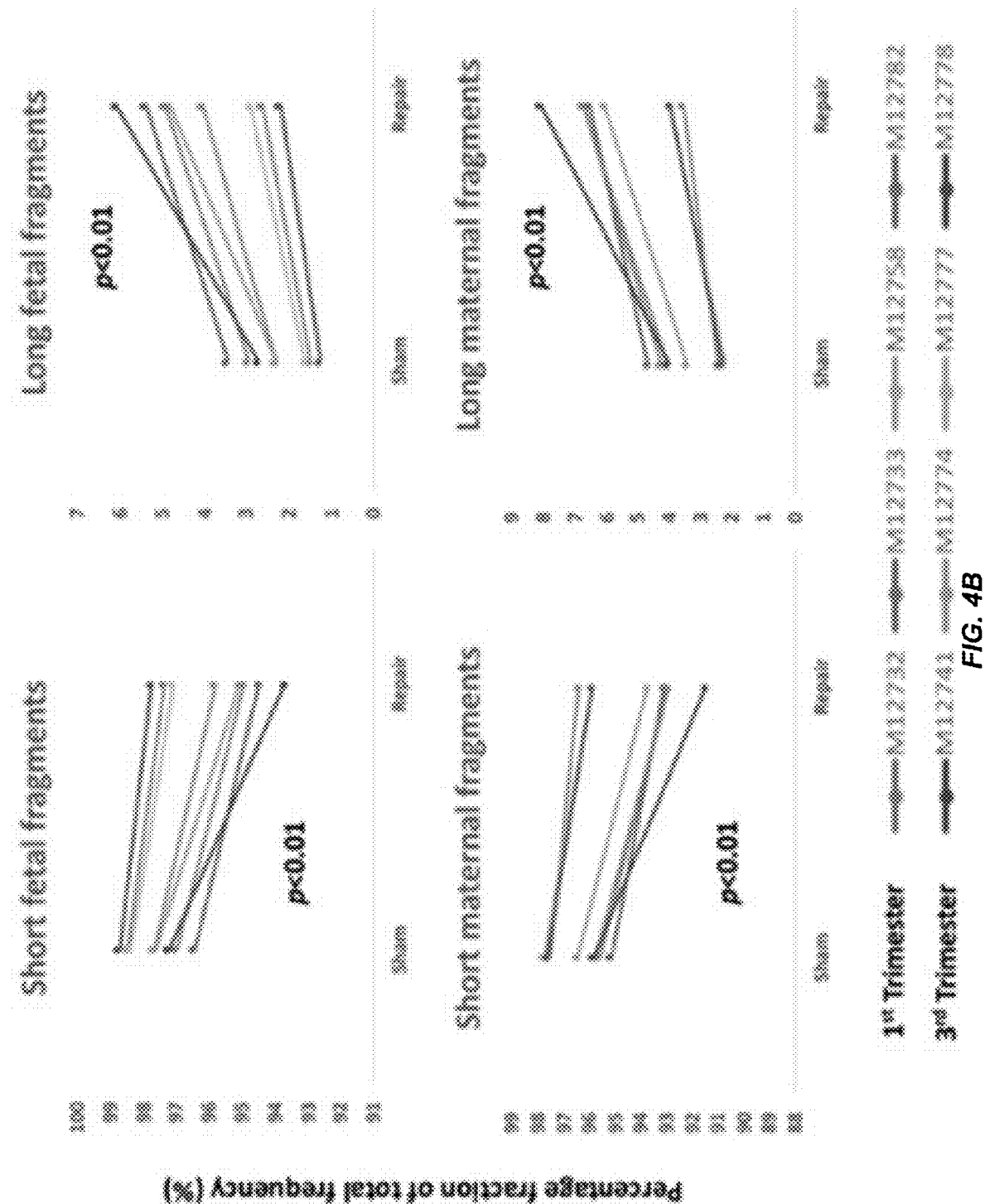

There was an average increase of 82.7% (2.26% to 4.13%) and 66.7% (3.42% to 5.7%) of long fetal and maternal cfDNA molecules after repair treatment, respectively (FIG. 4B). FIG. 4B shows quantification of short (0-250 bp) and long (251-600 bp) cfDNA molecules in fetal cfDNA on the left side and maternal cfDNA molecules on the right side. Data shown are from first and third trimester maternal plasma after sham or repair treatment. Statistical analyses showed that both increments were significant (both p<0.01; Student's paired t-test). These results suggested that there was a relative higher enrichment of fetal long cfDNA molecules after repair, when compared to their maternal counterparts.

Figure 5:
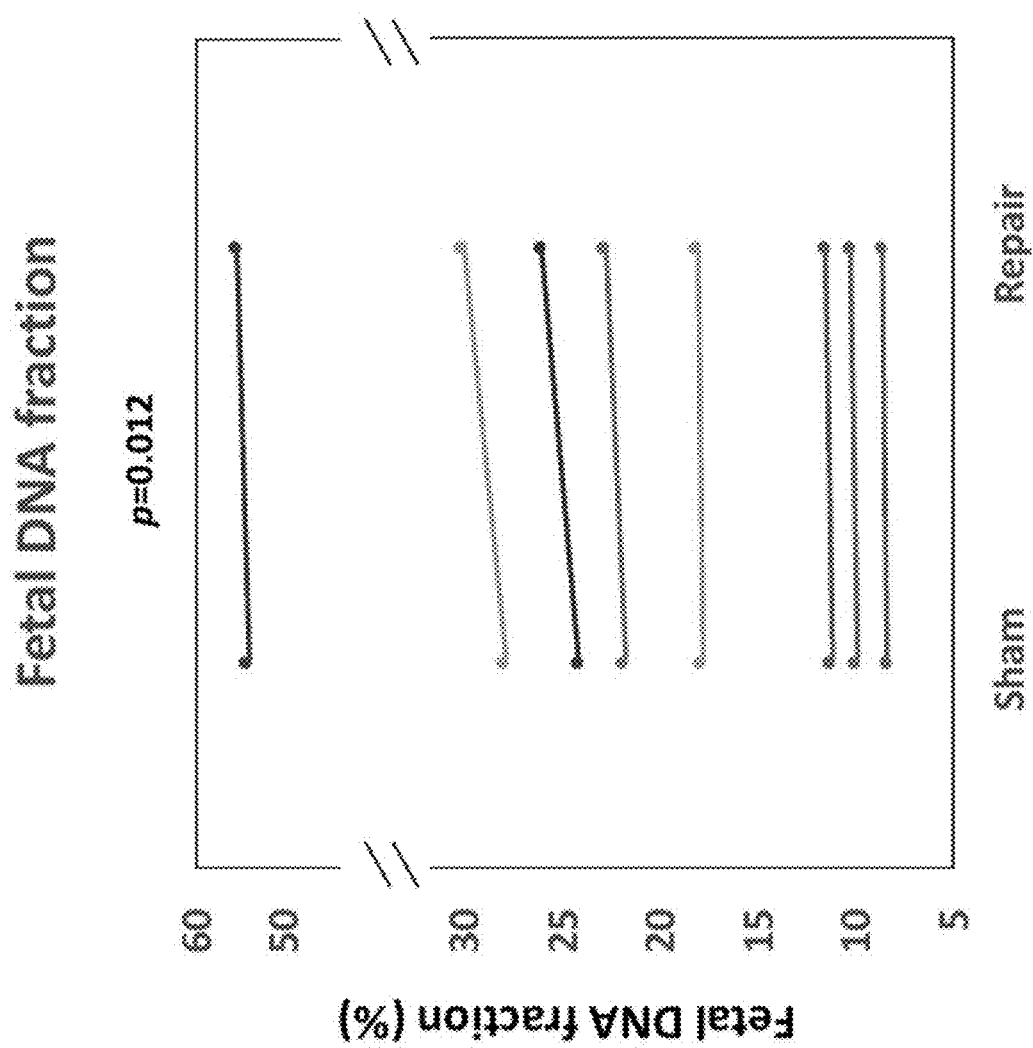
FIG. 5 shows fetal DNA fraction characterizations of repaired cfDNA according to embodiments of the present invention. Fetal DNA fraction of sham or repaired cfDNA from first and third trimester maternal plasma
Figure 6A:
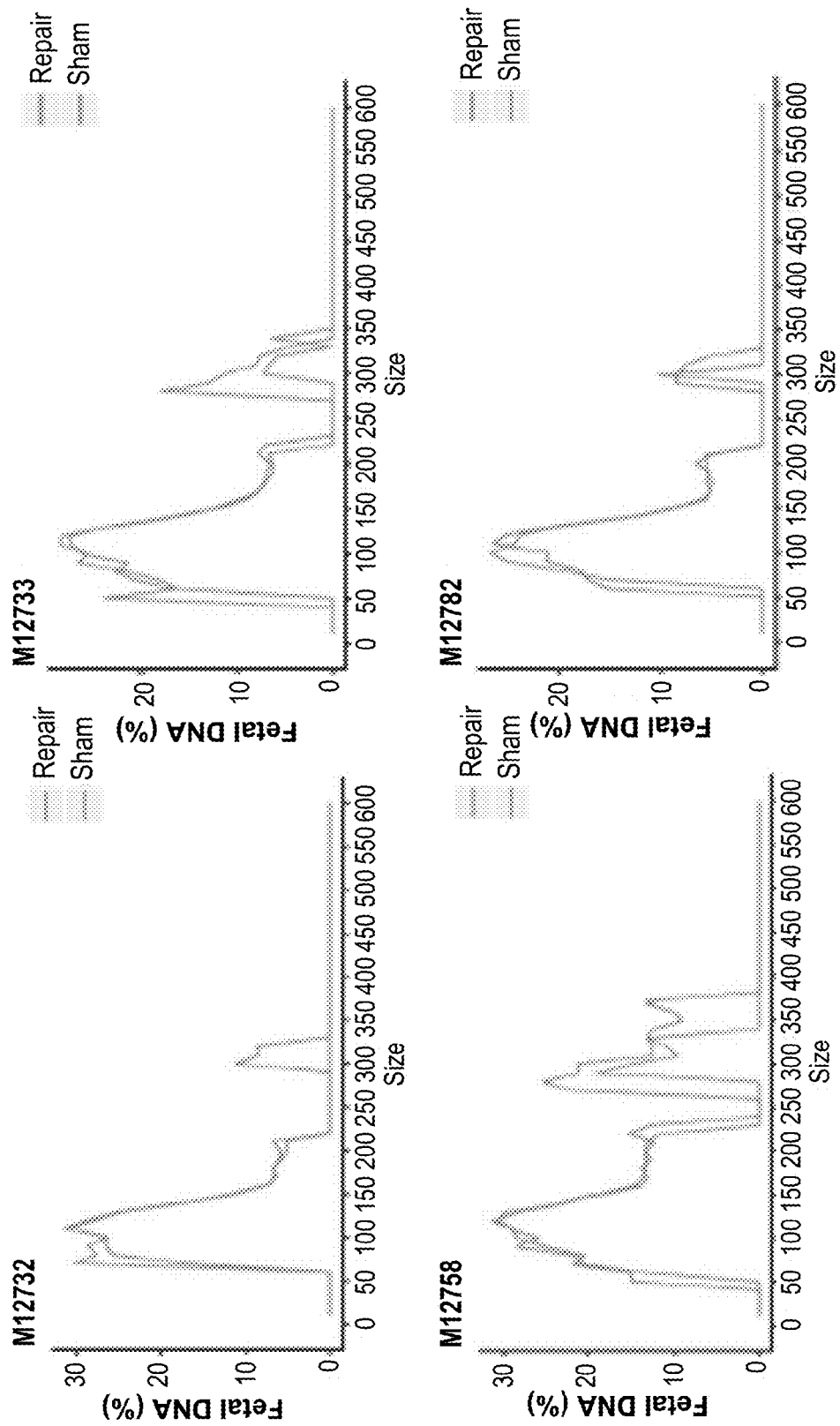
FIGS. 6A and 6B show size fractionated fetal DNA fractions of first and third trimester maternal plasma cfDNA after sham or repair treatment according to embodiments of the present invention.
Figure 6B:
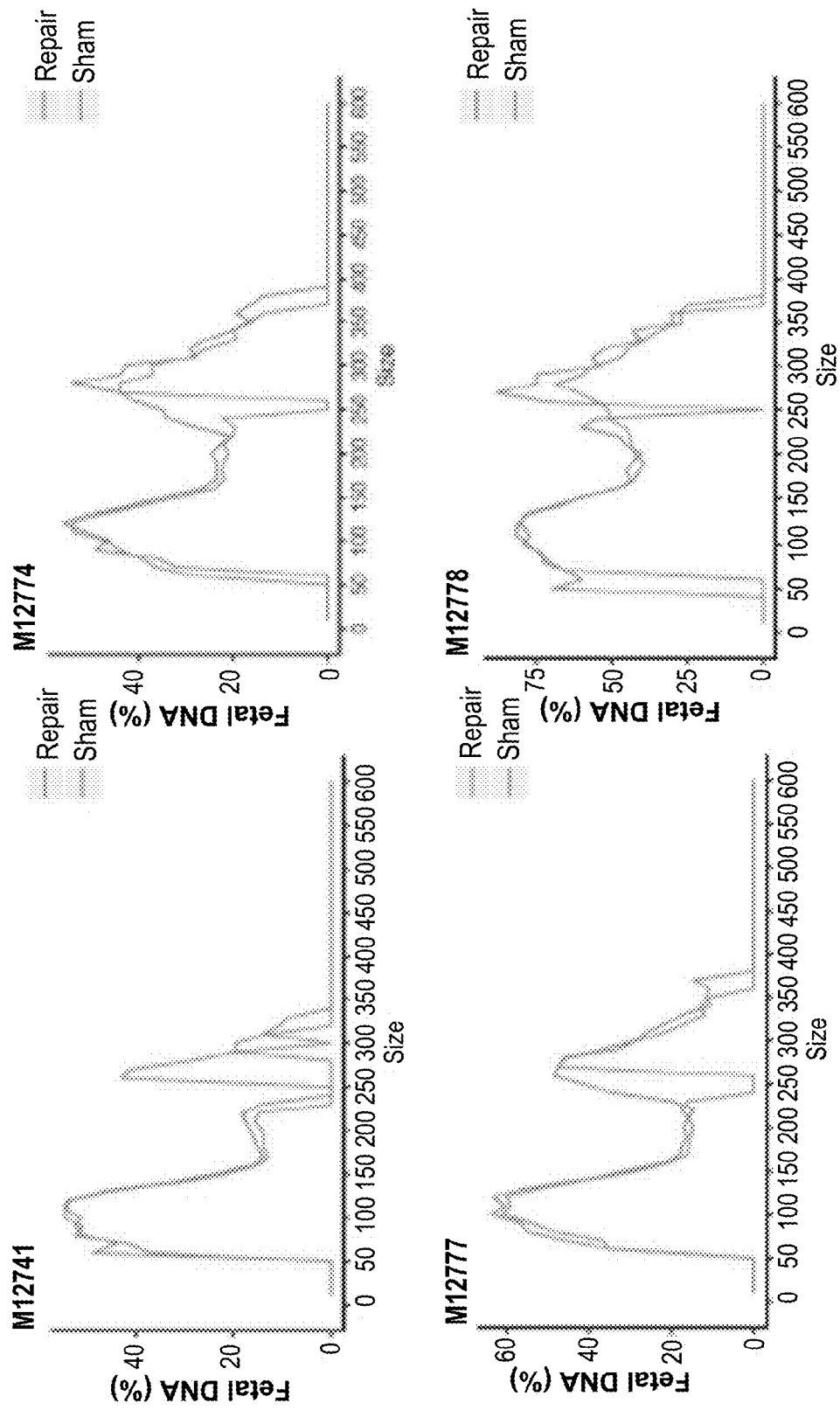

2. Fetal DNA Fraction Characteristics of Sham or Repaired cfDNA Libraries from First- and Third-Trimester Maternal Plasma Samples As the fetal DNA fraction is an important parameter for successful NIPT, an increase in this metric may benefit the sensitivity of NIPT, especially in cases with insufficient fetal contribution.[6] Therefore, we characterized and compared the overall fetal DNA fractions of maternal plasma from first and third trimester samples after sham and repair treatments. When pooling the data from all 8 samples together, we observed a consistent 4.31% increase of fetal DNA fraction (21.85% to 22.79%) after the repair treatment compared with their sham controls (FIG. 5). Repair treatment gives a small but consistent fetal fraction increase. Statistical analysis showed that such increment was significant (p=0.012; Wilcoxon Signed rank test). The source of such mild fetal DNA fraction increment may be from the newly repaired fetal long cfDNA molecules. To prove this, we applied size-fractionated fetal fraction analysis on both sham and repaired subjects. Fetal DNA fragments were divided into 10-bp bins, ranging from 0 bp to 600 bp. Fetal DNA fractions within each bin were then deduced separately.[17] We observed that such fetal DNA fraction increment was mainly contributed by the increase of fetal cfDNA molecules with the size of around 300 bp (FIGS. 6A and 6B). FIG. 4A shows first trimester maternal plasma. FIG. 6B shows third trimester maternal plasma. The fetal DNA fractions in long (approx. 300 bp) cfDNA molecules have a mild increase in repaired groups. Taken together, these results suggested that a higher enrichment of long fetal cfDNA molecules over their maternal counterparts in maternal plasma.

Figure 7:
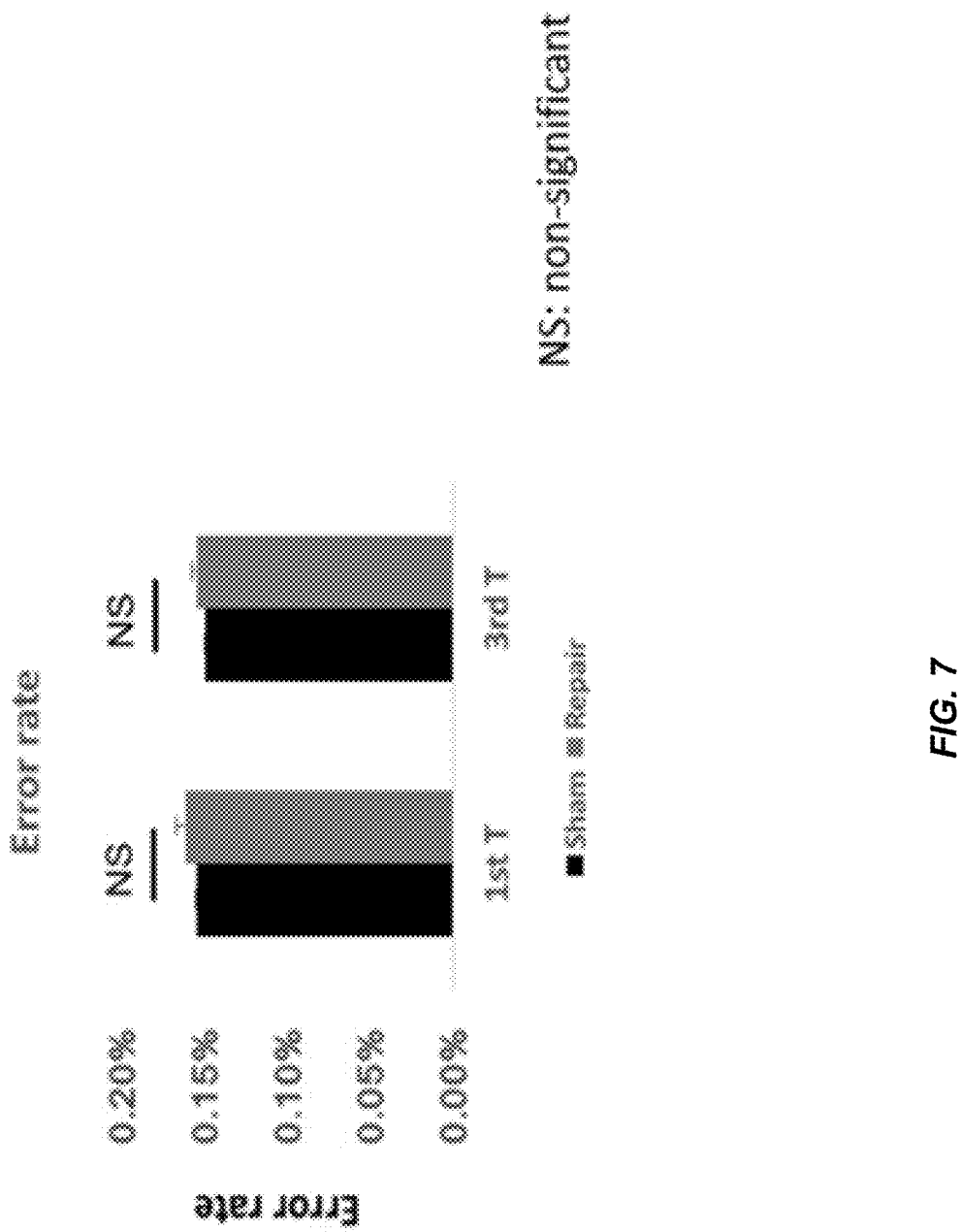
FIG. 7 shows an error rate comparison in between sham and repaired cfDNA from first and third trimester maternal plasma according to embodiments of the present invention.

DNA damage may be a pervasive cause of sequencing errors.[22] Novel errors can be introduced into cfDNA through multiple steps of the cfDNA repair protocol, such as strand displacement and correction of oxidized nucleotides. Therefore, we next checked if there was significant change of error rate in repaired libraries. No significant changes in error rate were observed in both first- and third-trimester cases (FIG. 7). This suggests that repair treatment does not alter DNA fidelity for downstream assays of molecular diagnostics.

Figure 8:
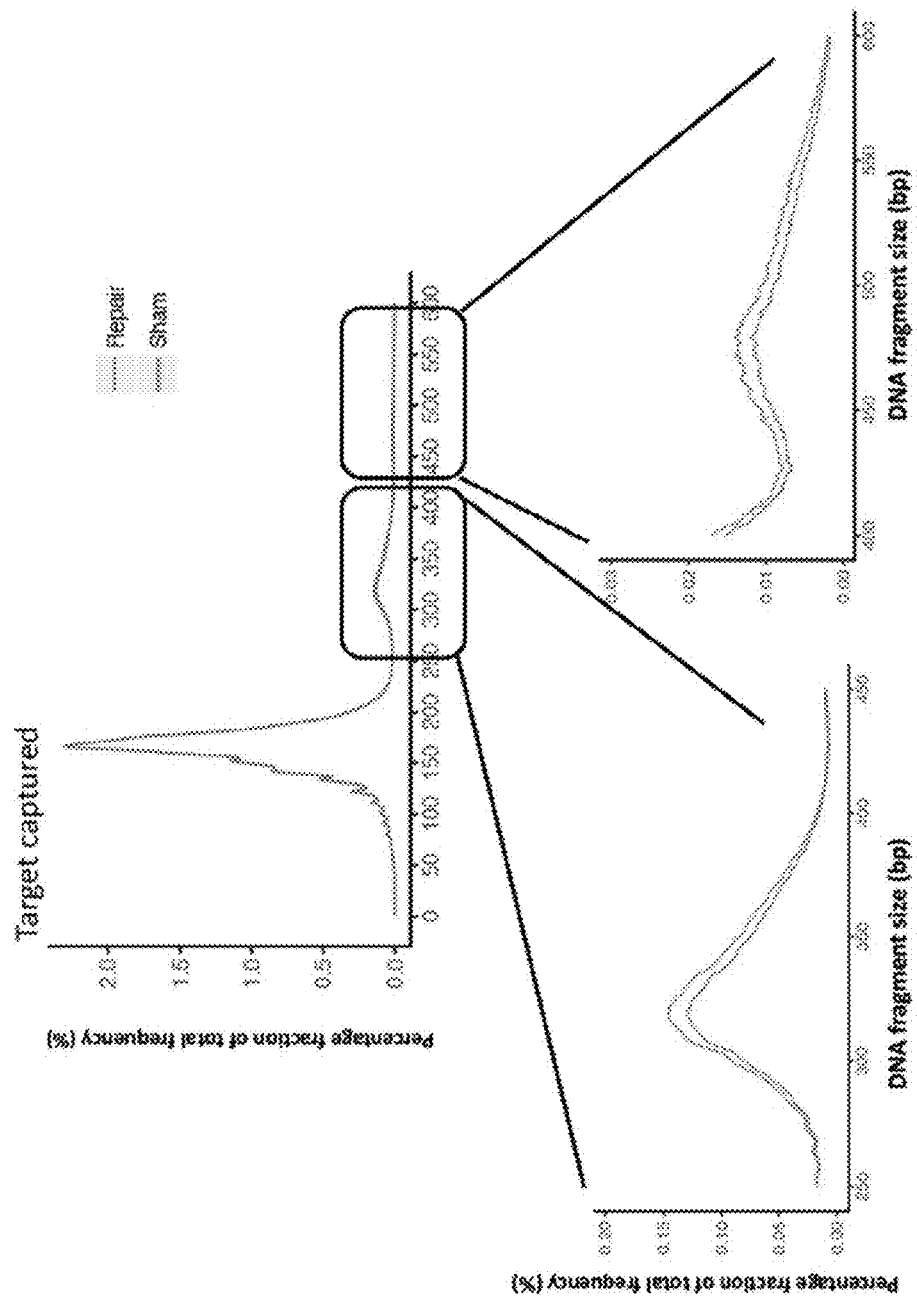
FIG. 8 shows an enrichment of long cfDNA molecules after repair treatment in target captured libraries according to embodiments of the present invention.

As fetal cfDNA molecules are the minority species in the maternal plasma, most of the data obtained from total maternal plasma cfDNA sequencing is dominated by maternally-derived cfDNA molecules. To obtain increased sequencing depth of fetal cfDNA molecules specifically, we used a target capture approach with probes hybridizing to sequences on Chr6 and ChrY.[18] We achieved an average sequencing depth of 152x per base for all sham and repaired samples. The observation from the targeted sequencing results was concordant with the non-target captured data, with a 13.6% enrichment (10.53% to 11.96%) of long cfDNA molecules between 250 bp and 600 bp in size, after repair treatment (FIG. 8). Targeted capture probes were hybridizing on sequences of Chr6 and ChrY. Averaged size profile comparison of sham and repaired cfDNA from pooled first and third trimester maternal plasma. Lower panels are the magnified size profiles of long cfDNA molecules (black boxes).

Figure 9A:
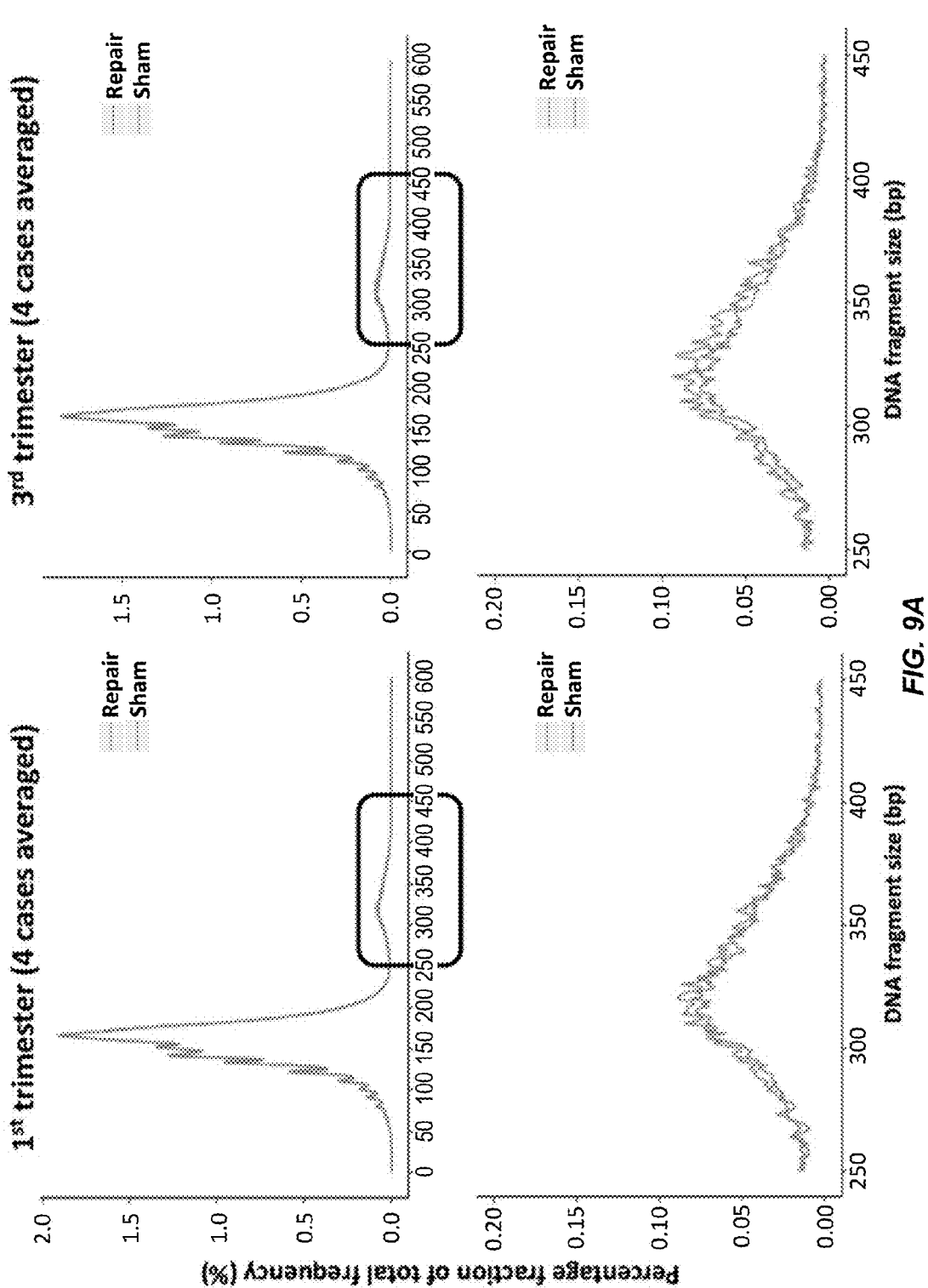
FIG. 9A shows increased sequencing depth of fetal cfDNA molecules by chromosome Y targeted capture according to embodiments of the present invention.
Figure 9B:
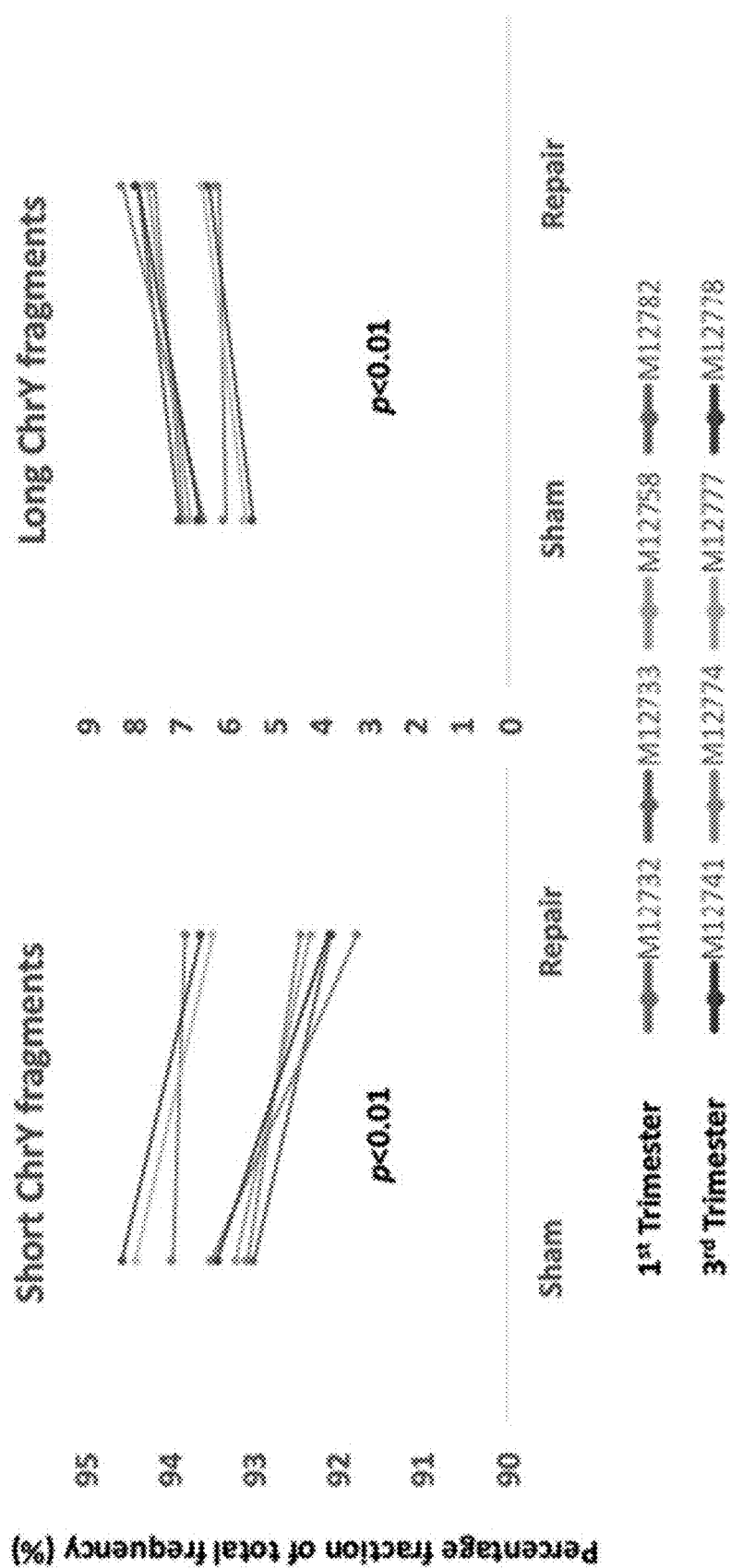
FIG. 9B shows quantification of short and long cfDNA chromosome Y molecules from first and third trimester maternal plasma after sham or repair treatment according to embodiments of the present invention.

When counting only the captured fetal cfDNA molecules, we observed an average of 14.8% enrichment (6.36% to 7.3%) of long chromosome Y cfDNA molecules after repair treatment over their sham counterparts (FIG. 9A). The top graphs show the averaged size profile comparison of sham and repaired cfDNA molecules from chromosome Y in the first trimester (left side) and third trimester (right side) maternal plasma. Lower panels represent the magnified size profiles of long cfDNA molecules (black box). FIG. 9B shows quantification of short (0-250 bp) and long (251-600 bp) cfDNA chromosome Y cfDNA molecules from first and third trimester maternal plasma after sham or repair treatment. Statistical analyses showed that such increment was significant (p<0.01; Student's paired t-test). Hence, we have demonstrated that repair treatment can recover a subset of long (>250 bp) cfDNA molecules in maternal plasma, both of fetal and maternal origins. The small but consistent increase of total fetal DNA fraction after repair was contributed by a higher enrichment of long fetal cfDNA molecules over their maternal counterparts.

Figure 10:
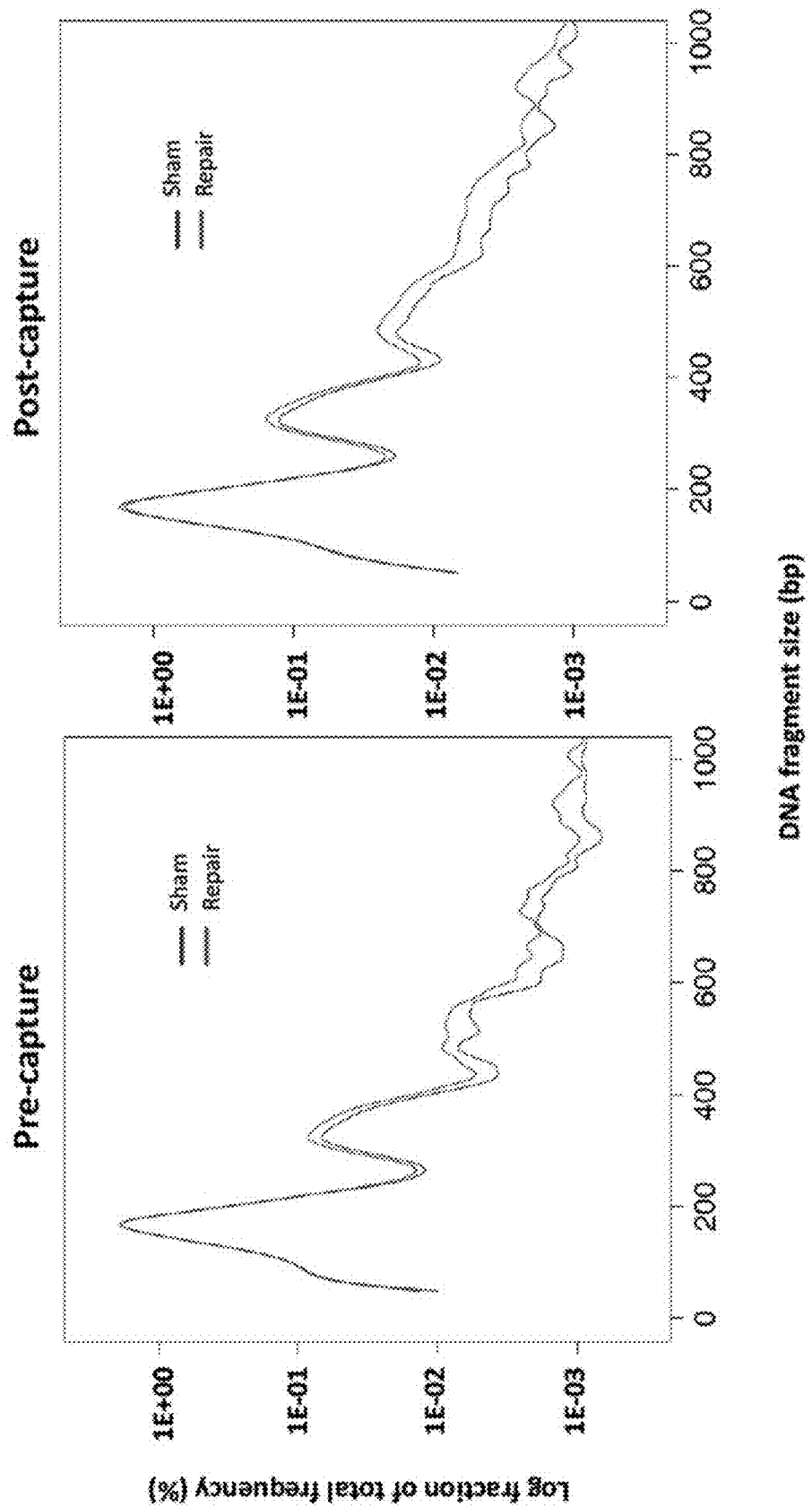
FIG. 10 shows that repair treatment enriches cfDNA molecules longer than 250 bp according to embodiments of the present invention.

3. Enrichment of cfDNA Molecules Longer than 250 bp from Maternal Plasma after Repair Treatment As the major size differences between sham and repair cfDNA resided on the cfDNA molecules longer than 250 bp, detection of such molecules by conventional NGS platforms, such as the Illumina platform, may not be preferred due to their short read lengths. A third generation sequencing platform from Pacific Biosciences, which employed the SMRT technology, can achieve sequencing read lengths exceeding 20 kb.[23] We hypothesized that using such a technology, we might improve our ability to observe the cfDNA molecules longer than 250 bp in the maternal plasma. Due to the limitation of minimum cfDNA input, we pooled all Illumina formatted pre- and post-target captured libraries and re-sequenced them on SMRT sequencing platform rather than directly sequencing DNA template. We expected an enrichment of long cfDNA molecules after repair treatment. Consistent with our sequencing data from the Illumina platform, we observed a respective 31.3% and 28.9% enrichment of cfDNA molecules longer than 250 bp in pooled libraries with or without target capture after repair treatment (FIG. 10). Pooled samples of pre- (left) and post- (right) target captured libraries showed an enrichment of cfDNA molecules longer than 250 bp after repair treatment, with more prominent enrichment for molecules longer than 400 bp. These enrichments were even more remarkable for cfDNA molecules longer than 600 bp (52% and 50.4% in pre- and post-target captured libraries, respectively). These data not only further confirmed our previous observations of long cfDNA molecule enrichment after repair treatment in paired-end, shorted-read sequencing platform, but also shed light on a population of long cfDNA molecules that had not been analyzed by massively parallel sequencing in previous studies.

4. Performance of cfDNA Repair in Different Library Preparation Protocols

Figure 11:
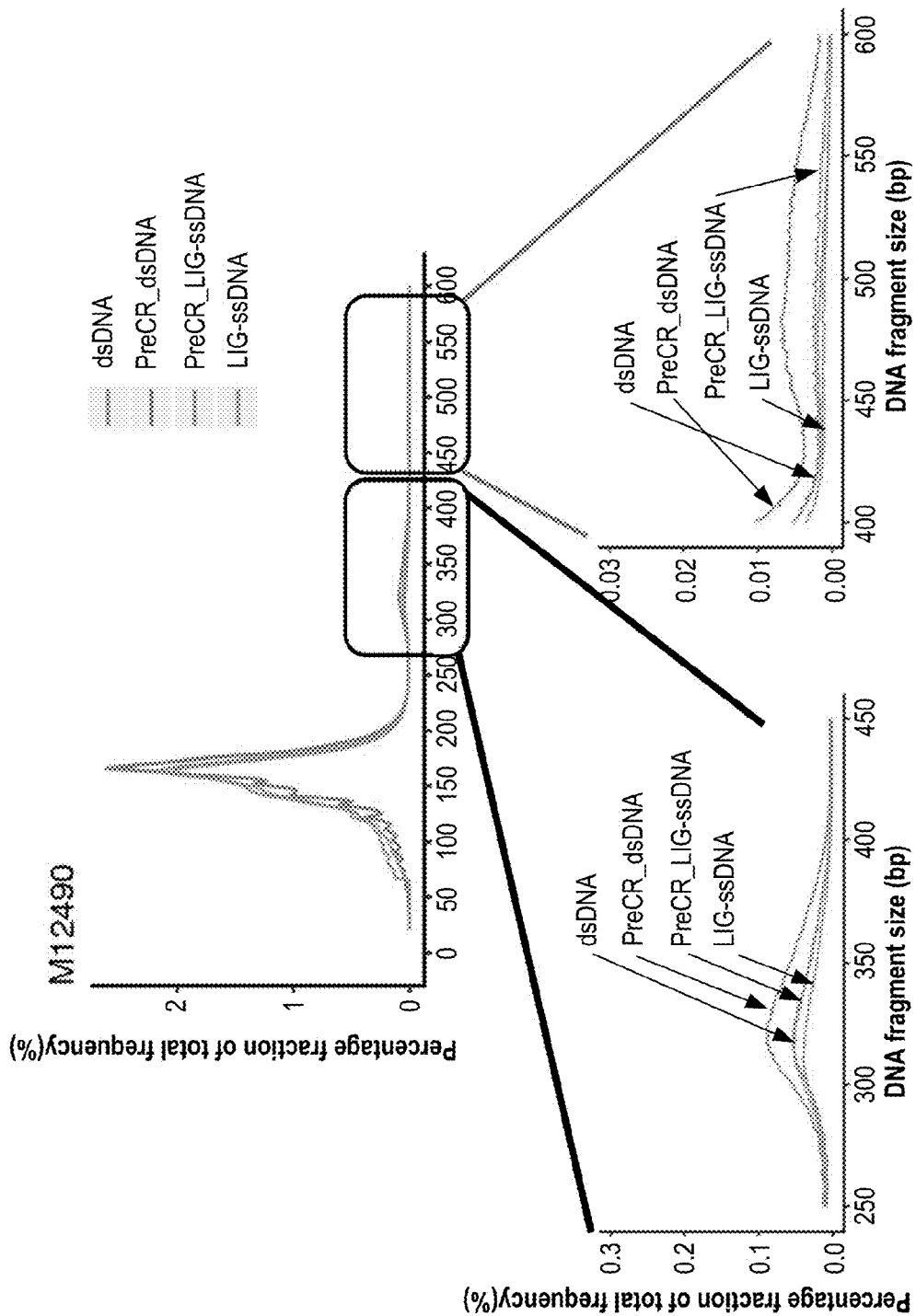
FIG. 11 shows size profiles comparison of libraries prepared by different protocols from M12490 third trimester maternal plasma DNA according to embodiments of the present invention.

Since we have shown previously that extra-short fragments were enriched by the single-stranded DNA (ssDNA) sequencing library preparation method,[17] it would be worthy to evaluate the cfDNA repair performance in such protocol versus conventional double-stranded DNA (dsDNA) method. We assumed that some fractions of extra-short cfDNA fragments obtained by Adaptor-ligation ssDNA (LIG-ssDNA) protocol are actually released from damaged DNA structures, where nicks and/or gaps are present in the single strands of the double stranded DNA structures. We speculated that cfDNA repair could diminish such extra-short cfDNA fragments (<100 bp) enriched by LIG-ssDNA protocol through filling gaps and nicks on DNA strands. To validate such assumption, we performed in parallel dsDNA and LIG-ssDNA library preparation methods following either sham or PreCR treatment. We observed a decrease of extra-short cfDNA fragments (<100 bp) in repaired LIG-ssDNA library compared with its sham counterpart. For cfDNA fragments longer than 250 bp, increment of cfDNA fragments was very limited (FIG. 11). We concluded that although some portion of extra-short cfDNA fragments were diminished after repair, there was no evidence suggested such portion contributed to an increase of longer cfDNA fragments. Therefore, the ability of long cfDNA fragment recoveries in LIG-ssDNA libraries was inferior than the dsDNA libraries. Repair of defects with PreCR is less effective on single-stranded DNA library preparation protocol than with double-stranded DNA library preparation protocol.

5. cfDNA Repair Performance in cfDNA from Mouse Plasma

Figure 12:
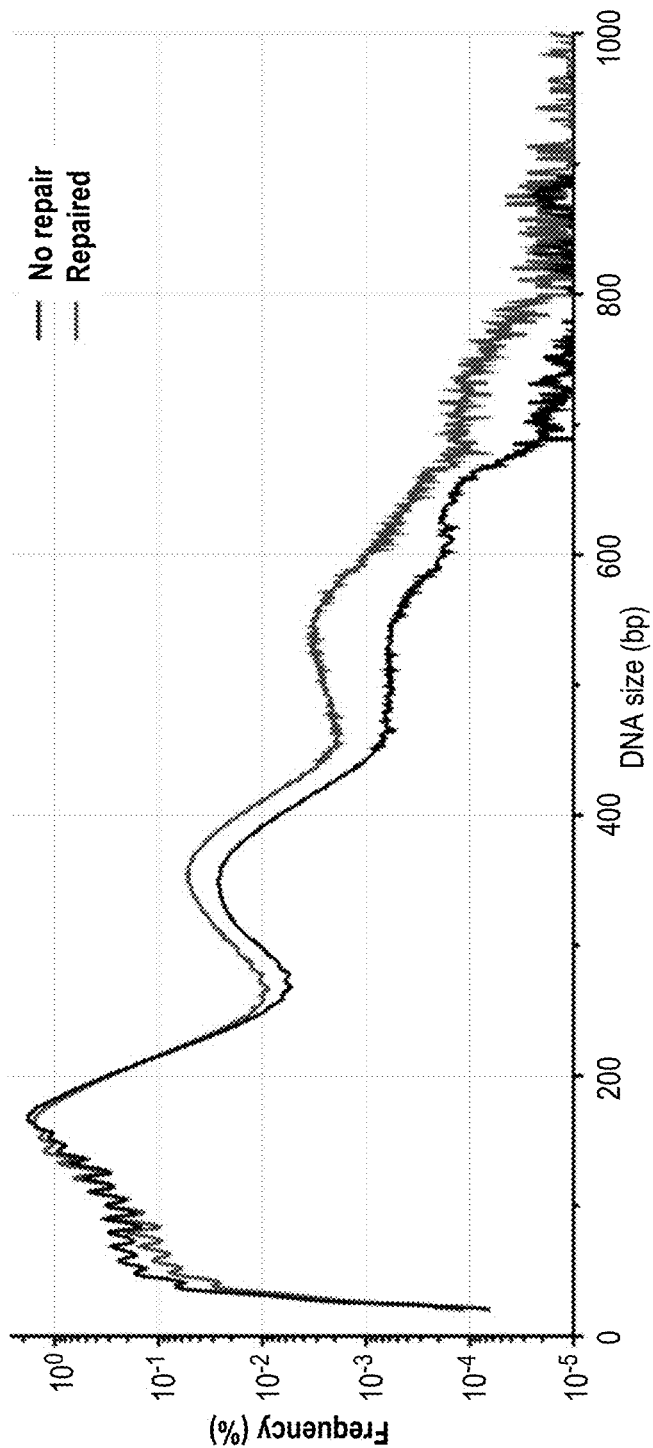
FIG. 12 shows size profiles of cfDNA from mice with and without repair according to embodiments of the present invention.

To validate if the repair of cfDNA damages is also present in non-human mammals, we evaluated the performance of cfDNA repair in cfDNA from a mouse. Plasma was isolated from two C57BL/6 wide type (WT) mice, DNA was extracted from plasma followed by either sham or repair treatment. Sequencing dsDNA libraries were prepared in the exact human scenario. We observed there was a 70% increase of long (200-1000 bp) cfDNA fragments after repair treatment (FIG. 12). There was a 1.41 times enrichment of long (>200 bp) cfDNA fragments in repaired than the counterpart without repair treatment. cfDNA fragment frequencies are presented in log scale. This result is concordant with the human cohort, suggesting similar cfDNA damage patterns are shared by high order organisms, such as mammals.

II. DNA Repair Study with Fetal Trisomy and SLE Patients

DNA fragments from additional subjects were treated to repair intrastrand defects. DNA fragments from maternal plasma of pregnant women, each carrying a singleton trisomy 21 fetus, were repaired. Additionally, DNA fragments from patients with active or inactive systemic lupus erythematosus (SLE) were repaired. The repaired DNA fragments were analyzed for their effect on short and long fragments and for their impact in detecting a condition of the sample. The references in Section II are numbered separately from the references in the other sections, and the references are provided in a list at the end of the section.

A. Materials and Methods

This study was approved by the institutional ethics committee. Ten first trimester and ten third trimester pregnant women with singleton male fetuses were recruited. Five pregnant women with singleton trisomy 21 fetuses were also recruited. Four patients with systemic lupus erythematosus (SLE) were recruited. All SLE patients fulfilled the American College of Rheumatology diagnostic criteria and their lupus disease activities were assessed by the SLE disease activity index (SLEDAI), which is a clinical measurement of the disease activity.[1] Two patients had inactive SLE (SLEDAI median: 1; range 0-2) and the other two had active SLE (SLEDAI both equal to 8). Anti-dsDNA antibody levels of all patients were also measured by the time of blood sampling. All pregnancy samples were recruited from the Department of Obstetrics and Gynaecology, Prince of Wales Hospital, Hong Kong. SLE samples were recruited from the rheumatology clinic at the Department of Medicine and Therapeutics, Prince of Wales Hospital, Hong Kong. All subjects had informed consent.

1. Library Preparation

Plasma was isolated from 20 mL of EDTA-anticoagulated maternal peripheral blood as previously described.[2] For third trimester cases, 1 cm³ placental tissue was dissected freshly after delivery from a region 2 cm deep and 5 cm away from the umbilical cord. For first trimester cases, chorionic villus samples (CVS) were obtained. Plasma and buffy coat genomic DNA were extracted using the QIAamp DSP DNA Blood Mini Kit (Qiagen) and QIAamp DNA Blood Mini Kit (Qiagen) respectively, and quantified by Qubit 3.0 (Invitrogen). Placental DNA and chorionic villus DNA were extracted using the QIAamp DNA Mini Kit (Qiagen) according to manufacturer's protocols. For cell-free DNA (cfDNA) repair, 10 ng of extracted plasma DNA input for each subject was repaired by using PreCR Repair Mix (New England Biolabs).

A sham control was done in parallel with the same amount of DNA input and reaction buffer only. All DNA repair or sham treatments were done according to manufacturer's instructions. Sham- or repaired-treated plasma DNA were purified by MinElute Reaction Cleanup Kit (Qiagen) to remove residual enzymes and reagents, followed by sequencing library preparation. Double-stranded DNA (dsDNA) libraries were generated by the KAPA HTP Library Preparation Kit for Illumina (KAPA Biosystems) according to manufacturer's instructions. Adaptor-ligation single stranded DNA (LIG-ssDNA) libraries were generated by the Accel-NGS 1S Plus DNA Library Kit (SWIFT Biosciences). Libraries were quantified by Qubit and real-time quantitative PCR on a LightCycler 96 System (Roche). The size profiles of the sequencing libraries were examined by the Agilent High Sensitivity D1000 ScreenTape System (Agilent). All libraries were sequenced with a paired-end (PE) format of 75 bp×2 on a NextSeq 500 system (Illumina). Adaptor sequences and low quality bases (i.e., quality score, <5) were removed and libraries were aligned to the non-repeat-masked human reference genome (hg19) using the Short Oligonucleotide Alignment Program 2 (SOAP2).[3] Up to two nucleotide mismatches, but not indels, were allowed for each member of the pair-end reads.

For mouse plasma cfDNA repair, total blood samples from two wildtype (WT) C57BL/6 mice were obtained via cardiac puncture at 10-12 weeks of age. The blood was collected into EDTA-containing collection tubes and plasma was isolated as previously described.[4] 10 ng of cfDNA input was subjected to sham- or repair treatment, before dsDNA sequencing library preparation. For SLE plasma samples, all extracted cfDNA of each sample were evenly separated into sham- or repair treatment before dsDNA sequencing library preparation.

2. Microarray Genotyping and Single Nucleotide Polymorphism (SNP) Identification Fetal and maternal genomic DNA samples were genotyped with the Infinium Omni2.5-8 V1.3 Kit and the iScan system (Illumina). SNPs were called by the Birdseed v2 algorithm with a confidence score cutoff of 0.15.[5] The genotypes of the CVS and placentas were compared with those of the mothers to identify the fetal-specific and maternal-specific SNP alleles. A SNP was considered as fetal-specific if it was homozygous in the mother and heterozygous in the fetus, and the reverse for maternal-specific SNPs. The fetal DNA fractions were deduced as described.[2] Briefly, fetal DNA fraction (F) was deduced by the allelic ratio between a fetal specific SNP allele (p) and a common SNP allele (q) shared by the mother and the fetus using the following formula:[6]

$$F = \frac{2p}{p+q} \times 100\%$$

In the size-fractionated fetal fraction analysis, fetal DNA fragments were divided into 10-bp bins as previously described,[7] with modified size range of analysis. For detection of trisomy 21, overrepresentation of Chr21 of each sample was quantified by the z-score using the following formula:

$$z\text{-score} = \frac{GRchr21_{test\ sample} - \text{mean } GRchr_{euploid}}{SD_{euploid}}$$

where GRchr21 is the genomic representation (GR) of chromosome 21.

B. Results

Repairing DNA fragments was found to enrich longer fragments in both biological samples from pregnant women carrying singleton trisomy fetuses and in biological samples from active and inactive SLE patients. Repairing DNA fragments from maternal plasma was found to improve sensitivity and specificity for determining trisomy in a fetus. PreCR repair treatment enriched longer (>250 bp) cfDNA molecules without significantly losing shorter (<166 bp) ones. Repairing DNA fragments allows for more DNA fragments from a biological sample to be used for analysis of trisomy or SLE or other conditions than a biological sample without repair. Repairing DNA fragments gave a larger absolute separation difference between inactive and active SLE samples. This translated into a relative 33.7% improvement for potential molecular diagnostics development.

1. Size Profile Characteristics of Sham- or PreCR-Repaired cfDNA from Trisomy 21 Maternal Plasma Samples FIG. 13 shows a table of size distributions of short (0-250 bp) and long (>250 bp) cfDNA fragments from maternal plasma of pregnant women carrying a fetus with trisomy 21. Similar to the results from first and third trimester maternal plasma samples, we observed that there was an average of 3.3% absolute decrease (95.5%-92.2%) of short (0-250 bp) cfDNA fragments and an average of 3.7% absolute increase (4.1%-7.8%) of long (>250 bp) cfDNA fragments in all trisomy 21 samples after PreCR repair treatment.

Figure 14B:
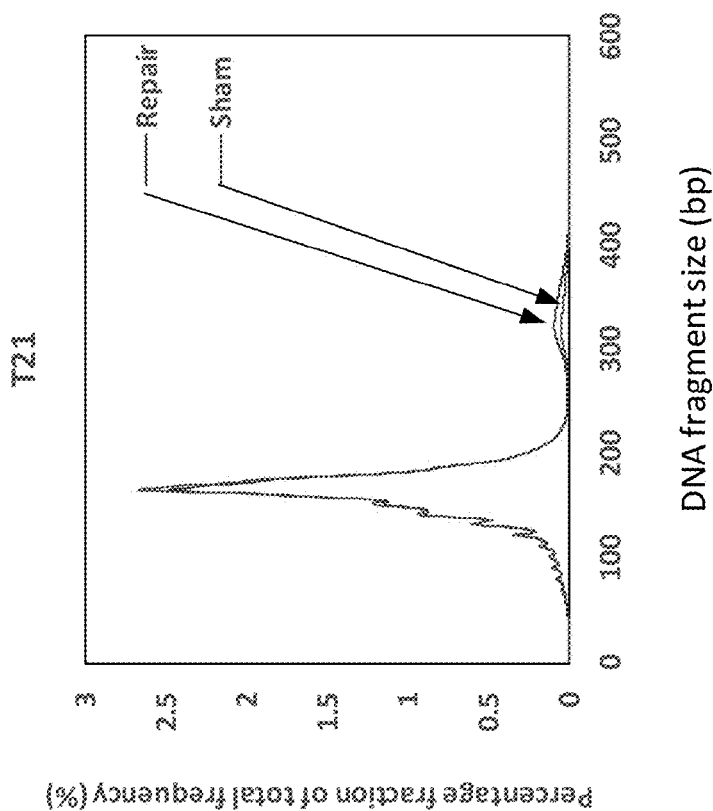
FIGS. 14A and 14B show averaged size profiles with and without repair from five women each carrying a trisomy 21 fetus according to embodiments of the present invention.
Figure 14A:
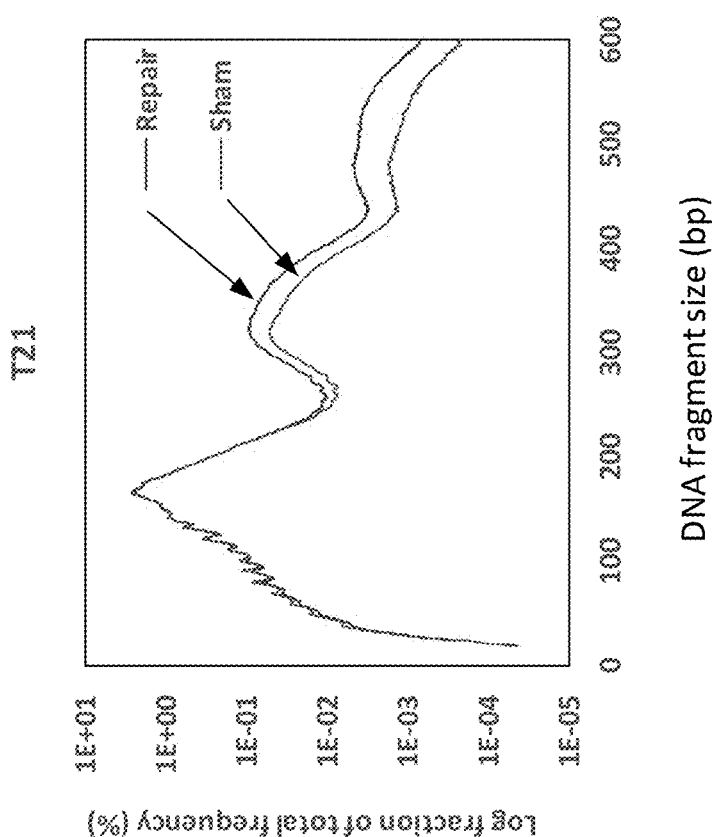

FIGS. 14A and 14B show the size profiles of DNA fragments in trisomy 21 samples before and after repair. FIG. 14A and FIG. 14B are graphs of the percentage fraction of the total frequency versus DNA fragment size. FIG. 14A shows the percentage fraction on a log scale, and FIG. 14B shows the percentage fraction on a linear scale for the same data. Sham and PreCR-repaired treated fragments are plotted on each graph. The PreCR-repaired fragments show a larger fraction of longer fragments than the sham fragments.

Figure 15:
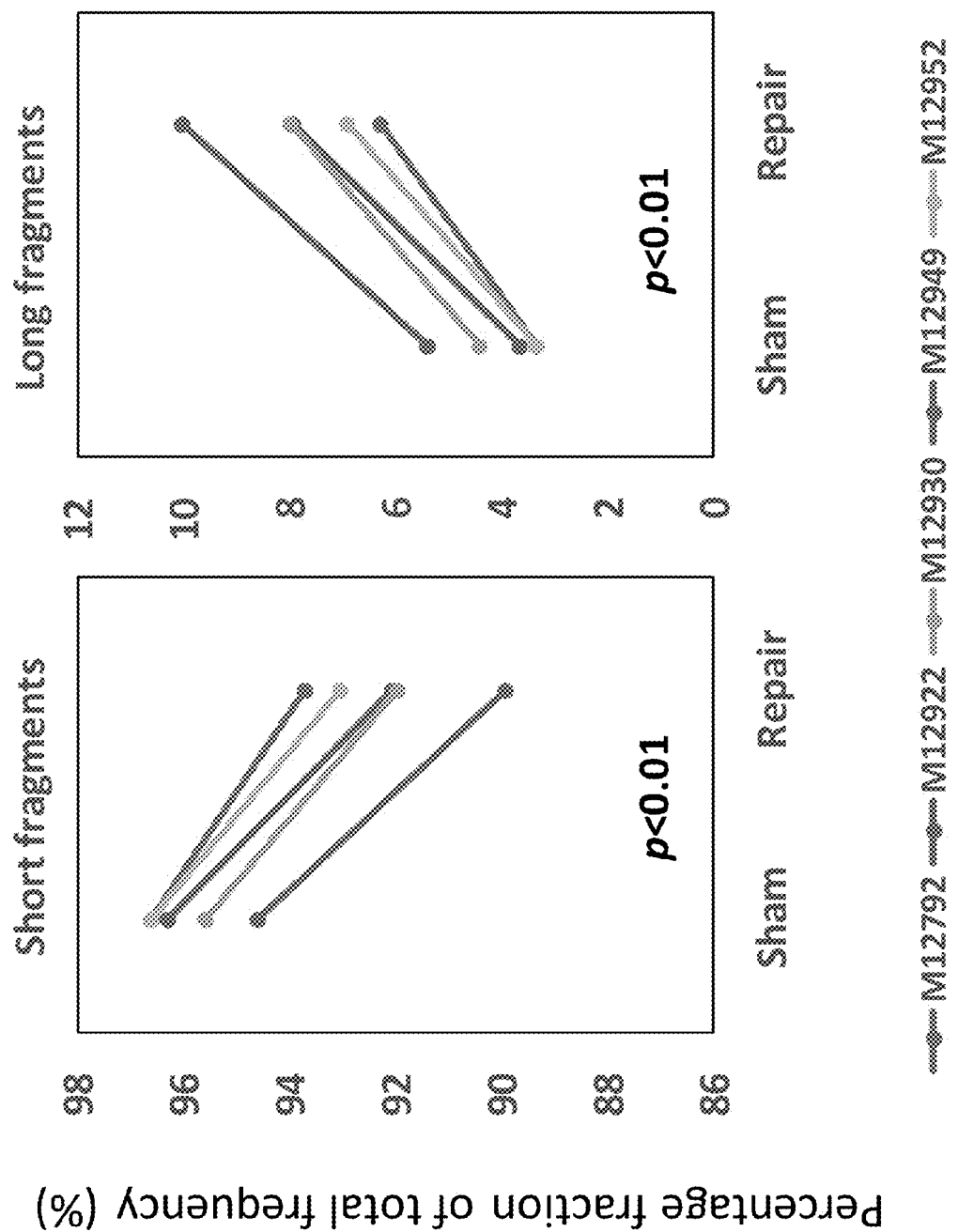
FIG. 15 shows the quantification of short (0-250 bp) and long (251-600 bp) cfDNA molecules from five women each carrying a trisomy 21 fetus after sham-repaired or PreCR-repaired treatment according to embodiments of the present invention.

FIG. 15 shows the quantification of short (0-250 bp) and long (251-600 bp) cfDNA molecules from five women each carrying a trisomy 21 fetus after sham-repaired or PreCR-repaired treatment. The graphs in FIG. 15 show the percentage fraction of the total frequency for both sham and repair treatment fragments. The short fragments show a drop in the percentage fraction. The long fragments show an increase in the percentage fraction. Statistical analyses showed that both changes were significant (both p<0.01; Student paired t test).

2. Improved NIPT Performance of Trisomy 21 after PreCR Repair Treatment

As the repaired cfDNA sample has more intact long cfDNA molecules that are analyzable from the fetus, we aimed to demonstrate its potential application for prenatal diagnosis. We recruited five pregnancies with trisomy 21 fetuses and compared the chromosomal representation of Chr21 with the 10 first trimester euploid cases, which would be the most clinically relevant samples for NIPT. We observed that after PreCR repair treatment, Chr21 z-scores for the trisomy 21 cases showed an average increase in 17.3% (ranging from 14.4% to 19.8%) and exhibited better separation from the z-scores of the euploid samples (FIG. 16).

Figure 16:
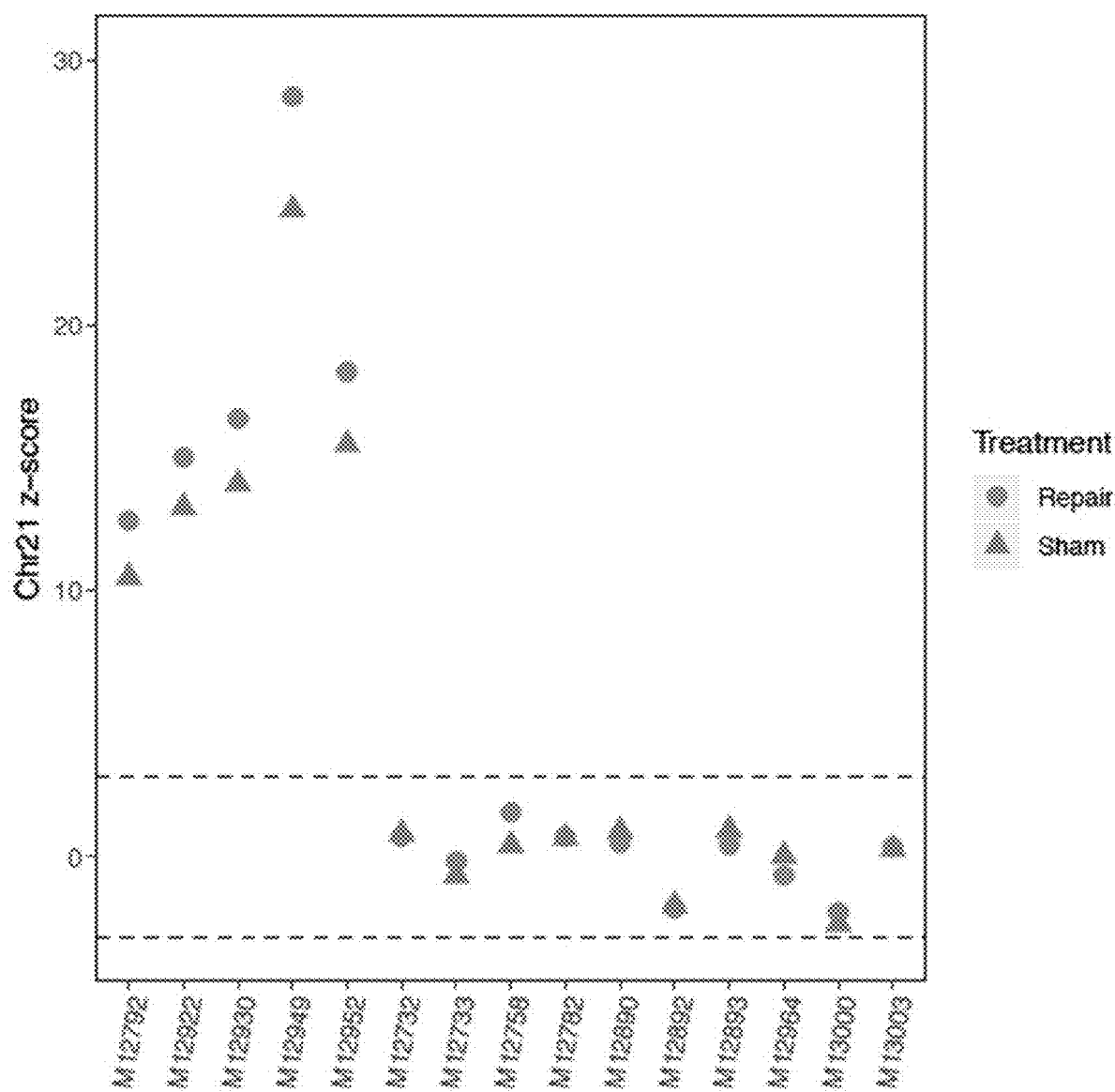
FIG. 16 shows improved noninvasive prenatal testing (NIPT) performance of trisomy 21 after PreCR repair treatment according to embodiments of the present invention.

In FIG. 16, the chromosome 21 z-scores of five trisomy 21 samples are shown on the left, and the chromosome 21 z-scores of 10 euploid samples are shown on the right. The repaired trisomy 21 samples showed increased z-scores and greater separation from the euploid samples. These results suggested that PreCR repair treatment may improve NIPT performance of trisomy 21 pregnancies. The repair treatment may allow a lower fetal fraction to be used for aneuploidy analysis. The repair may also allow for a classification of an aneuploidy in situations where non-repaired DNA for an aneuploidy would not have shown a high enough z-score to classify as an aneuploidy. The repair treatment may result in a method with increased sensitivity, specificity, and/or accuracy over a method without a repair treatment.

a) Simulation Details

In order to demonstrate the plasma DNA repair effect quantitatively, we performed a simulation analysis followed by receiver operating characteristic (ROC) analysis to determine whether using plasma DNA reads with repair provides an advantage over plasma DNA reads without repair using DNA reads mapped to chr21 in pregnant women carrying trisomy 21 fetuses. In the simulation, the fetal fraction was assumed to be 1% and the total sequenced reads were assumed to be 3 million. The relative increase of fetal fraction after PreCR repair was set to be 4.8%.

In the computer simulation, the number of sequenced reads of plasma DNA derived from a particular chromosome is assumed to follow the binomial distribution. For a pregnant woman carrying an euploid fetus, the proportion of sequenced reads of plasma DNA originating from chromosome 21 (chr21) is denoted as $GR_{21}$. Among a total sequenced reads (n), the number of reads derived from chr21 (E) would follow the distribution below:

$$E \sim \text{Binom}(n, GR_{21}), \quad (1)$$

where 'Binom' represents the binomial distribution.

For a pregnant woman carrying a trisomy fetus, the proportion of sequenced reads of plasma DNA originating from chr21 is denoted as $GR'_{21}$:

$$GR'_{21} = \left(1 + \frac{f}{2}\right) \times GR_{21}, \quad (2)$$

where f is the fetal DNA fraction in the maternal plasma DNA of a pregnant woman. Among total sequenced reads (n), the number of reads derived from chr21 (T) would follow the distribution below:

$$T \sim \text{Binom}(n, GR'_{21}), \quad (3)$$

which could be rewritten as:

$$T \sim \text{Binom}\left(n, \left(1 + \frac{f}{2}\right) \times GR_{21}\right), \quad (4)$$

After the repair of plasma DNA prior to sequencing, f would increase to f', which is governed by the below formula:

$$f' = (1+\alpha) \times f, \quad (5)$$

where $\alpha$ is the relative increase of the fetal DNA fraction after plasma DNA repair. In this scenario, for a pregnant woman carrying a trisomy fetus, among total sequenced reads (n), the number of reads derived from chr21 (G) would follow the distribution below:

$$G \sim \text{Binom}\left(n, \left(1 + \frac{(1+\alpha) \times f}{2}\right) \times GR_{21}\right), \quad (6)$$

According to (1), (4), and (6), we simulated sequenced reads originating from chr21 for 100 plasma DNA samples from pregnant women carrying euploid fetuses and those carrying trisomy 21 fetuses, respectively. We also simulated 100 plasma DNA followed by DNA repair from those carrying trisomy 21 fetuses. For each sample, the fetal fraction was assumed to be 1% and the total sequenced reads (n) were assumed to be 3 million. Compared with pregnant women carrying euploid fetuses, the receiver operating characteristic (ROC) analysis was used to determine the diagnostic differences between the percentage of plasma DNA reads with and without DNA repair mapped to chr21 in pregnant women carrying trisomy 21 fetuses.

The binomial distributions were generated with the R function rbinom. ROC curves for the groups with and without DNA repair were plotted with R package pROC (version 1.15.3). The DeLong's test was adopted to compare ROC curves to determine if the improvement of trisomy 21 detection using the method with DNA repair protocol is statistically significant compared with a method without DNA repair.

b) Simulation Results

Figure 17:
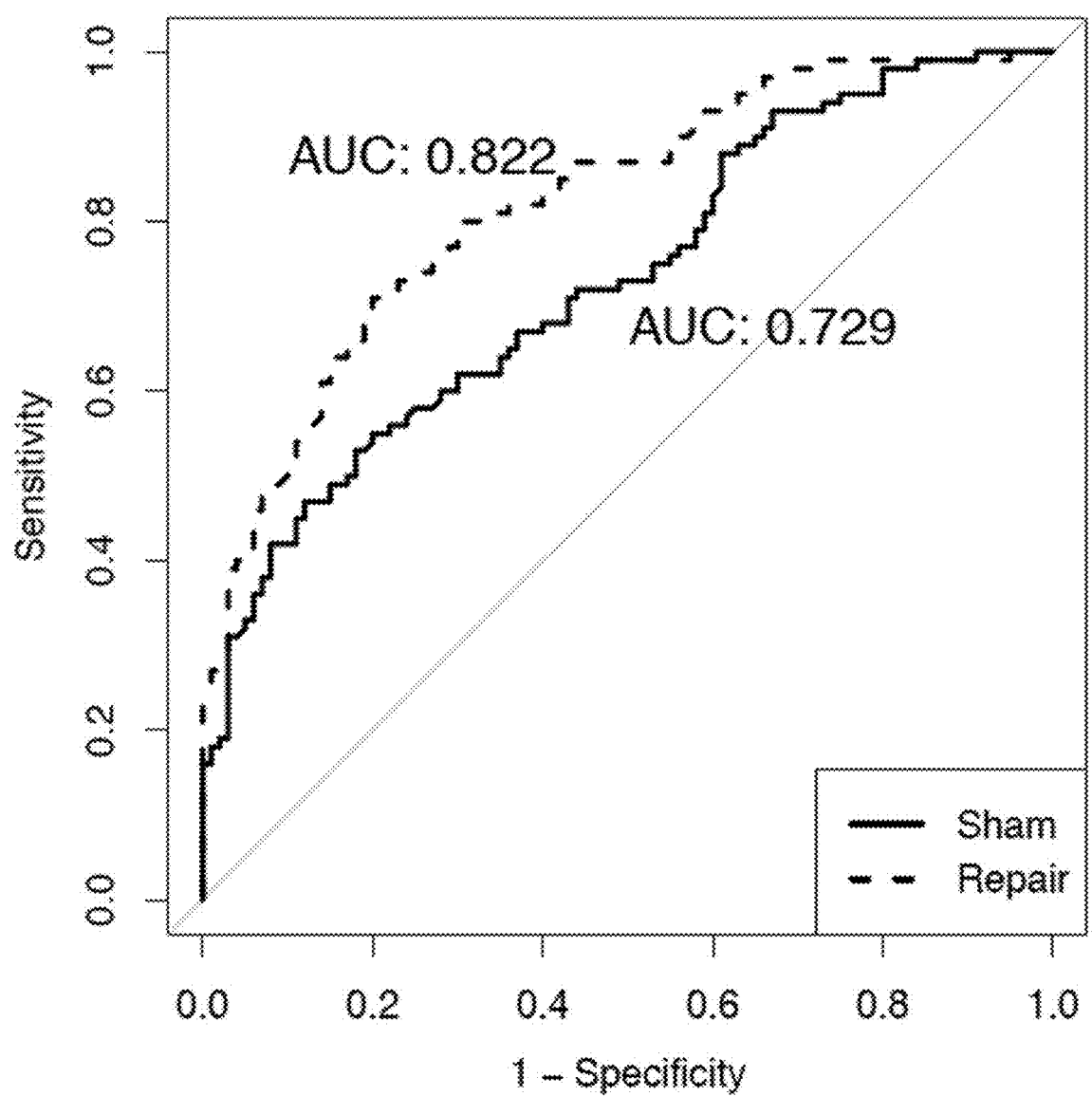
FIG. 17 shows a receiver operating characteristic curve for the improvement in determining trisomy after repair according to embodiments of the present invention.

FIG. 17 shows the ROC curve for the results of the simulation comparing detecting trisomy 21 with DNA repair and without DNA repair. The results showed an improvement of area under the curve (AUC) from 0.729 to 0.822 after repair. Statistical analysis using DeLong's test showed the improvement was significant (sham vs. repair, DeLong's test: p=0.006013). Hence, repairing DNA can improve sensitivity and specificity of determining trisomy in a fetus using DNA fragments from maternal plasma.

3. Increased Longer cfDNA Molecules in Plasma from SLE Patients after PreCR Repair Treatment The cfDNA size profiles of cfDNA molecules from SLE patients is different compared to normal subjects.[8] Prominent enrichment of cfDNA fragments shorter than 115 bp has been previously reported.[8] Moreover, the severity of the disease corresponds to the amount of such extra-short cfDNA fragments, i.e., active SLE patients have more extra-short fragments in their plasma. Based on this, we aimed to explore the impact of PreCR repair treatment on the size profiles of cfDNA molecules from SLE patients. We recruited 2 inactive (SLEDAI=0-2) and 2 active (SLEDAI=8) SLE patients, extracted cfDNA from their plasma and subjected to sham- or repair treatment.

FIG. 18 includes the sample number, SLE disease activity index (SLEDAI) level, anti-ds DNA antibody level of the SLE patients, and the total DNA amount from plasma. SLEDAI and anti-ds DNA antibody level are clinical measurements of the disease activity. A higher SLEDAI and a higher anti-ds DNA antibody level correspond to a more active SLE status.

We observed an increase in longer cfDNA fragments after repair, similar to the results from the maternal plasma samples.

Figure 19:
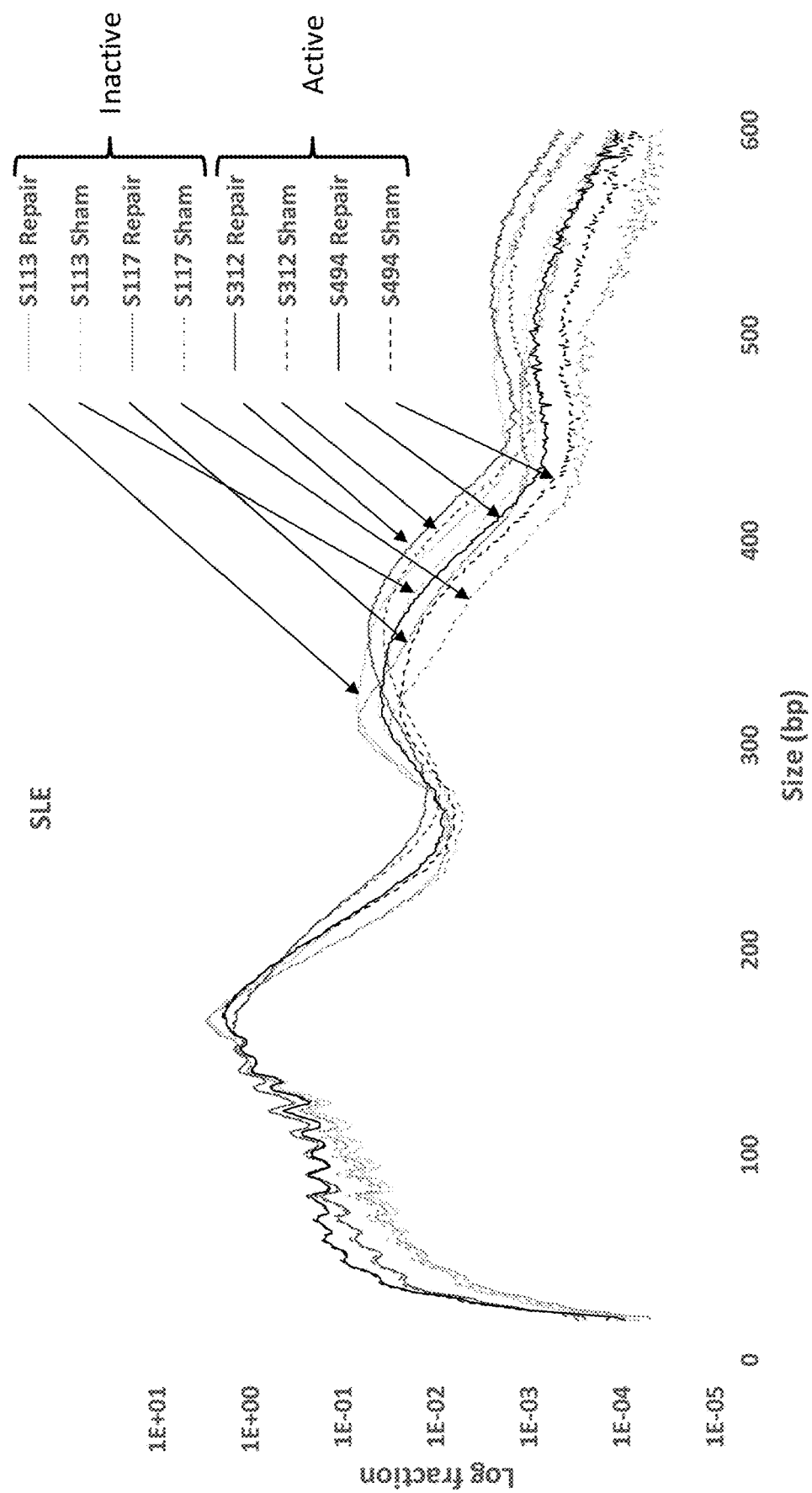
FIG. 19 shows the size profile on a log scale of DNA fragments with and without repair from four SLE patients according to embodiments of the present invention.
Figure 20:
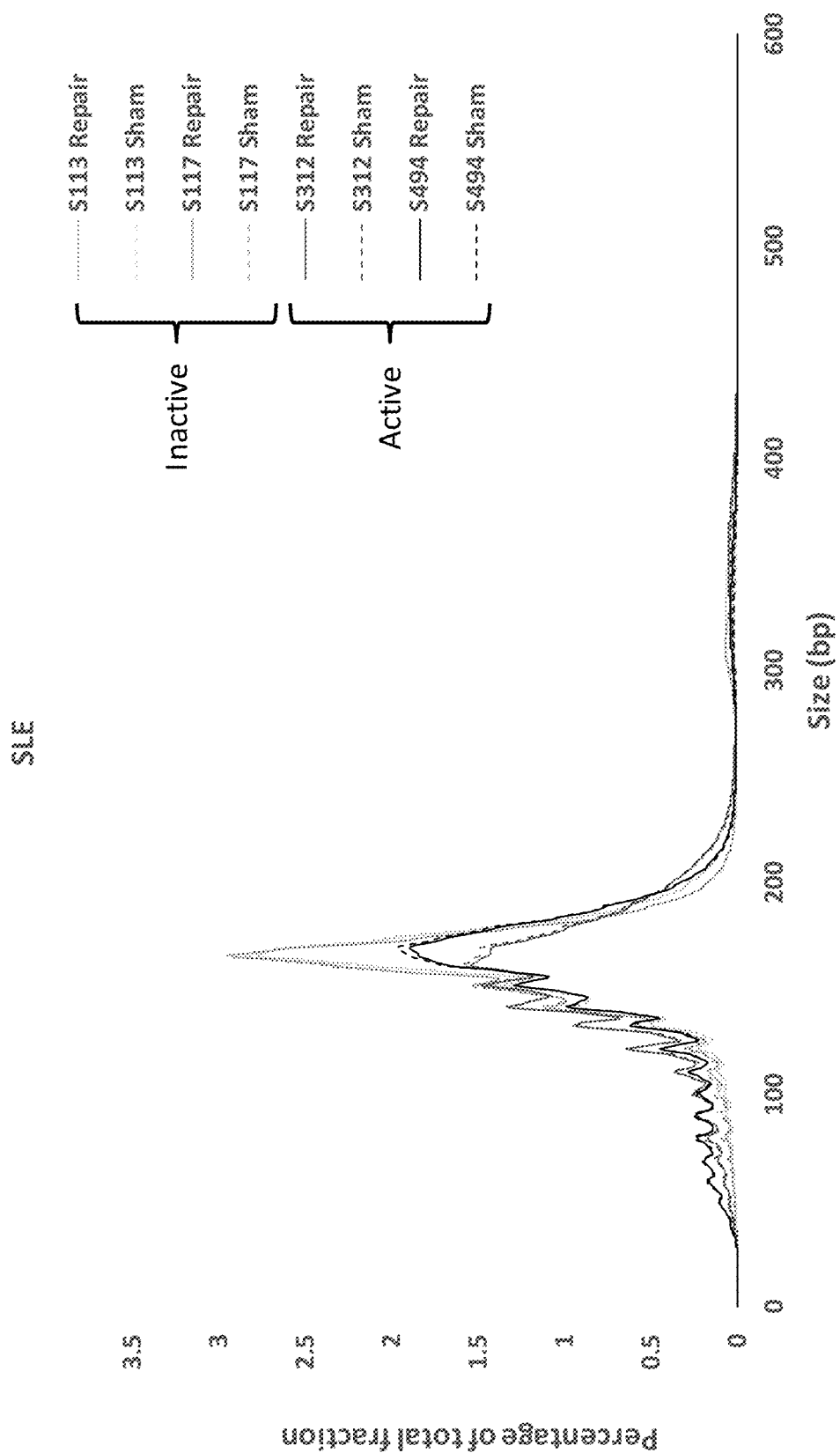
FIG. 20 shows the size profile on a linear scape of DNA fragments with and without repair from four SLE patients according to embodiments of the present invention.

FIG. 19 and FIG. 20 show the size profiles of the cfDNA with and without repair from each of the SLE patients. FIG. 19 shows the log of the fraction versus the size of the DNA fragments. FIG. 19 shows the same data on a linear scale. Samples from four patients (S113, S117, S312, S494) were analyzed, with each patient having a sham and a repair sample. The sham data are shown with dashed lines, and the repaired data are shown with solid lines. Two patients had inactive SLE, and two patients had active SLE. The graphs show an increase in longer DNA fragments (>250 bp) with repair. Shorter DNA fragments (<200 bp) show a slight decrease with repair.

Figure 21A:
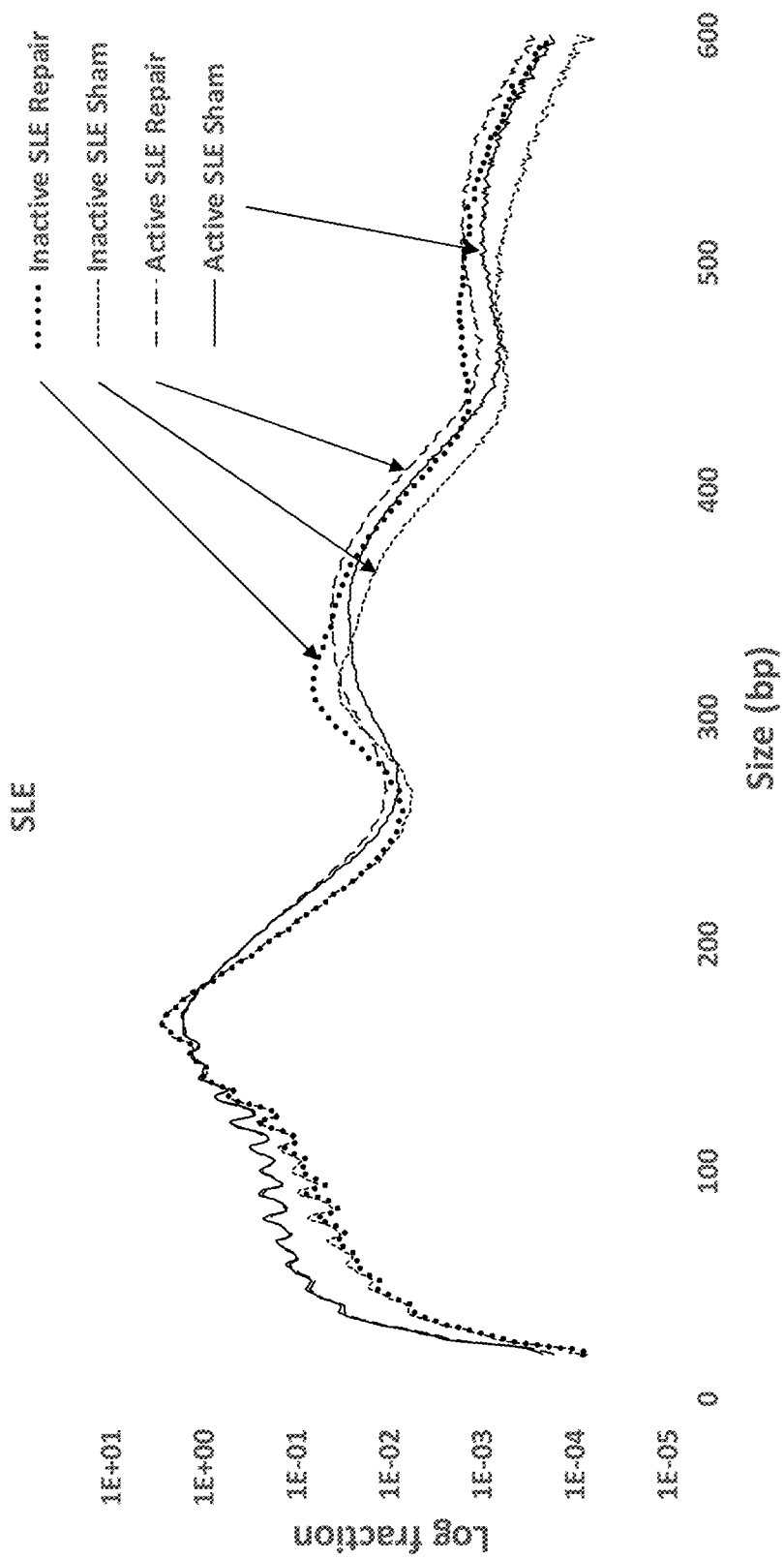
FIGS. 21A and 21B show averaged size profiles comparison of sham-repaired and PreCR-repaired cfDNA from 4 SLE patients (2 inactive SLE; 2 active SLE) according to embodiments of the present invention.
Figure 21B:
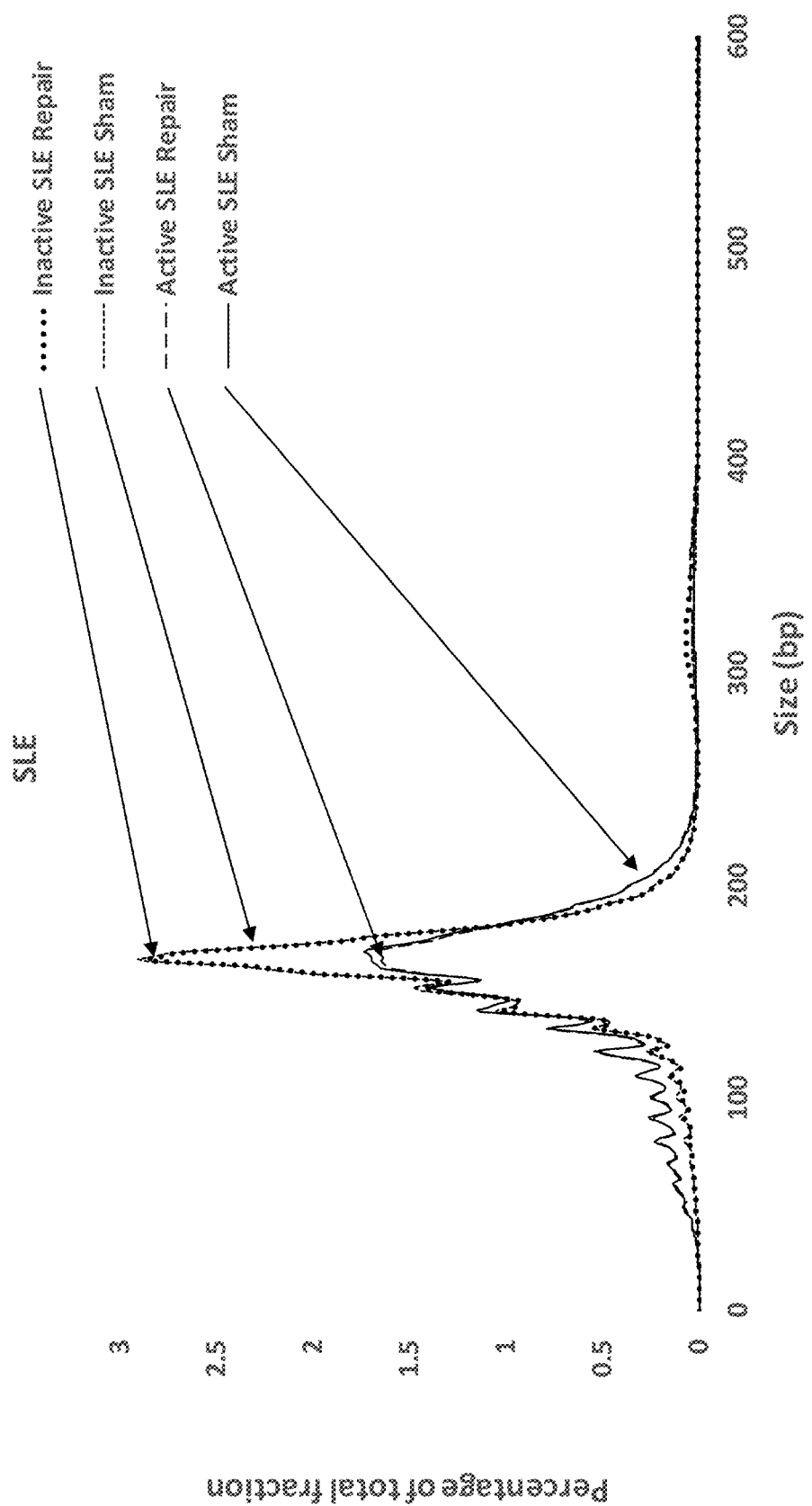

FIG. 21A and FIG. 21B show the averaged results from the inactive and active SLE patients displayed in FIG. 19 and FIG. 20. FIG. 21A shows the log fraction versus DNA fragment size. FIG. 21B shows the same data on a linear scale. The graphs show an increase in longer DNA fragments (>250 bp) with repair. Shorter DNA fragments (<200 bp) show a slight decrease with repair.

FIG. 22 shows a table of the percentage changes and percentages in different size ranges of DNA fragments in active and inactive SLE patients after cfDNA repair. FIG. 22 involves the same data displayed in FIG. 19 and FIG. 20. The table has four different size ranges: short (0-250 bp), long (>250 bp), 0-115 bp, and >200 bp. The size ranges of 0-115 bp and >200 bp are ranges that were used in Chan et al., PNAS (2014).[8] The percentage of each size range is reported for inactive SLE patients and active SLE patients. The first two percentages in each cell of the table are the percentage of the size range before repair and after repair. The percentage in parentheses indicates the relative percentage increase or decrease after repair.

FIG. 23 shows the average percentage changes of inactive SLE and active SLE patients after repair. FIG. 23 shows the percentage changes after averaging data from the patients, similar to the data plotted in FIG. 21A and FIG. 21B. For inactive SLE patients, there was an average of 2.3% decrease (97.4%-95.2%) of short (0-250 bp) cfDNA fragments and an average of an 88.0% (2.6%-4.8%) increase of long (251-600) cfDNA fragments after PreCR repair treatment. For active SLE patients, there was an average of 1.4% decrease (97.2%-95.8%) of short cfDNA fragments and an average of 49.3% (2.8%-40.2%) increase of long cfDNA fragments after PreCR repair treatment. However, we did not observe any significant change in amount of cfDNA molecules with the size shorter or equal to 166 bp.

When revising the size ranges of short and long DNA fragments into 0-115 bp and >200 bp, respectively, the changes were similar to the 0-250 bp and >250 bp changes. For inactive SLE samples, there was an average of relative 14.5% decrease (4.3%-3.7%) and 46.8% (5.4%-7.6%) increase of short (0-115 bp) and long (>250 bp) cfDNA fragments after PreCR repair treatment, respectively. For active SLE patients, there was an average of relative 4.3% decrease (11.8%-11.3%) and 21.7% (7.8%-9.4%) increase of short (0-115 bp) and long (>250 bp) cfDNA fragments after PreCR repair treatment, respectively. The PreCR repair treatment increases the number of DNA fragments available for diagnosis of SLE. For evaluating the diagnostic potential of SLE patients using PreCR repair, we size-binned (limited to 120-130 bp) and separately plotted the absolute percentages of inactive and active SLE samples after either sham or PreCR repair treatment.

Figure 24A:
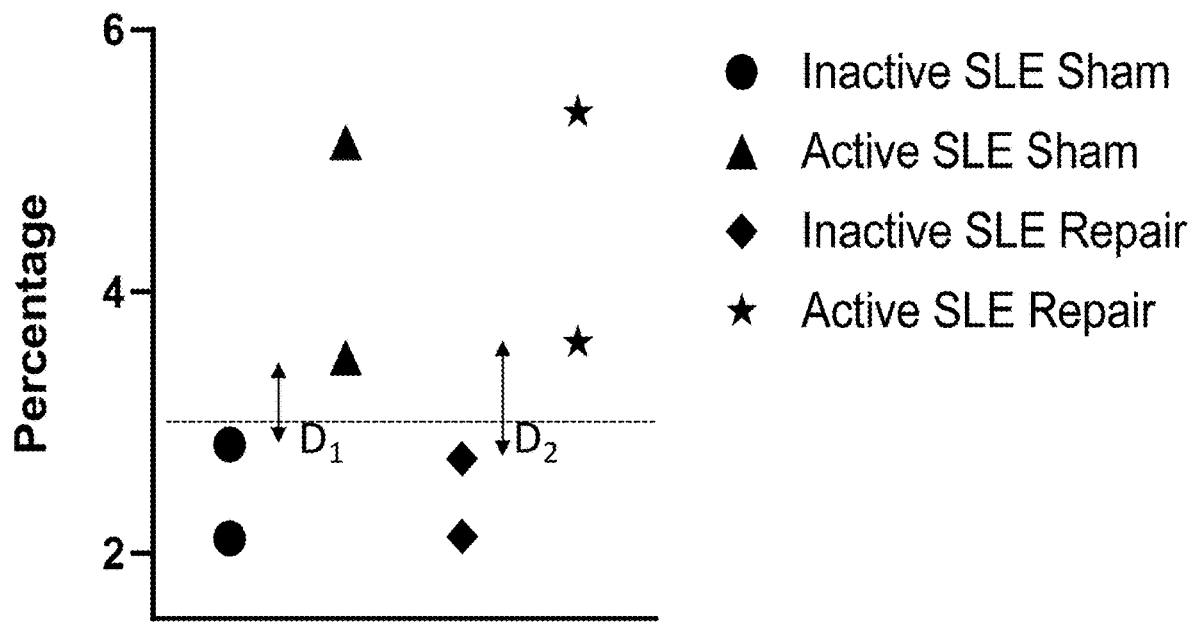
FIG. 24A and FIG. 24B plot the molecular diagnostic potential of SLE patients using sham and repair DNA fragments according to embodiments of the present invention.
Figure 24B:
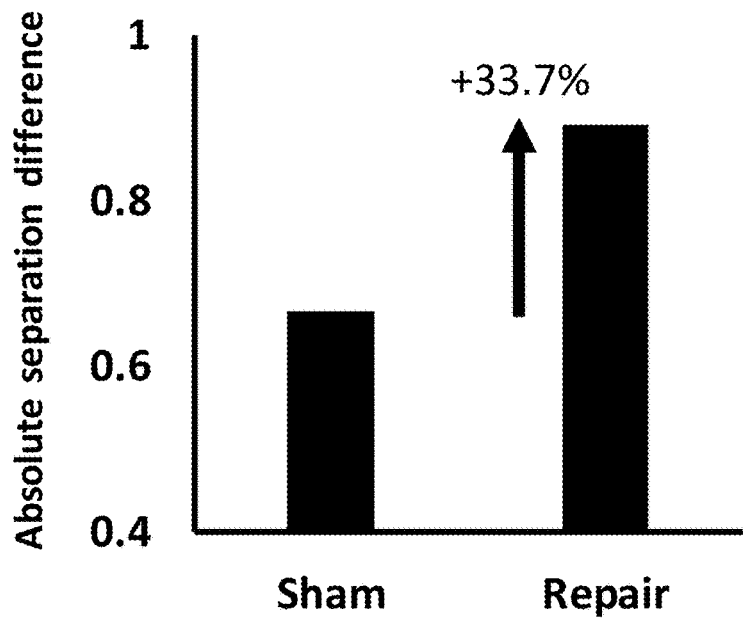

FIG. 24A and FIG. 24B plot the molecular diagnostic potential of SLE patients using sham and repair DNA fragments. FIG. 24A is a graphical representation of data for 120-130 bp in FIG. 22. FIG. 24A plots the absolute percentages of inactive and active SLE samples after sham or PreCR repair treatment. Size binning was set to 120-130 bp. $D_1$ and $D_2$ represent the absolute separation differences between inactive and active SLE samples after sham or PreCR repair treatment, respectively. FIG. 24B plots a bar chart showing a relative 33.7% increase in the absolute separation difference in repaired SLE samples. This better separation between inactive and active SLE samples after PreCR repair is an advantage in determining the level of SLE in a patient compared to non-repaired DNA fragments. Multiple size ranges were tested, with the 120-130 bp size range showing the best separation between inactive and active SLE samples after repair treatment. However, other size ranges may also be used, including 100-110 bp, 110-120 bp, 130-140 bp, or 140-150 bp.

4. References for Sections II, III.B, and III.C

1. Bombardier C, Gladman D D, Urowitz M B, Caron D, Chang C H. Derivation of the SLEDAI. A disease activity index for lupus patients. The Committee on Prognosis Studies in SLE. *Arthritis Rheum.* 1992; 35(6):630-640.
2. Lo Y M, Chan K C, Sun H, et al. Maternal plasma DNA sequencing reveals the genome-wide genetic and mutational profile of the fetus. *Sci Transl Med.* 2010; 2(61): 61ra91.
3. Li R, Yu C, Li Y, et al. SOAP2: an improved ultrafast tool for short read alignment. *Bioinformatics.* 2009; 25(15): 1966-1967.
4. Cheng T H T, Lui K O, Peng X L, et al. DNase1 Does Not Appear to Play a Major Role in the Fragmentation of Plasma DNA in a Knockout Mouse Model. *Clin Chem.* 2018; 64(2):406-408.
5. Hong H, Xu L, Tong W. Assessing consistency between versions of genotype-calling algorithm Birdseed for the Genome-Wide Human SNP Array 6.0 using HapMap samples. *Adv Exp Med Biol.* 2010; 680:355-360.
6. Jiang P, Peng X, Su X, et al. *Fetal Quant. NPJ Genom Med.* 2016; 1:16013.
7. Vong J S L, Tsang J C H, Jiang P, et al. Single-Stranded DNA Library Preparation Preferentially Enriches Short Maternal DNA in Maternal Plasma. *Clin Chem.* 2017; 63(5):1031-1037.
8. Chan R W, Jiang P, Peng X, et al. Plasma DNA aberrations in systemic lupus erythematosus revealed by genomic and methylomic sequencing. *Proc Natl Acad Sci USA.* 2014; 111(49):E5302-5311.
9. Chen E Z, Chiu R W, Sun H, et al. Noninvasive prenatal diagnosis of fetal trisomy 18 and trisomy 13 by maternal plasma DNA sequencing. *PLoS One.* 2011; 6(7):e21791.
10. Chiu R W, Akolekar R, Zheng Y W, et al. Non-invasive prenatal assessment of trisomy 21 by multiplexed maternal plasma DNA sequencing: large scale validity study. *BMJ.* 2011; 342:c7401.
11. Palomaki G E, Deciu C, Kloza E M, et al. DNA sequencing of maternal plasma reliably identifies trisomy 18 and trisomy 13 as well as Down syndrome: an international collaborative study. *Genet Med.* 2012; 14(3):296-305.
12. Nicolaides K H, Syngelaki A, Ashoor G, Birdir C, Touzet G. Noninvasive prenatal testing for fetal trisomies in a routinely screened first-trimester population. *Am J Obstet Gynecol.* 2012; 207(5):374.e371-376.
13. Pergament E, Cuckle H, Zimmermann B, et al. Single-nucleotide polymorphism-based noninvasive prenatal screening in a high-risk and low-risk cohort. *Obstet Gynecol.* 2014; 124(2 Pt 1):210-218.
14. Cervera R, Khamashta M A, Font J, et al. Morbidity and mortality in systemic lupus erythematosus during a 10-year period: a comparison of early and late manifestations in a cohort of 1,000 patients. Medicine (Baltimore). 2003; 82(5):299-308.

15. Raptis L, Menard H A. Quantitation and characterization of plasma DNA in normals and patients with systemic lupus erythematosus. *J Clin Invest*. 1980; 66(6): 1391-1399.
16. Chen J A, Meister S, Urbonaviciute V, et al. Sensitive detection of plasma/serum DNA in patients with systemic lupus erythematosus. *Autoimmunity*. 2007; 40(4):307-310.

III. Discussion

Our findings demonstrated that cfDNA repair using a repair mixture (e.g., PreCR Repair Mix) could recover a subset of long cfDNA molecules in maternal plasma and from plasma from SLE patients. Relative enrichment of long cfDNA molecules after repair over short ones suggests that long cfDNA molecules contain more reparable DNA damages than their short counterparts. Given that long cfDNA molecules (e.g. >250 bp) existed in the maternal circulation in trace amounts, any enrichment by repair might result in a significant increment in relative terms. Indeed, our data from the Illumina and Pacific Biosciences SMRT sequencing platforms illustrated enrichments of 68.8% and 31.3%, respectively, of cfDNA molecules longer than 250 bp. The enrichment became even more notable when one focused on even longer cfDNA molecules. For example, for cfDNA molecules between 450 bp and 600 bp in size, the enrichment amounts were respectively 109.4% and 44.3%, as measured using the Illumina and the Pacific Biosciences SMRT platforms. For cfDNA molecules longer than 600 bp as measured by the Pacific Biosciences SMRT platform, the enrichment following DNA repair was 50.4%. In short, repair treatment could successfully recover long cfDNA molecules from maternal plasma. It appeared that the longer the cfDNA molecule was, the higher was the enrichment.

Repairing intrastrand defects in cell-free DNA was not previously performed for several reasons. The concentration of cell-free DNA in a biological sample is relatively low, and the concentration of cell-free DNA with defects would be even lower. Repairing the intrastrand defects was therefore thought to provide little benefit to analysis. Additionally, the fraction of clinically-relevant DNA may not increase significantly after repair. For example, FIG. 5 shows that the fetal DNA fraction measured from sham and repair samples was often unchanged. Hence, repairing defects in cell-free DNA may not enhance the signal of clinically-relevant DNA over non-clinically-relevant DNA. However, repairing cell-free DNA was found to have different effects on short and long cell-free DNA.

Different mechanisms may be at play for the generation of short and long cfDNA molecules in plasma. For example, cfDNA molecules shorter than 200 bp would likely be produced by enzymatic digestion during apoptosis. On the other hand, long (>250 bp) cfDNA molecules would likely be generated by other cell death mechanisms, such as necrosis.[11,24-27] As discussed earlier, the enrichment of cfDNA molecules by repair was more prominent between 250 bp and 600 bp. The latter lengths are reminiscent of di- and tri-nucleosomal patterns (circa 330 bp and 500 bp, respectively).

Figure 25:
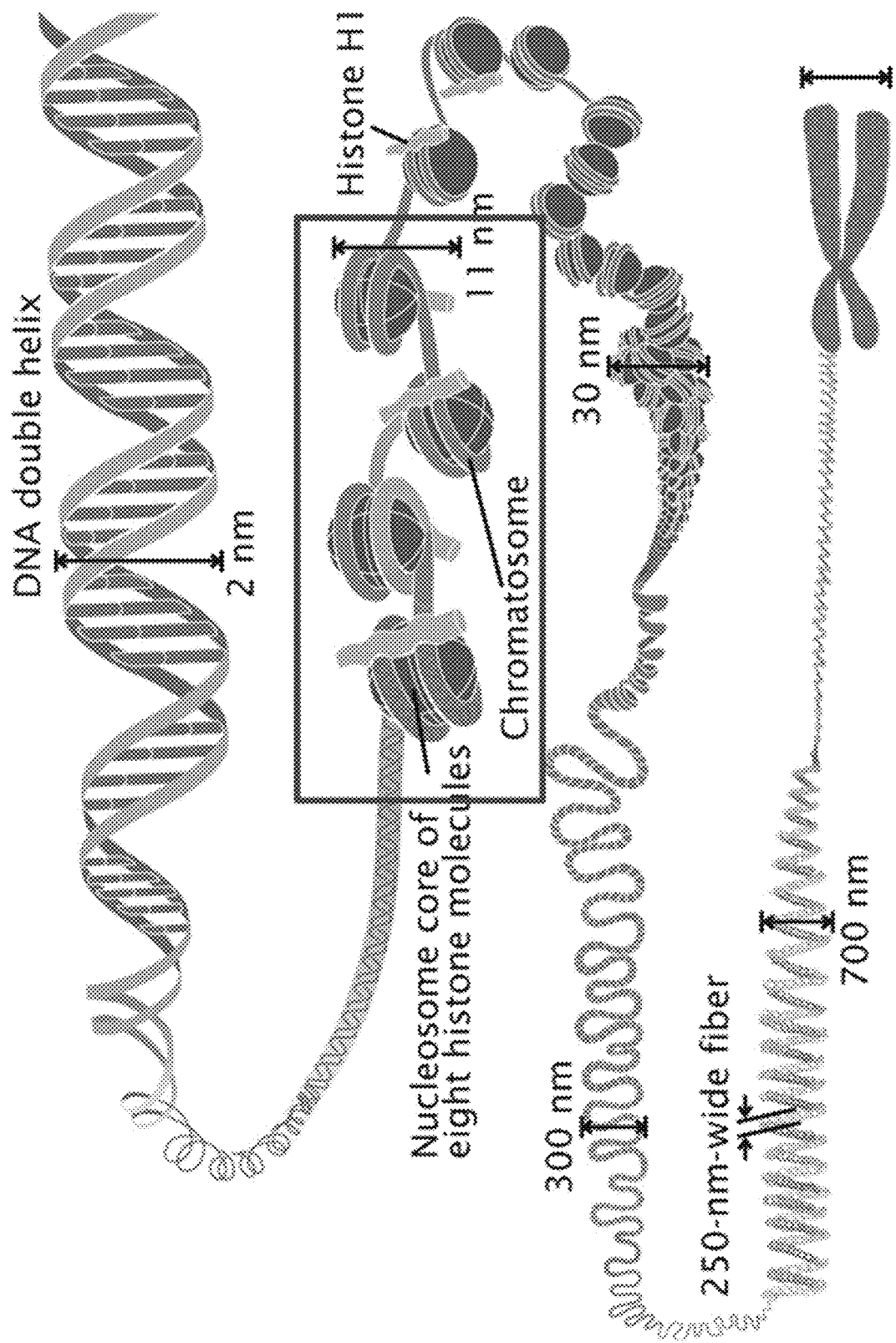
FIG. 25 shows the DNA packing scheme in normal cells according to embodiments of the present invention.

FIG. 25 shows the DNA packing scheme in normal cells. DNA is wrapped around a nucleosome, which is composed of an octamer of 4 core histone proteins (forming a "nucleosome core" wrapped by 147 bp of DNA with a ~10 bp helical repeat), linker histones and linker DNA (mean size around 20 bp). It has been demonstrated that plasma DNA is not randomly fragmented. High resolution plasma DNA size profiling revealed a predominant peak at 166 bp and a 10-bp periodicity below 150 bp.[2] This size profile has been proposed to be closely related to the nucleosomal structure. The peak at 166 bp corresponds to the length of DNA wrapped around one nucleosome core. The peak between 250 and 450 bp (e.g., FIG. 8) may correspond to the length of DNA wrapped around two nucleosome cores. The peak between 450 bp and 600 bp may correspond to the length of DNA wrapped around three nucleosome cores. Repair of cell-free DNA may allow for analysis of more di-nucleosomal and tri-nucleosomal DNA lengths.

From our data, the enrichment of long, but not short, cfDNA molecules after repair suggested that most of the reparable DNA damages might originate from cell death mechanisms other than apoptosis (e.g. necrosis). In contrast, an absence of short cfDNA molecule enrichment after repair treatment suggested that such short cfDNA molecules might not contain reparable DNA damages.

Breaking down total cfDNA into fetal and maternal fractions, our data suggested that DNA damages are not randomly distributed throughout cfDNA molecules of different origins. Although our data revealed that long cfDNA enrichments were occurring in both fetal and maternal cfDNA molecules, the magnitude of enrichment of long fetal cfDNA molecules (82.3%) was higher than that for cfDNA molecules of maternal origin (66.7%) (FIG. 2). In line with this, the small but consistent overall fetal fraction increment after repair suggested that fetal cfDNA molecules might bear more DNA damages (FIG. 5). Possible reasons for this observation could be due to higher accessibility of fetal cfDNA molecules by DNA cutting enzymes.[28] The relatively lower enrichment (14.7%) of long fetal cfDNA molecules following DNA repair in target captured libraries comparing to non-captured enrichment (82.3%) could be due to competition effect between DNA templates with different lengths during target probes hybridization.

The ability of the repair treatment to restore damaged DNA opens up many potential applications. In prenatal diagnosis, repair of cfDNA may improve the success rate of NIPT. In particular, scenarios with non-reportable NIPT results caused by insufficient fetal DNA fraction[29-33] or poor cfDNA quality might be improved by DNA repair. Examples of such scenarios might include NIPT in very early pregnancies, samples obtained from pregnant women with high body mass indices, etc.[34-37] Furthermore, the ability of cfDNA repair to reveal more long analyzable cfDNA molecules in plasma might open up the possibility of using NIPT for long genomic targets, e.g., sequences involved in triplet repeat disorders such as the Fragile-X Syndrome (FXS). In FXS, the length of the CGG tandem repeats in patients with fully mutated FMR1 alleles can be longer than 600 bp.[38,39] Repair of cell-free DNA for use in determining FXS is described below.

Application of cfDNA repair might also be extended to the development of linkage-based NIPT for monogenic diseases. With an increase in analyzable cfDNA length, for selected genomic regions, mutated alleles of single genes from parental carriers flanked by polymorphic markers could be detected in the maternal plasma. This approach might be feasible for genomic regions with high concentrations of SNP clusters occurring in tandem, such as with the human leukocyte antigen (HLA) region. Using repaired cell-free DNA with analysis of the HLA region is described below.

In conclusion, this study has revealed a preferential recovery of long cfDNA molecules in maternal plasma and in plasma from SLE patients after repair treatment. Small but consistent increment of overall fetal DNA fraction is contributed by higher fetal-derived cfDNA molecules enrichment. We hope that the data presented here might catalyze further research to translate these observations into clinical enhancements in NIPT.

A. Advantages of Cell-Free DNA Repair in Molecular Diagnostics

DNA damage is introduced to cells during multiple cellular processes, such as metabolic activities and DNA replication during cell proliferation. In most occasions, cells are able to identify types of DNA damages and tackle them by different types of DNA damage repair processes. For irreparable DNA damages, cells are fated to undergo apoptosis to prevent from accumulation of carcinogenic mutations. It is believed that apoptosis and necrosis are two of the major sources of cell-free DNA (cfDNA) present in the circulation.[10,27,40] Similar to the genomic DNA, there are multiple types if cfDNA damages, namely DNA physical breakages such as DNA nicks, gaps and double strand breaks formation, modifications of DNA molecules such as oxidation, hydrolysis such as deamination, loss of DNA bases and pyrimidine-dimer formation. Such DNA damages may decrease cfDNA integrity and may cause suboptimal effects to downstream analyses in molecular diagnostics, such as Next-Generation Sequencing (NGS), quantitative PCR (qPCR), size profile characterization, etc.

Most of cfDNA fragments have a peak size of 166 bp, resembling a 146-bp mononucleosomal structure plus 20-bp linker regions. Beside these major cfDNA species, there are minor cfDNA species with longer length, ranging from 166 bp to over 600 bp. Such rare cfDNA species may carry valuable information as important as those shorter ones. However, due the limitation of size range detection of current Next-Generation Sequencing (NGS) platforms, the detection of such long cfDNA species requires extra high throughput to achieve reasonable sequencing coverages, which is impractical and cost ineffective. Despite the technical obstacles, the read length limitation has somehow been partially compromised by recent third-generation Single Molecule Real-Time (SMRT) sequencing, in which super high read length (>20 kb) can be produced from a single circulated cfDNA molecule. But still, the exploration of extra-long cfDNA species in the circulation remains to be a difficult task.

In contrast, cfDNA repair is a relatively cost-effective, quick and user-friendly method to achieve long cfDNA enrichment without altering sequencing throughput and sequencing library structure. Currently, one DNA repair kit is PreCR Repair Mix by New England Biolabs. PreCR Repair Mix is capable to repair a variety of naturally-occurred DNA damages, such as abasic hydrolysis, nicks, basic oxidation and thymidine dimerization.[41] However, it cannot repair DNA fragmentation and DNA-protein cross-links.

B. Cell-Free DNA Repair for Detecting Fetal Trisomy

The ability of the PreCR repair mix to restore damaged DNA opens up many potential applications. In prenatal diagnosis, our data (e.g., FIG. 16) demonstrated that PreCR repair treatment may contribute to improved NIPT performance for trisomy 21 screening. Z-scores of repaired trisomy 21 samples were better separated from those of the repaired euploid samples. This is especially important for a case where the Chr21 z-score is borderline and close to the euploid-aneuploid cutoff without repair treatment. Combinational simulation and ROC analyses further confirmed such NIPT improvement could significantly increase the sensitivity as well as the specificity of the test. Beyond enhancing the statistical confidence of discrimination of euploidy and aneuploidy, repair of cfDNA may improve the call rate of NIPT. In particular, scenarios with non-reportable NIPT results caused by insufficient fetal DNA fraction[9-13] or poor cfDNA quality might be improved by DNA repair.

C. Cell-Free DNA Repair to Assess SLE

SLE is a systematic autoimmune disease which can cause chronic inflammations at multiple sites, resulting to tissue damage and organ failure. Examples of such are renal complications, infections, and myocardial infarctions.[14] SLE has also been reported to be associated with the elevations of cfDNA in plasma.[15,16] It has also been reported that SLE patients have a higher proportion of cfDNA with size shorter than 115 bp.[8] The amount of such cfDNA molecules in the plasma of active SLE patients was threefold higher than that of healthy individuals.[8] The elevation of these shorter (<115 bp) cfDNA molecules was more pronounced in active SLE patients compared to that in inactive SLE patients.[8] Therefore, the ability of cfDNA quality improvement by PreCR Repair Mix might cause an impact in size profiles of these cfDNA molecules in SLE patients. The observation that PreCR repair treatment enriched longer (>250 bp) cfDNA molecules without significantly losing shorter (<166 bp) ones suggests that most reparable cfDNA molecules are longer than 250 bp. The enriched extra short cfDNA (<115 bp), which is a feature of severe SLE patients,[8] are generally irreparable by PreCR Repair Mix. PreCR treatment repairs DNA fragments, allowing for more fragments to be analyzed for SLE or other conditions. Further investigations needed to reveal the nature of DNA damages carried by such cfDNA molecules. For diagnostic purposes, a better separation between inactive and active SLE samples after PreCR repair treatment improves SLE assessment.

D. Potential Applications of cfDNA Repair

DNA repair can be applied before a wide range of DNA assays and molecular tests, such as DNA fingerprinting in forensics, DNA archaeological samples retrieval for taxonomy and species classification, DNA recovery from old, archival FFPE samples, etc. In the cfDNA field, repair-pretreated cfDNA may increase NIPT accuracy and sensitivity. In particular, situations with uninformative NIPT test results contributed by low cfDNA input or poor cfDNA quality could be improved by increasing intact, assayable fetal DNA in the maternal plasma. Examples of such conditions would be NIPT in first trimester pregnancies and obese pregnancies, where the fetal cfDNA are sparse and difficult to be assayed. Furthermore, by applying cfDNA repair into present haplotype-based NIPT protocols using Single Nucleotide Polymorphism (SNP),[18,42,43] detection and identification of special pregnancy conditions such as monogenic diseases, vanishing twin and triploid pregnancy would be more efficient and accurate.

E. Extended Application of cfDNA Repair Beyond Present Detection Limits

The ability of cfDNA repair to visualize long cfDNA fragments in the circulation opens up a potential extended application of molecular diagnostics on various diseases. In one example, detection of long tandem repeats and repeated microsatellites species in the circulation of patients carrying suspected triplet repeat disorders was difficult and tedious, as those species are extremely sparse and heavily damaged. This results indifficulty of molecular diagnostics of such diseases by NIPT. However, with the advantages of cfDNA repair, the detection of such long tandem repeats and microsatellite species could be plausible.

Figure 26:
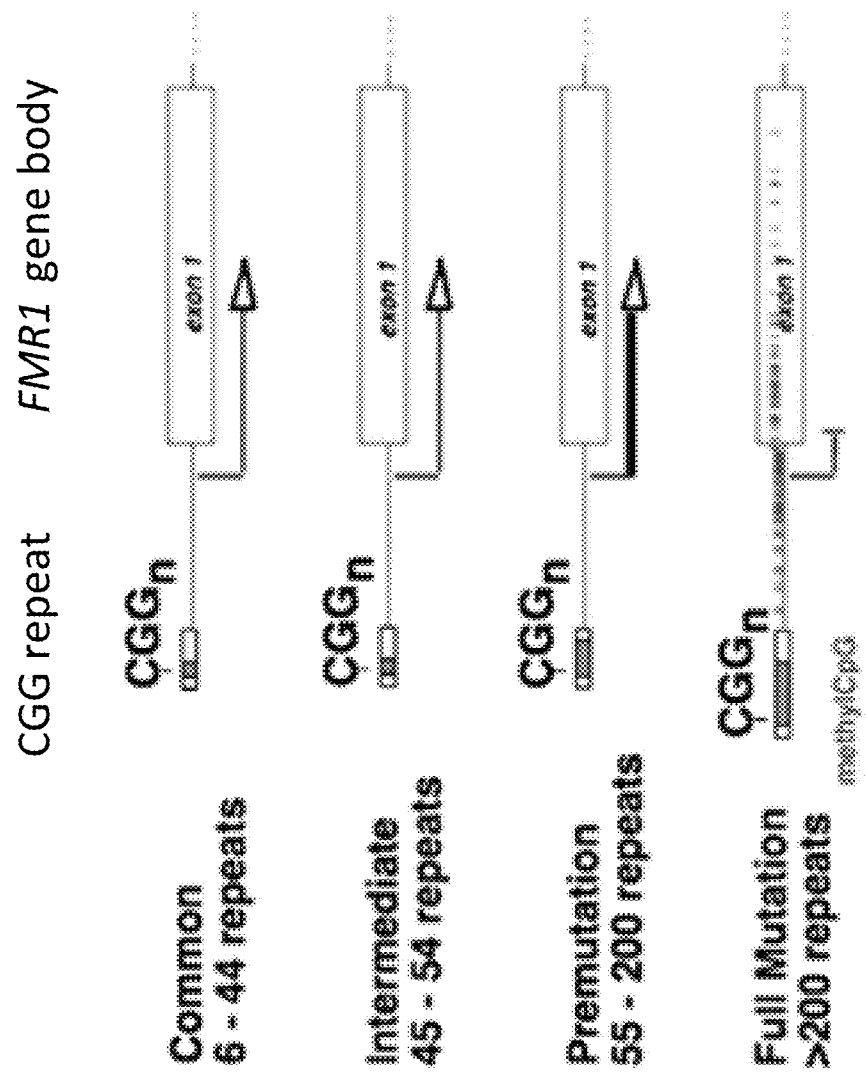
FIG. 26 shows the presence of CGG triplet repeat cfDNA fragments in patients with Fragile-X Syndrome (FXS) according to embodiments of the present invention.

FIG. 26 shows the presence of CGG triplet repeat cfDNA fragments in patients with Fragile-X Syndrome (FXS), where the length of the fully mutated FMR1 alleles can reach up to 600 bp or more (Garber, Kathryn B., Jeannie Visootsak, and Stephen Warren T., "Fragile X Syndrome," Nature.com, Nature Publishing Group, 9 Apr. 2008. Web. 9 Sep. 2016). The CGG repeat number may exceed 200 in fully mutated (pathogenic) FMR1 allele. Traditionally, prenatal diagnosis of FXS remains invasive; expanded CGG tandem repeats of FMR1 is detected by Triplet repeat Primed-PCR (TP-PCR) coupled with confirmation by Southern blot hybridization.[44,45]

Diagnosis of FXS using NIPT is restricted by the cfDNA length detection limit. Indeed, NIPT diagnosis of FXS requires considerable integrity of the expanded FMR1 alleles to be sequenced, the longer the CGG tandem repeat is from a fully mutated FMR1 allele, the heavier it is damaged. A screening approach focusing on the relative methylation status of FMR1 promoter region[46] allows NIPT of FXS. Researchers of this work discovered a distinct DNA-methylation boundary at locus upstream of FMR1, which protects the spreading of DNA methylation from the upstream terminus to the gene promoter and gene body of FMR1. They also discovered that this boundary is disrupted and methylation is penetrated into the FMR1 promoter, which caused FMR1 silencing. With cfDNA repair, enriched cfDNA fragments from hyper- or hypomethylated FMR1 promoter with its proximal upstream terminus would accurately detect the DNA-methylation boundary and increase NIPT successful rate of FXS.

In another example, cfDNA repair is also applicable into assays where sufficient amount of cfDNA fragments with considerable length is necessary. One example would be allele haplotyping of HLA and HBB genes, both which are highly polymorphic with concentration of tandem SNP clusters. The relative short inter-SNP distances in the HLA and HBB loci allow potential haplotyping possibility, using cfDNA with linked and proximal tandem SNPs present in the circulation. HLA typing is a critical step before matching donors and recipients in cord blood and bone marrow transplants. Mismatched HLA pairing may result in post-transplant complications called graft-versus-host (GVHD) disease. Importantly, the successful detection of tandem SNPs within a target gene locus depends on existence of intact, assayable cfDNA fragments.

Figure 27:
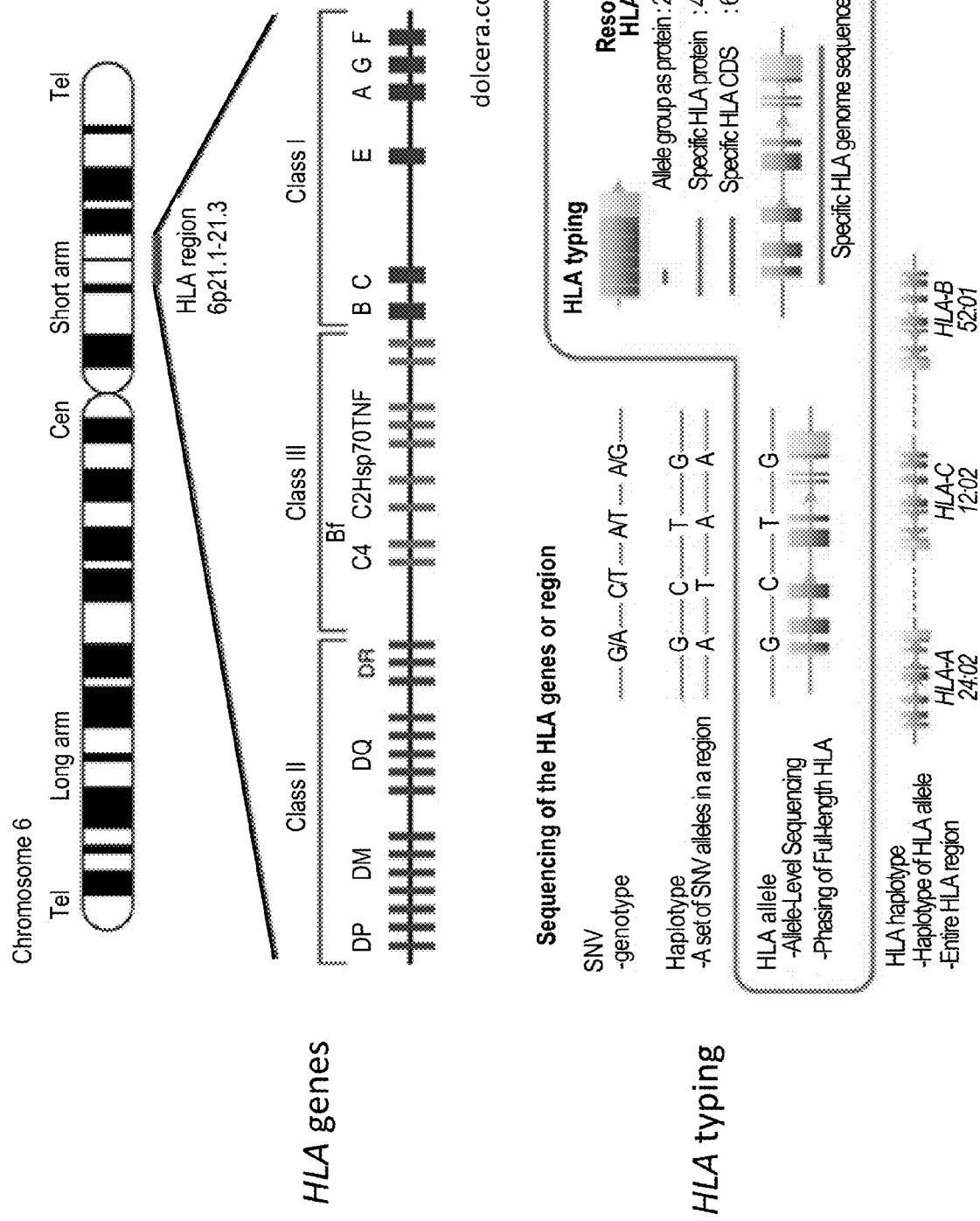
FIG. 27 shows shows allele haplotyping of the HLA gene according to embodiments of the present invention.

FIG. 27 shows allele haplotyping of the HLA gene. The HLA region covers the HLA region of the short arm of chromosome 6. Haplotyping the HLA gene uses a long length of DNA in order to identify the specific HLA genome sequence.[47] Longer DNA fragments covering multiple HLA genes aids accurate haplotyping with correct linkage.

Figure 28:
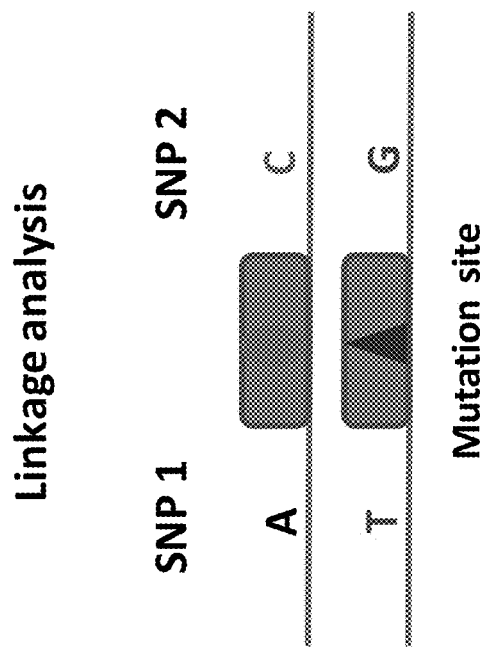
FIG. 28 shows linkage analysis for Congenital adrenal hyperplasia (CAH), according to embodiments of the present invention.

The feasibility of such haplotyping method can also be further applied to haplotyping of other monogenic diseases, such as Congenital adrenal hyperplasia (CAH). FIG. 28 shows linkage analysis for CAH. CAH is an autosomal recessive disorder arising from mutations of the CYP21A2 gene. Linkage analysis can be achieved by locating and connecting 2 proximal SNPs flanking the mutated site.[18] This linkage analysis is facilitated by using longer lengths of DNA. The distance between the mutation site and a nearby SNP varies, depending on the particular SNP density of the genomic region of the mutation. The closer the distance between the mutation site and nearby SNP likely will result in a better outcome, as cfDNA is highly fragmented in the maternal circulation. In the case of linkage analysis, a long cfDNA covering the mutation site and both flanking SNPS provides linkage haplotype information.

In another example, cfDNA repair can facilitate the real-time monitoring of various disease conditions in the course of treatments. Importantly, tissue mapping by differential cfDNA methylation signatures measurements provides a powerful tool for the detection of cfDNA origins.[48,49] In pregnancy-related conditions such as pre-eclampsia and trophoblastic dysplasia, the real-time detection of placental-derived cfDNA in maternal plasma becomes a powerful monitoring tool. Any relapse of a disease or disorder might be immediately detected and tackled for optimal treatment. For post-transplantation recipients, similar real-time tissue mapping can be applied for more effective monitoring for possible organ rejections. However, in the course of DNA bisulfite modification of sequencing library, a critical step of the bisulfite sequencing protocol, generates extrinsic DNA damages on sequencing library. Such damages might decrease the sensitivity of tissue mapping by converting sequencible fragments into uninformative species. A possible extra repair treatment after bisulfite treatment manages to rescue those damaged bisulfite-converted fragments into intact, sequencible species.

In another example, detection of reparability of cfDNA may assist with the detection, assessment, and monitoring of disease progression of conditions associated with cfDNA damage, for example autoimmune disorders and inflammatory conditions. Particularly, the amount of cfDNA damage can be deduced by differences between repaired samples and their non-repair controls; i.e. a higher sham-repair difference may reflect a higher content of cfDNA damage. In autoimmune and inflammatory conditions, such as systemic lupus erythematosus (SLE), the proportion of extra-short cfDNA molecules (115 bp) is much higher than that of healthy individuals. Progression of the disease (from inactive to active form) is correlated with the increase of such extra-short cfDNA molecules.[50] We suspect that the extent and the nature of DNA damage in these diseases, especially in the severe or active form would be different also.

The detection of the extent of cfDNA damage, or conversely, the extent of reparability would allow the detection and assessment of such diseases. The higher the extent of DNA damage or the higher degree of reparability would reflect the existence of such diseases or high activity or higher severity of the disease. The measurement of the extent of reparability could be based on comparing the amount of various sized DNA molecules with or without DNA repair. In addition, assessment of the extent of DNA damage could be based on comparing the extent of DNA repair (the difference between the addition and the omission of the repair step) between the test sample and a control sample collection from a person without the disease or with a mild form of the disease. Such parameters can be generalized for the characterization of cfDNA damage. Similarly, the quality of any cfDNA/gDNA/ctDNA sample can also be assessed by the measurement of DNA reparability, prior to any downstream analysis or assay. For example, samples with high DNA reparability indicate poor DNA quality, and an additional repair treatment step may be recommended prior to downstream protocols, such as sequencing library preparation.

DNA damages can be also acquired and accumulated in a time-dependent manner. The longer a DNA fragment is released and stay in the circulation, the more chance it acquires and accumulates DNA damages. Therefore, real-time monitoring of the degree of DNA damages could be a potential approach of therapeutic efficiency.

F. cfDNA Repair as a Valuable Tool for Molecular Diagnostics

As different cell types in the micro-environment of a certain tissue have different metabolic turnover rates, different tissues may have their unique "damage signatures." Different cfDNA may be released from different damaged tissues. By tissue mapping (Sun et al., PNAS 2015), the origins of cfDNA can be traced and identified. The tissue mapping may be done in parallel with the quantification of cfDNA damage in circulation (e.g., using labelled dNTPs). As a result, a dynamic "damage signature" from a certain organ in a period of time may then be deduced and detected.

Another major issue of cfDNA repair development in the future would be the variety of repairable DNA. Currently, there are a number of DNA damages that cannot be reversed, namely DNA fragmentation and DNA-protein crosslinking. This is because the repair of DNA fragmentation, which is a type of double-strand break (DSB), requires a series of repair complex proteins to undergo non-homologous end joining (NHEJ) in the biological condition. The current commercial repair reaction, however, does not contain such repair complex. Therefore, repair of DNA fragmentation remains a current challenge. In resolving this, it could be plausible of spiking-in NHEJ proteins needed for DSB repair, such as Mre11-Rad50-Nbs1 (MRN) complex and Ku-DNA-PKcs complex. The DNA phasing issues after DSB repair could be resolved by bioinformatic means through a molecular barcoding system designed in between conventional DNA repair and DSB repair steps.

In contrast to DNA fragmentation, DNA crosslinkages such as inter-strand crosslinking and DNA-protein crosslinking are much more difficult to repair. The strong adherent force of covalent bonds in between DNA strand and proteins makes it very difficult to break. Due to the nature that a vast diversity of DNA binding proteins is present in the vicinity of circulation, it is possible that a portion of them can form DNA-protein crosslinks very easily. If this happens to the major plasma proteins, such as human serum albumin (HSA), that would result a vast amount of cfDNA being crosslinked to HSA which are hardly accessible without the procedure of reverse crosslinking. Therefore, it would be an intrinsic need to break the cfDNA-protein crosslinks and release those cfDNA molecules free to be downstream assayed. To encounter this, reverse crosslink steps should be designed and included in the DNA repair procedures.

Beside DNA damage type characterization, damage location on the cfDNA molecule might also be a piece of valuable information in future molecular diagnostics. It is important that the DNA damages patterns are traceable; knowing the exact positions of DNA damages on cfDNA molecules would be useful to deduce the source of such damages. However, there are a number of challenges to be overcome in the development of such "repair-based liquid biopsy" method. Firstly, without the known nicking patterns and cutting overhangs of multiple nucleases, it is impossible to deduce damage-initiating machineries retrospectively by surveying the entire pool of cfDNA damage types present in the circulation. For example, typical nucleases responsible for cfDNA fragmentation, such as DNaseI and DNase1-like-3, do not contain consensus cutting sites. These enzymes tend to cut DNA molecules in a randomized manner. Conversely, these enzymes have their unique attacking patterns on DNA molecules; DNase1 tends to attack and cut naked DNA molecules where DNase1-like-3 tends to generate multi-nucleosomal patterns.[51]

Secondly, the buildup of an atlas of all damage-containing cfDNA fragments with their exact damage locations will be necessary for molecular diagnostics development. With the advantage of cfDNA repair to recover long cfDNA fragments, it is possible to detect the previously undiscovered cfDNA species, with large gaps in the middle of one strand and extra-long overhangs on the other strand. Likewise, cfDNA molecules with combinations of multiple damage types can also be systematically revealed, provided the damages are repairable.

Thirdly, tracing repaired cfDNA molecules in the mist of out-numbered intact cfDNA molecules could be a resolved by spiking in labeled and non-toxic dNTPs. Labeled dNTPs may be used to repair the defects. The degree of damage could be calculated by the ratio of unlabeled and labeled dNTPs in a single cfDNA molecule. This is particularly useful in the continuous monitoring of disease progress and therapeutic effectiveness by the measurement of the repair dynamics. In conclusion, the ultimate goal for cfDNA in molecular diagnostics is, almost surely, the "hunt" of novel class of undiscovered, damaged cfDNA molecules in the circulation will be possible with the improving of DNA repair technologies.

IV. Example Methods

A. Improving Cell-Free Nucleic Acid Quality

Figure 29:
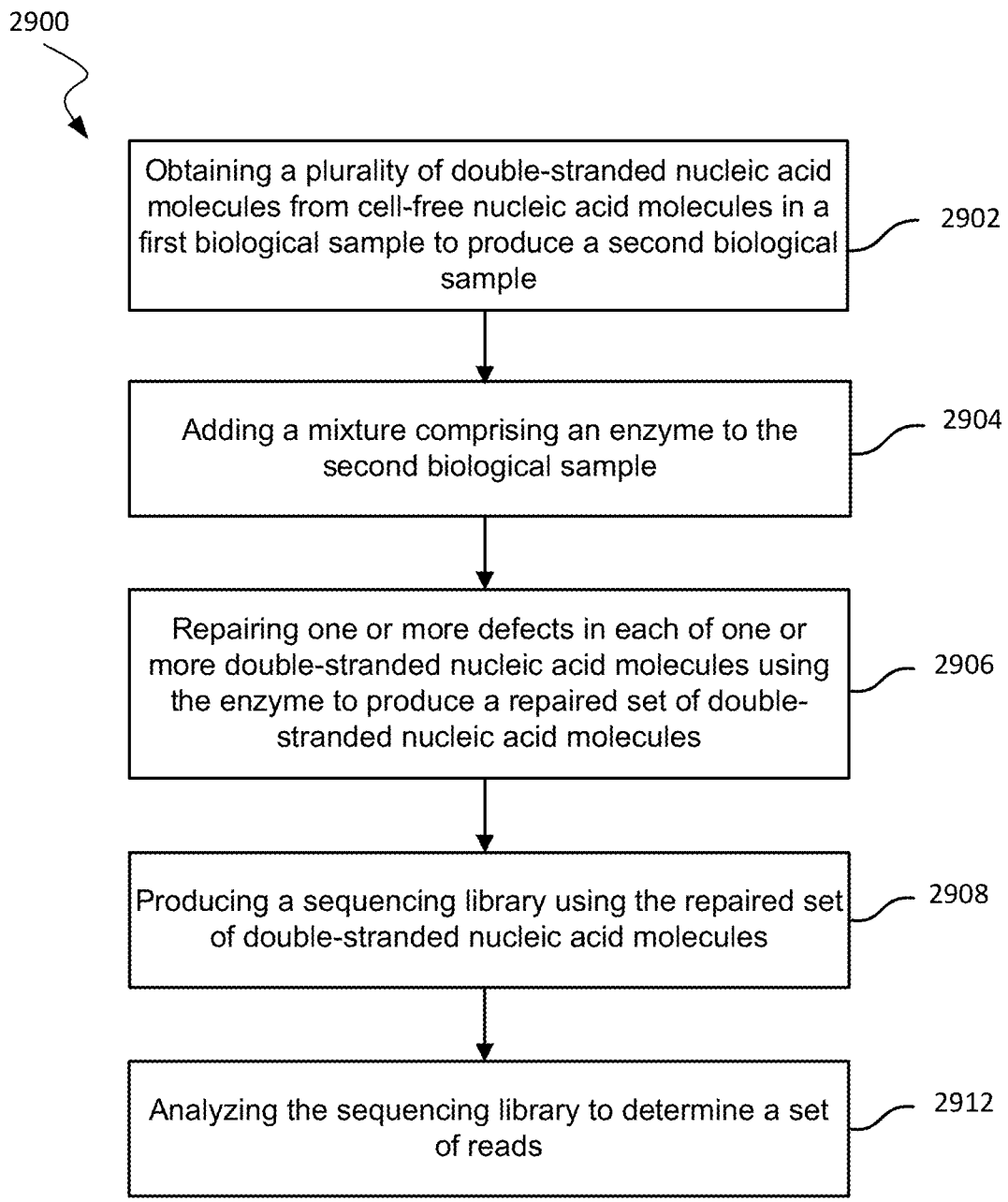
FIG. 29 shows a method of preparing a sequencing library of a biological sample according to embodiments of the present invention.

FIG. 29 shows a method 2900 of improving analysis of a first biological sample. The first biological sample may include cell-free nucleic acid molecules. The first biological sample may include maternal plasma from a female subject pregnant with a fetus or plasma from a subject having a disorder or suspected to have a disorder. Plasma may be extracted from a blood sample. The first biological sample may be a sample before any component not derived from the subject or the fetus of the subject is added.

At block 2902, the double-stranded nucleic acid molecules may be obtained from the cell-free nucleic acid molecules to produce a second biological sample. One or more double-stranded nucleic acid molecules of the plurality of double-stranded nucleic acid molecules each has one or more defects. For each of the one or more double-stranded nucleic acid molecules having a defect of the one or more defects, the defect is present in the respective double-stranded nucleic acid molecules at a location at least one nucleotide away from the closest end of the respective double-stranded nucleic acid molecule. In other words, the defect may be an intrastrand defect and not a defect at either end of either strand of the double-stranded nucleic acid molecule. In some embodiments, the defect may be at a location 2, 3, 4, 5, 10, 15, 20, 25, or 30 or more nucleotides away from the closest end of the respective double-stranded nucleic acid molecule.

The one or more defects may include a defect or defects selected from the group consisting of a nick, gap, abasic site, thymidine dimer, oxidized pyrimidine, deaminated cytosine, blocked 3' end defect, or a combination thereof.

The one or more double-stranded nucleic acid molecules may have lengths in a range from 251 to 600 bp, from 251 to 450 bp, or from 451 bp to 600 bp. The lengths may be associated with di-nucleosomal or tri-nucleosomal nucleic acid molecules.

At block 2904, a mixture including an enzyme may be added to the second biological sample. The enzyme may include at least one of a polymerase, a ligase, an endonuclease, or a glycosylase. The mixture may include at least one enzyme of Taq DNA polymerase, Bst DNA polymerase, Taq DNA ligase, endonuclease VIII, endonuclease IV, T4 endonuclease V (PDG), 8-oxoguanine glycosylase (FPG), or uracil-DNA glycosylase (UDG). In some embodiments, the mixture may include Taq DNA polymerase, Bst DNA polymerase, Taq DNA ligase, endonuclease VIII, endonuclease IV, T4 endonuclease V (PDG), 8-oxoguanine glycosylase (FPG), and uracil-DNA glycosylase (UDG). The mixture may also include any combination of $NAD^+$, ThermoPol Reaction Buffer, and deoxynucleoside triphosphates (dNTPs).

At block 2906, one or more defects in each of the one or more double-stranded nucleic acid molecules may be repaired using the enzyme to produce a repaired set of double-stranded nucleic acid molecules. The repaired set of double-stranded nucleic acid molecules may be free of the one or more defects, including any defect described herein. Repairing the one or more defects may include repairing a greater number of nucleic acid molecules having lengths from 251 to 600 bp than nucleic acid molecules having lengths from 0 to 250 bp. In other words, more defects may be repaired from dinucleosomal and/or trinucleosomal nucleic acid molecules than from mononucleosomal nucleic acid molecules.

For a biological sample containing clinically-relevant DNA (such as fetal DNA), repairing defects in the one or more double-stranded nucleic acid molecules may raise the fraction of the clinically-relevant DNA to allow for further analysis. For example, if the first biological sample is obtained from a female subject pregnant with a fetus, the one or more double-stranded nucleic acid molecules with defects may include a plurality of fetal-derived nucleic acid molecules. After repairing the one or more defects, the second biological sample may be characterized by a fetal fraction calculated from reads obtained from analyzing the repaired set of double-stranded nucleic acid molecules. The fetal fraction may be greater than a threshold fraction preferred or needed for further analysis. For example, the fetal fraction after repair, may be greater than or equal to 0.01, 0.02, 0.03, 0.04, 0.05, 0.06, 0.07, 0.08, 0.09, or 0.10. The fetal fraction after repair may be calculated from reads to be greater than a fetal fraction calculated from reads before repair. The actual fraction of DNA from the fetus may not change, however. Instead, the calculated fetal fraction may increase after repair because reads of fetal-derived DNA may be obtained only after repair.

Methods may include performing blunt-end ligation of the plurality of double-stranded nucleic acid molecules or of the repaired set of double-stranded nucleic acid molecules. Blunt-end ligation is not the repair of the one or more defects in block 2906 because blunt-end ligation addresses nucleotides at the end of the double-stranded nucleic acid molecule, not intrastrand defects.

At block 2908, a sequencing library may be produced using the repaired set of double-stranded nucleic acid molecules. The repaired set of double-stranded nucleic acid molecules is subjected to sequencing library preparation procedures, including end repairing, A-tailing, sequencing adaptor ligation, and indexed PCR amplification.

At block 2912, the sequencing library may be analyzed to determine a set of reads. In some embodiments, at least 1,000 cell-free DNA molecules are analyzed. In other embodiments, at least 10,000 or 50,000 or 100,000 or 500,000 or 1,000,000 or 5,000,000 cell-free DNA molecules or more can be analyzed. The set of reads may be determined by sequencing the sequencing library. Sequencing techniques may include paired-end sequencing, massively parallel sequencing, single molecule real-time (SMRT) sequencing, PCR, reverse transcription PCR (RT-PCR), digital PCR, or sequencing. In some embodiments, the set of reads may be determined by performing targeted capture enrichment. The set of reads may not include reads from double-stranded nucleic acid molecules having one or more defects. For example, the set of reads may not include reads from either single-stranded nucleic acid molecules from the double-stranded nucleic acid molecules having one or more defects. In some embodiments, the set of reads may be from only one strand of the double-stranded nucleic acid molecules. In other embodiments, the set of reads may be from both strands of the double-stranded nucleic acid molecules.

Methods may include using the sequencing library prepared using the repaired set of double-stranded nucleic acid molecules. Methods may include detecting an aneuploidy in a fetus from a maternal plasma sample. In some embodiments, methods may include detecting a sequence imbalance. Methods may include detecting a microamplification or microdeletion in a fetus. In addition, methods may include detecting any disorder described herein.

For example, a method may include determining whether a sequence imbalance exists in the second biological sample. A plurality of sequence reads from the repaired set of double-stranded nucleic acid molecules may be obtained. The plurality of sequence reads may be analyzed by a computer system. Analyzing a sequence read may include identifying a location of the sequence read in a reference genome by aligning the sequence read to the reference genome. The amount of sequence reads from a genomic region using the identified locations may be determined by a computer system. The value of a normalized parameter for the amount of sequence reads from the genomic region may be obtained. The value of the normalized parameter may be compared to a cutoff value. Whether the sequence imbalance exists may be determined based on the comparison. The genomic region may be a chromosome, and the sequence imbalance may be an aneuploidy.

The repaired set of double-stranded nucleic acid molecules may be used for methods where having longer nucleic acid molecules is preferred. For example, the repaired set of nucleic acid molecules may be used to determine a classification whether Fragile-X Syndrome (FXS) exists using a first biological sample from a female subject pregnant with a fetus. The method may include enriching the repaired set of double-stranded nucleic acid molecules from the FMR1 promoter region and the proximal upstream terminus of the FMR1 promoter to form an enriched set of double-stranded nucleic acid molecules. A methylation-aware assay may be performed on the enriched set of double-stranded nucleic acid molecules. In some embodiments, the methylation-aware assay may include bisulfite sequencing. A plurality of sequence reads from the enriched set of double-stranded nucleic acid molecules may be obtained. The plurality of sequence reads may be aligned to a reference genome. The presence or absence of a DNA-methylation boundary indicative of FXS at a location upstream of the FMR1 promoter is detected using the aligned sequence reads. The classification may be that FXS exists when the DNA-methylation boundary is absent.

Methods may include haplotyping the repaired set of double-stranded nucleic acid molecules. The HLA gene may be haplotyped. A monogenic disease may be haplotyped by obtaining a plurality of sequence reads from the enriched set of double-stranded nucleic acid molecules. The plurality of sequence reads may be aligned to a reference genome. A mutation may be identified at a locus between two proximal SNP using the aligned plurality of sequence reads. The monogenic disease may be congenital adrenal hyperplasia.

B. Classifying a Disorder

Figure 30:
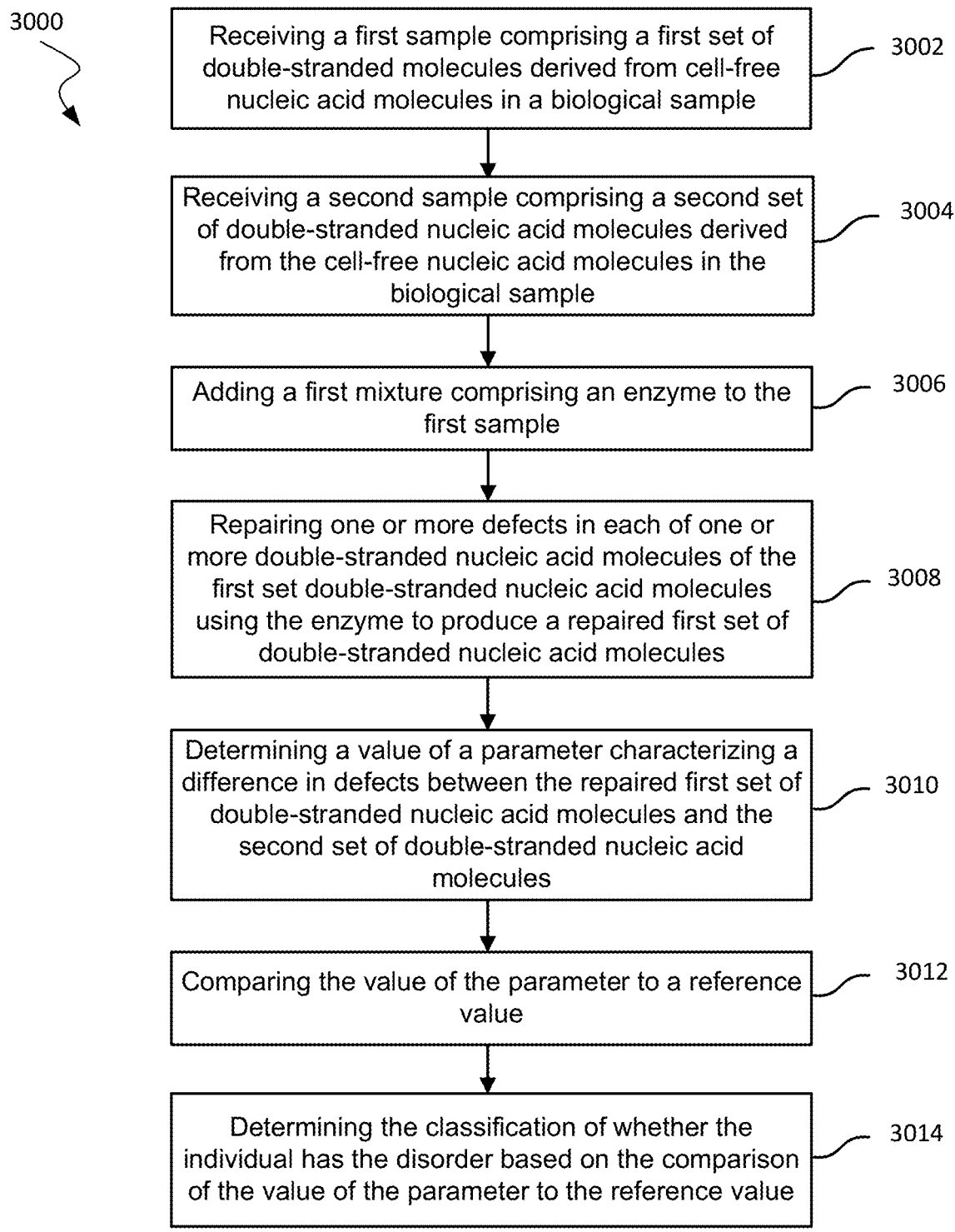
FIG. 30 shows a method of determining a classification of whether an individual has a disorder according to embodiments of the present invention.

FIG. 30 shows a method 3000 of determining a classification of whether an individual has a disorder. The disorder may include systemic lupus erythematosus (SLE), congenital adrenal hyperplasia (CAH), Fragile-X Syndrome, graft-versus-host (GVHD) disease, pregnancy-related disorder (e.g., pre-eclampsia and trophoblastic dysplasia), aneuploidy, sequence imbalance, or any disorder described herein.

At block 3002, a first sample may be received. The first sample may include a first set of double-stranded nucleic acid molecules derived from cell-free nucleic acid molecules in a biological sample. The biological sample may be any biological sample described herein. The one or more double-stranded nucleic acid molecules of the first set of double-stranded nucleic acid molecules may each have one or more defects. The one or more defects may be present in the respective double-stranded nucleic acid molecule at a location at least one nucleotide away from a closest end of the respective double-stranded nucleic acid molecule. The one or more defects may be any defects described herein.

At block 3004, a second sample may be received. The second sample may include a second set of double-stranded nucleic acid molecules derived from the cell-free nucleic acid molecules in the biological sample. As an example, the first sample and the second sample may be prepared by dividing a biological sample into two samples. In some embodiments, the first sample and the second sample may be equal in volume, where equal can include volumes that differ within experimental error. The first sample may have a volume within 5%, 10%, or 15% of the volume of the second sample.

At block 3006, a first mixture including an enzyme may be added to the first sample. The first mixture and the enzyme may be any mixture and enzyme described herein. For example, the mixture may include a plurality of enzymes described herein.

At block 3008, one or more defects in each of the one or more double-stranded nucleic acid molecules of the first set of double-stranded nucleic acid molecules may be repaired using the enzyme. A repaired first set of double-stranded nucleic acid molecules may be produced from the repair.

The second sample may be formed from a third sample comprising a third set of double-stranded nucleic acid molecules. A second mixture may be added to the third sample to produce the second set of double-stranded nucleic acid molecules. The second mixture may exclude the enzyme. For example, the second mixture may be a sham mixture that includes components of the first mixture except for the enzyme or enzymes that repair intrastrand defects. The second set of double-stranded nucleic acid molecules may be the same or different from the third set of double-stranded nucleic acid molecules. In other embodiments, the second sample does not have the sham mixture added to it.

At block 3010, a value of a parameter characterizing a difference in defects between the repaired first set of double-stranded nucleic acid molecules and the second set of double-stranded nucleic acid molecules may be determined.

The value of the parameter may be determined using the reads determined from the repaired first set of double-stranded nucleic acid molecules and the second set of double-stranded nucleic acid molecules. For example, methods may include sequencing or performing targeted capture enrichment of the repaired first set of double-stranded nucleic acid molecules to determine a first set of reads. Methods may also include sequencing or performing targeted capture enrichment of the second set of double-stranded nucleic acid molecules to determine a second set of reads. The first set of reads and the second set of reads may not include reads from double-stranded nucleic acid molecules having one or more defects. Damaged DNA fragments that survive the end repairing process may be subject to cluster formation (one of the steps of Illumina-based sequencing). Damaged DNA may cause failed cluster formation, resulting in PCR failure or DNA polymerase stalling. Mismatches may also occur when a nucleotide substitution occurs, which results in a sequencing error. The first set of reads may have a first amount of reads. The second set of reads may have a second amount of reads.

The value of the parameter may be determined using the first amount of reads and the second amount of reads. For example, the value of the parameter may be determined using a difference between the first amount of reads and the second amount of reads. In other embodiments, the value may be determined using a ratio of the first amount of reads and the second amount of reads. The ratio may be calculated using the first amount divided by the second amount, the second amount divided by the first amount, the first amount divided by the sum of the first amount and the second amount, or the second amount divided by the sum of the first amount and the second amount. In some embodiments, the amount of reads may be limited to reads for a certain size range or a certain genomic location. The amounts of reads may be a normalized amount of reads (e.g., a percentage, a fraction, or a concentration).

The value may be determined from statistical values describing the size of the sets of reads. Methods may include calculating a first statistical value characterizing the sizes of the first set of reads and calculating a second statistical value characterizing the sizes of the second set of reads. The statistical value may be a median, mode, mean, or a percentile describing the sizes of the nucleic acid molecules of the sets of reads. The value may be determined using the first statistical value and the second statistical value. For example, the value may be a difference between the statistical values or a ratio of the statistical values.

The parameter may be multidimensional. A first dimension of the parameter may be based on a size of a nucleic acid molecule. The first dimension may be a range of sizes. In other embodiments, the first dimension may be a range of ratios of the size of the nucleic acid molecule to a reference size. A second dimension of the parameter may include an amount of the nucleic acid molecule. For example, the parameter may be a matrix of the amount of nucleic acid molecules for certain sizes of nucleic acid molecules. As another example, the parameter may be a graph (e.g., histogram) of the amounts of nucleic acid molecules for certain sizes of nucleic acid molecules.

In some embodiments, the first dimension of the parameter may include a location in a reference genome of a nucleic acid molecule. The second dimension may include an amount of the nucleic acid molecule. The parameter may then describe the amounts of nucleic acid molecules at certain locations in the reference genome.

The reference value may also be multidimensional. The reference value may specify an amount of nucleic acid molecules at different sizes of the nucleic acid molecules. The reference value may be threshold amounts at different sizes or a certain pattern of amounts among different sizes (e.g, amounts should peak at a certain size). In some embodiments, the reference value may specify an amount of nucleic acid molecules at certain locations in the reference genome. These genomic locations may be may correspond to locations between nucleosomes. The reference value may be determined using one or more subjects identified to have or not have the disorder.

At block 3012, the value of the parameter may be compared to a reference value. Comparing the value of the parameter may include determining whether the value of the parameter exceeds the reference value (e.g., the value of the parameter being more positive or more negative than the reference value). The reference value may be a threshold value.

At block 3014, a classification of whether the individual has the disorder may be determined based on the comparison of the value of the parameter to the reference value. A level or severity of the disorder may be determined by the comparison. The severity may depend on the difference between the value of the parameter and the reference value. A greater difference may mean a more severe disorder. The disorder may be classified as more severe when the difference is greater than a cutoff value. Several cutoff values may be used, with each cutoff value associated with a different severity.

In some embodiments, methods may include treating the specific disorder upon classifying that the individual has the disorder or the individual has a high likelihood of having the disorder. Embodiments may include treating the disease or condition in the patient after determining the level of the disease or condition in the patient. Treatment may include any suitable therapy, drug, or surgery, including any treatment described in a reference mentioned herein. Information on treatments in the references are incorporated herein by reference.

V. Example Systems

Figure 31:
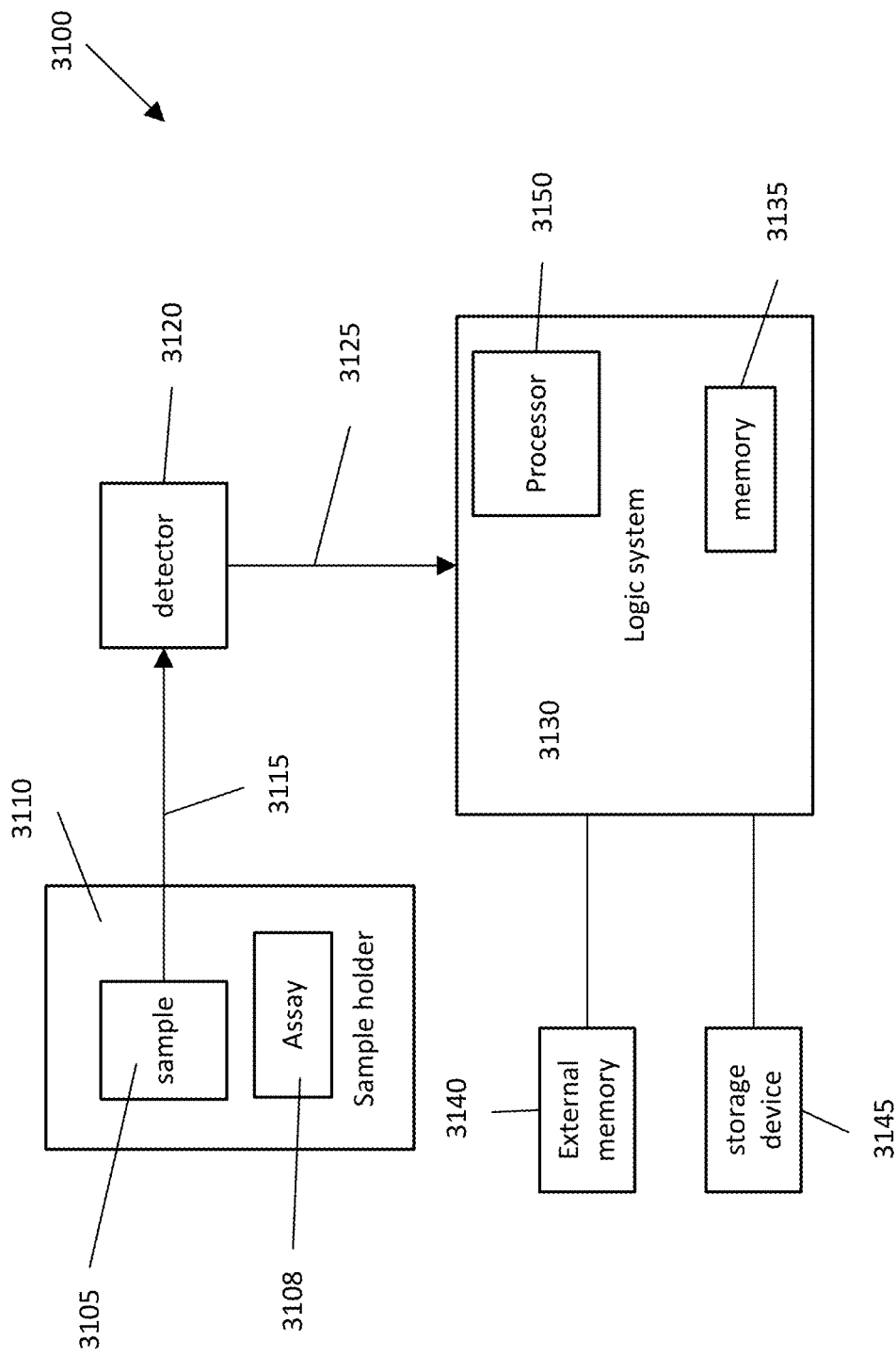
FIG. 31 illustrates a system according to embodiments of the present invention.

FIG. 31 illustrates a system 3100 according to an embodiment of the present invention. The system as shown includes a sample 3105, such as cell-free DNA molecules within a sample holder 3110, where sample 3105 can be contacted with an assay 3108 to provide a signal of a physical characteristic 3115. In some embodiments, sample 3105 may be a single cell with nucleic acid material. An example of a sample holder can be a flow cell that includes probes and/or primers of an assay or a tube through which a droplet moves (with the droplet including the assay). Physical characteristic 3115, such as a fluorescence intensity value, from the sample is detected by detector 3120. Detector can take a measurement at intervals (e.g., periodic intervals) to obtain data points that make up a data signal. In one embodiment, an analog to digital converter converts an analog signal from the detector into digital form at a plurality of times. A data signal 3125 is sent from detector 3120 to logic system 3130. Data signal 3125 may be stored in a local memory 3135, an external memory 3140, or a storage device 3145.

Logic system 3130 may be, or may include, a computer system, ASIC, microprocessor, etc. It may also include or be coupled with a display (e.g., monitor, LED display, etc.) and a user input device (e.g., mouse, keyboard, buttons, etc.). Logic system 3130 and the other components may be part of a stand-alone or network connected computer system, or they may be directly attached to or incorporated in a thermal cycler device. Logic system 3130 may also include optimization software that executes in a processor 3150.

Figure 32:
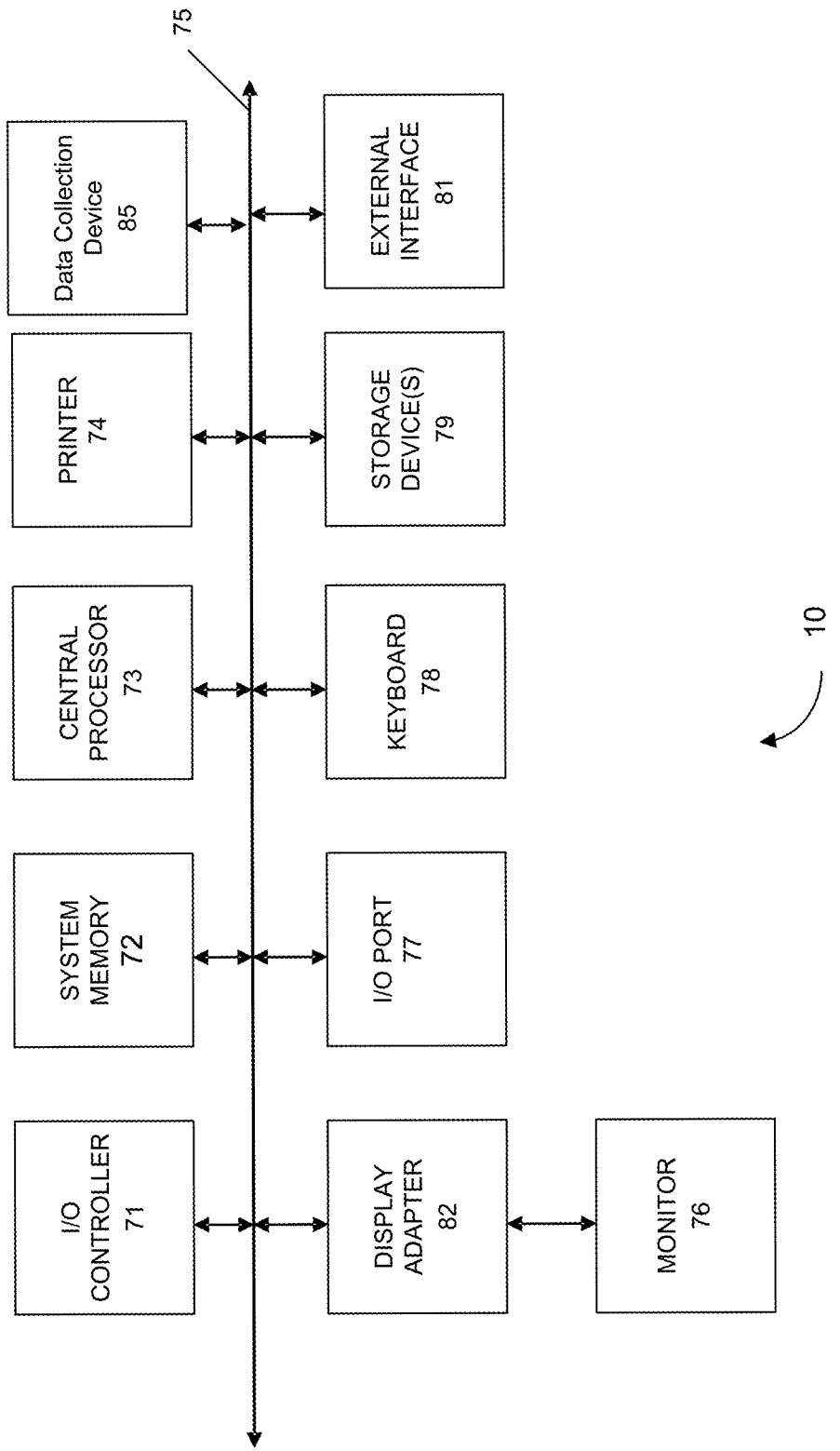
FIG. 32 shows a block diagram of an example computer system usable with system and methods according to embodiments of the present invention.

Any of the computer systems mentioned herein may utilize any suitable number of subsystems. Examples of such subsystems are shown in FIG. 32 in computer system 10. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones, and other mobile devices.

The subsystems shown in FIG. 32 are interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of connections known in the art such as input/output (I/O) port 77 (e.g., USB, FireWire®). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of a plurality of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the operations. Thus, embodiments can be directed to computer systems configured to perform the operations of any of the methods described herein, potentially with different components performing a respective operations or a respective group of operations. Although presented as numbered operations, operations of methods herein can be performed at a same time or in a different order. Additionally, portions of these operations may be used with portions of other operations from other methods. Also, all or portions of an operation may be optional. Additionally, any of the operations of any of the methods can be performed with modules, units, circuits, or other approaches for performing these operations.

The section headings used herein are for organizational purposes only and are not to be construed as limiting the subject matter described.

It is to be understood that the methods described herein are not limited to the particular methodology, protocols, subjects, and sequencing techniques described herein and as such may vary. It is also to be understood that the terminology used herein is for the purpose of describing particular embodiments only, and is not intended to limit the scope of the methods and compositions described herein, which will be limited only by the appended claims. While some embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

Several aspects are described with reference to example applications for illustration. Unless otherwise indicated, any embodiment can be combined with any other embodiment. It should be understood that numerous specific details, relationships, and methods are set forth to provide a full understanding of the features described herein. A skilled artisan, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

While some embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a method" includes a plurality of such methods and reference to "the particle" includes reference to one or more particles and equivalents thereof known to those skilled in the art, and so forth. The invention has now been described in detail for the purposes of clarity and understanding. However, it will be appreciated that certain changes and modifications may be practice within the scope of the appended claims.

VI. References Excluding Those in Sections II, III.B, and III.C

1. Lo Y M, Corbetta N, Chamberlain P F, et al. Presence of fetal DNA in maternal plasma and serum. *Lancet.* 1997; 350(9076):485-487.
2. Lo Y M, Chan K C, Sun H, et al. Maternal plasma DNA sequencing reveals the genome-wide genetic and mutational profile of the fetus. *Sci Transl Med.* 2010; 2(61): 61ra91.
3. Lun F M, Tsui N B, Chan K C, et al. Noninvasive prenatal diagnosis of monogenic diseases by digital size selection and relative mutation dosage on DNA in maternal plasma. *Proc Natl Acad Sci USA.* 2008; 105(50):19920-19925.

4. Yu S C, Chan K C, Zheng Y W, et al. Size-based molecular diagnostics using plasma DNA for noninvasive prenatal testing. *Proc Natl Acad Sci USA*. 2014; 111(23):8583-8588.

5. Jiang P, Peng X, Su X, et al. *Fetal Quant. NPJ Genom Med.* 2016; 1:16013.

6. Chan K C, Ding C, Gerovassili A, et al. Hypermethylated RASSF1A in maternal plasma: A universal fetal DNA marker that improves the reliability of noninvasive prenatal diagnosis. *Clin Chem.* 2006; 52(12):2211-2218.

7. Dhallan R, Au W C, Mattagajasingh S, et al. Methods to increase the percentage of free fetal DNA recovered from the maternal circulation. *JAMA*. 2004; 291(9): 1114-1119.

8. Li Y, Di Naro E, Vitucci A, Zimmermann B, Holzgreve W, Hahn S. Detection of paternally inherited fetal point mutations for beta-thalassemia using size-fractionated cell-free DNA in maternal plasma. *JAMA*. 2005; 293(7): 843-849.

9. Burnham P, Kim M S, Agbor-Enoh S, et al. Single-stranded DNA library preparation uncovers the origin and diversity of ultrashort cell-free DNA in plasma. *Sci Rep.* 2016; 6:27859.

10. Snyder M W, Kircher M, Hill A J, Daza R M, Shendure J. Cell-free DNA Comprises an In Vivo Nucleosome Footprint that Informs Its Tissues-Of-Origin. *Cell.* 2016; 164(1-2):57-68.

11. Nagata S. Apoptotic DNA fragmentation. *Exp Cell Res.* 2000; 256(1): 12-18.

12. Stroun M, Lyautey J, Lederrey C, Olson-Sand A, Anker P. About the possible origin and mechanism of circulating DNA apoptosis and active DNA release. *Clin Chim Acta*. 2001; 313(1-2):139-142.

13. van der Vaart M, Pretorius P J. The origin of circulating free DNA. *Clin Chem.* 2007; 53(12):2215.

14. Mouliere F, El Messaoudi S, Pang D, Dritschilo A, Thierry A R. Multi-marker analysis of circulating cell-free DNA toward personalized medicine for colorectal cancer. *Mol Oncol*. 2014; 8(5):927-941.

15. Chandrananda D, Thorne N P, Bahlo M. High-resolution characterization of sequence signatures due to non-random cleavage of cell-free DNA. *BMC Med Genomics*. 2015; 8:29.

16. Chan K C, Zhang J, Hui A B, et al. Size distributions of maternal and fetal DNA in maternal plasma. *Clin Chem.* 2004; 50(1):88-92.

17. Vong J S L, Tsang J C H, Jiang P, et al. Single-Stranded DNA Library Preparation Preferentially Enriches Short Maternal DNA in Maternal Plasma. *Clin Chem.* 2017; 63(5):1031-1037.

18. New M I, Tong Y K, Yuen T, et al. Noninvasive prenatal diagnosis of congenital adrenal hyperplasia using cell-free fetal DNA in maternal plasma. *J Clin Endocrinol Metab.* 2014; 99(6):E1022-1030.

19. Li R, Yu C, Li Y, et al. SOAP2: an improved ultrafast tool for short read alignment. *Bioinformatics*. 2009; 25(15): 1966-1967.

20. Hong H, Xu L, Tong W. Assessing consistency between versions of genotype-calling algorithm Birdseed for the Genome-Wide Human SNP Array 6.0 using HapMap samples. *Adv Exp Med Biol.* 2010; 680:355-360.

21. Cheng T H T, Lui K O, Peng X L, et al. DNase1 Does Not Appear to Play a Major Role in the Fragmentation of Plasma DNA in a Knockout Mouse Model. *Clin Chem.* 2018; 64(2):406-408.

22. Chen L, Liu P, Evans T C, Ettwiller L M. DNA damage is a pervasive cause of sequencing errors, directly confounding variant identification. *Science.* 2017; 355(6326): 752-756.

23. Ardui S, Ameur A, Vermeesch J R, Hestand M S. Single molecule real-time (SMRT) sequencing comes of age: applications and utilities for medical diagnostics. *Nucleic Acids Res.* 2018; 46(5):2159-2168.

24. Giacona M B, Ruben G C, Iczkowski K A, Roos T B, Porter D M, Sorenson G D. Cell-free DNA in human blood plasma: length measurements in patients with pancreatic cancer and healthy controls. *Pancreas.* 1998; 17(1):89-97.

25. Holdenrieder S, Stieber P, Förg T, et al. Apoptosis in serum of patients with solid tumours. *Anticancer Res.* 1999; 19(4A):2721-2724.

26. Jahr S, Hentze H, Englisch S, et al. DNA fragments in the blood plasma of cancer patients: quantitations and evidence for their origin from apoptotic and necrotic cells. *Cancer Res.* 2001; 61(4):1659-1665.

27. Thierry A R, El Messaoudi S, Gahan P B, Anker P, Stroun M. Origins, structures, and functions of circulating DNA in oncology. *Cancer Metastasis Rev.* 2016; 35(3): 347-376.

28. Sun K, Jiang P, Wong A I C, et al. Size-tagged preferred ends in maternal plasma DNA shed light on the production mechanism and show utility in noninvasive prenatal testing. *Proc Natl Acad Sci USA*. 2018; 115(22):E5106-E5114.

29. Chen E Z, Chiu R W, Sun H, et al. Noninvasive prenatal diagnosis of fetal trisomy 18 and trisomy 13 by maternal plasma DNA sequencing. *PLoS One.* 2011; 6(7):e21791.

30. Chiu R W, Akolekar R, Zheng Y W, et al. Non-invasive prenatal assessment of trisomy 21 by multiplexed maternal plasma DNA sequencing: large scale validity study. *BMJ.* 2011; 342:c7401.

31. Palomaki G E, Deciu C, Kloza E M, et al. DNA sequencing of maternal plasma reliably identifies trisomy 18 and trisomy 13 as well as Down syndrome: an international collaborative study. *Genet Med.* 2012; 14(3):296-305.

32. Nicolaides K H, Syngelaki A, Ashoor G, Birdir C, Touzet G. Noninvasive prenatal testing for fetal trisomies in a routinely screened first-trimester population. *Am J Obstet Gynecol.* 2012; 207(5):374.e371-376.

33. Pergament E, Cuckle H, Zimmermann B, et al. Single-nucleotide polymorphism-based noninvasive prenatal screening in a high-risk and low-risk cohort. *Obstet Gynecol.* 2014; 124(2 Pt 1):210-218.

34. Canick J A, Palomaki G E, Kloza E M, Lambert-Messerlian G M, Haddow J E. The impact of maternal plasma DNA fetal fraction on next generation sequencing tests for common fetal aneuploidies. *Prenat Diagn.* 2013; 33(7):667-674.

35. Dar P, Curnow K J, Gross S J, et al. Clinical experience and follow-up with large scale single-nucleotide polymorphism-based noninvasive prenatal aneuploidy testing. *Am J Obstet Gynecol.* 2014; 211(5):527.e521-527.e517.

36. Norton M E, Wapner R J. Cell-free DNA Analysis for Noninvasive Examination of Trisomy. *N Engl J Med.* 2015; 373(26):2582.

37. Yared E, Dinsmoor M J, Endres L K, et al. Obesity increases the risk of failure of noninvasive prenatal screening regardless of gestational age. *Am J Obstet Gynecol.* 2016; 215(3):370.e371-376.

38. Nolin S L, Brown W T, Glicksman A, et al. Expansion of the fragile X CGG repeat in females with premutation or intermediate alleles. *Am J Hum Genet.* 2003; 72(2): 454-464.
39. McLennan Y, Polussa J, Tassone F, Hagerman R. Fragile x syndrome. *Curr Genomics.* 2011; 12(3):216-224.
40. Lui Y Y, Chik K W, Chiu R W, Ho C Y, Lam C W, Lo Y M. Predominant hematopoietic origin of cell-free DNA in plasma and serum after sex-mismatched bone marrow transplantation. *Clin Chem.* 2002; 48(3):421-427.
41. Diegoli T M, Farr M, Cromartie C, Coble M D, Bille T W. An optimized protocol for forensic application of the PreCR™ Repair Mix to multiplex STR amplification of UV-damaged DNA. *Forensic Sci Int Genet.* 2012; 6(4): 498-503.
42. Ye J, Chen C, Yuan Y, et al. Haplotype-based Noninvasive Prenatal Diagnosis of Hyperphenylalaninemia through Targeted Sequencing of Maternal Plasma. *Sci Rep.* 2018; 8(1):161.
43. Ma D, Yuan Y, Luo C, et al. Noninvasive prenatal diagnosis of 21-Hydroxylase deficiency using target capture sequencing of maternal plasma DNA. *Sci Rep.* 2017; 7(1):7427.
44. Rajan-Babu I S, Lian M, Cheah F S H, et al. FMR1 CGG repeat expansion mutation detection and linked haplotype analysis for reliable and accurate preimplantation genetic diagnosis of fragile X syndrome. *Expert Rev Mol Med.* 2017; 19:e10.
45. Tural S, Tekcan A, Kara N, Elbistan M, Given D, Ali Tasdemir H. FMR1 gene mutation screening by TP-PCR in patients with premature ovarian failure and fragile-X. *Gynecol Endocrinol.* 2015; 31(3):191-195.
46. Naumann A, Hochstein N, Weber S, Fanning E, Doerfler W. A distinct DNA-methylation boundary in the 5'-upstream sequence of the FMR1 promoter binds nuclear proteins and is lost in fragile X syndrome. *Am J Hum Genet.* 2009; 85(5):606-616.
47. Hosomichi K, Shiina T, Tajima A, Inoue I. The impact of next-generation sequencing technologies on HLA research. *J Hum Genet.* 2015; 60(11):665-673.
48. Sun K, Jiang P, Chan K C, et al. Plasma DNA tissue mapping by genome-wide methylation sequencing for noninvasive prenatal, cancer, and transplantation assessments. *Proc Natl Acad Sci USA.* 2015; 112(40):E5503-5512.
49. Lehmann-Werman R, Neiman D, Zemmour H, et al. Identification of tissue-specific cell death using methylation patterns of circulating DNA. *Proc Natl Acad Sci USA.* 2016; 113(13):E1826-1834.
50. Chan R W, Jiang P, Peng X, et al. Plasma DNA aberrations in systemic lupus erythematosus revealed by genomic and methylomic sequencing. *Proc Natl Acad Sci USA.* 2014; 111(49):E5302-5311.
51. Napirei M, Ludwig S, Mezrhab J, Klöckl T, Mannherz H G. Murine serum nucleases—contrasting effects of plasmin and heparin on the activities of DNase1 and DNase1-like 3 (DNase1l3). *FEBS J.* 2009; 276(4): 1059-1073.

What is claimed is:

1. A method of determining an extent of cfDNA damage in an individual, the method comprising:
receiving a first sample comprising a first set of double-stranded nucleic acid molecules derived from cell-free nucleic acid molecules in a biological sample obtained from the individual, wherein:
one or more double-stranded nucleic acid molecules of the first set of double-stranded nucleic acid molecules each have one or more defects, and
the one or more defects are present in the respective double-stranded nucleic acid molecule at a location at least one nucleotide away from a closest end of the respective double-stranded nucleic acid molecule;
receiving a second sample comprising a second set of double-stranded nucleic acid molecules derived from the cell-free nucleic acid molecules in the biological sample;
adding a first mixture comprising an enzyme to the first sample;
adding a second mixture to the second sample, wherein the second mixture excludes the enzyme;
repairing the one or more defects in each of the one or more double-stranded nucleic acid molecules of the first set of double-stranded nucleic acid molecules using the enzyme to produce a repaired first set of double-stranded nucleic acid molecules, wherein the second set of double-stranded nucleic acid molecules is unrepaired;
sequencing the repaired first set of double-stranded nucleic acid molecules to determine a first set of reads;
sequencing the second set of double-stranded nucleic acid molecules to determine a second set of reads;
determining, based at least on sizes of the first set of reads and the second set of reads, a value of a parameter characterizing a difference in defects between the repaired first set of double-stranded nucleic acid molecules and the second set of double-stranded nucleic acid molecules;
comparing the value of the parameter to a reference value, wherein the reference value is determined using one or more healthy subjects; and
determining an extent of cfDNA damage for the individual based on the comparison of the value of the parameter to the reference value.

2. The method of claim 1, wherein:
the first mixture comprises a plurality of enzymes.

3. The method of claim 1, wherein the first sample and the second sample are equal in volume.

4. The method of claim 1, wherein:
the first mixture comprises a plurality of enzymes, and
the second mixture excludes the plurality of enzymes.

5. The method of claim 1, further comprising:
performing targeted capture enrichment such that the first set of reads is from one or more selected genomic regions, and
performing targeted capture enrichment such that the second set of reads is from the one or more selected genomic regions, wherein:
the first set of reads does not comprise reads from double-stranded nucleic acid molecules having one or more defects,
the second set of reads does not comprise reads from double-stranded nucleic acid molecules having one or more defects,
the first set of reads has a first amount of reads,
the second set of reads has a second amount of reads, and
the value of the parameter is determined using the first amount of reads and the second amount of reads.

6. The method of claim 5, wherein:
the value of the parameter is determined using a difference between the first amount of reads and the second amount of reads, or the value of the parameter is determined using a ratio of the first amount of reads and the second amount of reads.

7. The method of claim 5, wherein:
the first amount of reads is a normalized amount of reads, and
the second amount of reads is a normalized amount of reads.

8. The method of claim 1, further comprising:
calculating a first statistical value characterizing the sizes of the first set of reads, and
calculating a second statistical value characterizing the sizes of the second set of reads,
wherein:
the value of the parameter is determined using the first statistical value and the second statistical value.

9. The method of claim 1, wherein:
the parameter is multidimensional,
a first dimension of the parameter is based on a range of sizes of the first set of reads and the second set of reads, and
a second dimension of the parameter comprises an amount of the first set of reads and the second set of reads for a given size.

10. The method of claim 9, wherein the first dimension is a range of ratios of the sizes of the first set of reads and the second set of reads to a reference size.

11. The method of claim 9, wherein:
the reference value is multidimensional, and
the reference value specifies amounts of nucleic acid molecules at different sizes.

12. The method of claim 1, wherein comparing the value of the parameter to the reference value comprises determining whether the value of the parameter exceeds the reference value.

13. The method of claim 12, wherein determining the extent of cfDNA damage is based on a difference between the value of the parameter and the reference value.

14. The method of claim 1, wherein the first set of double-stranded nucleic acid molecules comprises at least 10,000 double-stranded nucleic acid molecules.

* * * * *